(12) United States Patent
Malyshev et al.

(10) Patent No.: US 11,180,520 B2
(45) Date of Patent: Nov. 23, 2021

(54) REVERSIBLE MODIFICATIONS OF NUCLEOTIDES

(71) Applicant: Omniome, Inc., San Diego, CA (US)

(72) Inventors: Denis Malyshev, San Diego, CA (US); Aaron W. Feldman, San Diego, CA (US)

(73) Assignee: OMNIOME, INC., San Diego, CA (US)

(*) Notice: Subject to any disclaimer, the term of this patent is extended or adjusted under 35 U.S.C. 154(b) by 0 days.

(21) Appl. No.: 17/016,992

(22) Filed: Sep. 10, 2020

(65) Prior Publication Data
US 2021/0070795 A1    Mar. 11, 2021

Related U.S. Application Data

(60) Provisional application No. 62/898,152, filed on Sep. 10, 2019.

(51) Int. Cl.
C07H 1/00 (2006.01)
C07H 19/10 (2006.01)

(52) U.S. Cl.
CPC ............... C07H 1/00 (2013.01); C07H 19/10 (2013.01)

(58) Field of Classification Search
CPC .................................. C07H 1/00; C07H 19/10
See application file for complete search history.

(56) References Cited

U.S. PATENT DOCUMENTS

| | | |
|---|---|---|
| 5,130,238 A | 7/1992 | Malek et al. |
| 5,455,166 A | 10/1995 | Walker |
| 5,599,675 A | 2/1997 | Brenner et al. |
| 5,641,658 A | 6/1997 | Adams et al. |
| 5,695,934 A | 12/1997 | Brenner |
| 5,750,341 A | 5/1998 | Macevicz |
| 5,863,722 A | 1/1999 | Brenner |
| 5,888,737 A | 3/1999 | DuBridge et al. |
| 6,140,489 A | 10/2000 | Brenner |
| 6,175,002 B1 | 1/2001 | Dubridge et al. |
| 6,214,587 B1 | 4/2001 | Dattagupta et al. |
| 6,266,459 B1 | 7/2001 | Walt et al. |
| 6,355,431 B1 | 3/2002 | Chee et al. |
| 6,770,441 B2 | 8/2004 | Dickinson et al. |
| 6,859,570 B2 | 2/2005 | Walt et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,544,794 B1 | 6/2009 | Benner et al. |
| 7,622,294 B2 | 11/2009 | Walt et al. |
| 7,964,352 B2 | 6/2011 | Wu et al. |
| 8,034,923 B1 | 10/2011 | Brenner et al. |
| 8,951,781 B2 | 2/2015 | Reed et al. |
| 9,164,053 B2 | 10/2015 | Collins et al. |
| 9,193,996 B2 | 11/2015 | Buermann et al. |

(Continued)

FOREIGN PATENT DOCUMENTS

| | | |
|---|---|---|
| WO | WO 1989/10977 A1 | 11/1989 |
| WO | WO 91/06678 A1 | 5/1991 |

(Continued)

OTHER PUBLICATIONS

U.S. Appl. No. 62/732,510.
U.S. Appl. No. 62/767,712.
Bains, W. et al. (Dec. 7, 1988). "A novel method for nucleic acid sequence determination," *Journal of Theoretical Biology* 135(3):303-307.
Bentley, D. R. et al. (Nov. 6, 2008). "Accurate whole human genome sequencing using reversible terminator chemistry," *Nature* 456(7218):53-59.
Cockroft, S.L. et al. (Jan. 23, 2008, e-published Jan. 1, 2008). "A Single-Molecule Nanopore Device Detects DNA Polymerase Activity with Single-Nucleotide Resolution" *J. Am. Chem. Soc.* 130(3):818-820.

(Continued)

*Primary Examiner* — Lawrence E Crane
(74) *Attorney, Agent, or Firm* — Mintz, Levin, Cohn, Ferris, Glovsky and Popeo, P.C.

(57) ABSTRACT

Disclosed herein, inter alia, are methods for modifying a nucleotide, for example including reacting a nucleotide having a 3'-O-oxime moiety such as

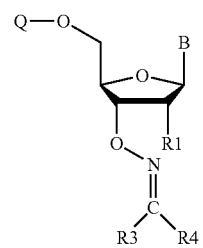

with a reagent having an —ONH$_2$ moiety to produce a nucleotide having a 3'-O—NH$_2$ moiety such as

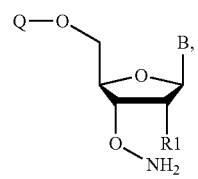

wherein the reagent having the —ONH$_2$ moiety further comprises alkyl, alkenyl, cycloalkyl, cycloalkenyl, cycloalkynyl, aryl, heteroaryl, heteroalicyclyl, aralkyl, heteroaralkyl, or (heteroalicyclyl)alkyl.

6 Claims, 3 Drawing Sheets

(56) References Cited

U.S. PATENT DOCUMENTS

| | | | |
|---|---|---|---|
| 9,399,798 | B2 | 7/2016 | Stupi et al. |
| 9,476,080 | B2 | 10/2016 | Li et al. |
| 9,829,456 | B1 | 11/2017 | Jin et al. |
| 10,036,064 | B2 | 7/2018 | Merriman et al. |
| 10,041,115 | B2 | 8/2018 | Stupi et al. |
| 10,125,391 | B2 | 11/2018 | Turner et al. |
| 10,246,744 | B2 * | 4/2019 | Vijayan ............... C12Q 1/6874 |
| 10,378,051 | B2 | 8/2019 | Meuleman et al. |
| 10,443,098 | B2 * | 10/2019 | Vijayan ............. C12N 15/1068 |
| 10,472,383 | B2 * | 11/2019 | Benner ................. C07H 19/10 |
| 10,508,296 | B2 * | 12/2019 | Merriman ........... C12Q 1/6825 |
| 10,545,115 | B2 * | 1/2020 | Boyanov ............. C12Q 1/6825 |
| 10,597,643 | B2 * | 3/2020 | Iyidogan ............. C12N 9/1252 |
| 10,737,267 | B2 * | 8/2020 | Kilcoin ................ F04B 23/025 |
| 2002/0055100 | A1 | 5/2002 | Kawashima et al. |
| 2004/0002090 | A1 | 1/2004 | Mayer et al. |
| 2004/0096853 | A1 | 5/2004 | Mayer |
| 2005/0064460 | A1 | 3/2005 | Holliger et al. |
| 2005/0130173 | A1 | 6/2005 | Leamon et al. |
| 2007/0007991 | A1 | 1/2007 | Lee et al. |
| 2007/0099208 | A1 | 5/2007 | Drmanac et al. |
| 2007/0128624 | A1 | 6/2007 | Gormley et al. |
| 2008/0009420 | A1 | 1/2008 | Schroth et al. |
| 2008/0108082 | A1 | 5/2008 | Rank et al. |
| 2009/0026082 | A1 | 1/2009 | Rothberg et al. |
| 2009/0127589 | A1 | 5/2009 | Rothberg et al. |
| 2009/0247414 | A1 | 10/2009 | Obradovic et al. |
| 2010/0111768 | A1 | 5/2010 | Banerjee et al. |
| 2010/0137143 | A1 | 6/2010 | Rothberg et al. |
| 2010/0282617 | A1 | 11/2010 | Rothberg et al. |
| 2012/0270305 | A1 | 10/2012 | Reed et al. |
| 2017/0022553 | A1 | 1/2017 | Vijayan et al. |
| 2017/0240962 | A1 | 8/2017 | Merriman et al. |
| 2017/0314072 | A1 | 11/2017 | Vijayan et al. |
| 2018/0044727 | A1 | 2/2018 | Vijayan et al. |
| 2018/0051316 | A1 | 2/2018 | Collins et al. |
| 2018/0112265 | A1 | 4/2018 | Boyanov et al. |
| 2018/0155698 | A1 | 6/2018 | Iyidogan et al. |
| 2018/0155773 | A1 | 6/2018 | Gunderson et al. |
| 2018/0187245 | A1 | 7/2018 | Dambacher et al. |
| 2018/0208983 | A1 | 7/2018 | Dambacher et al. |
| 2018/0265537 | A1 | 9/2018 | Benner |
| 2018/0280975 | A1 | 10/2018 | Kilcoin et al. |
| 2018/0305727 | A1 | 10/2018 | Merriman et al. |
| 2019/0055596 | A1 | 2/2019 | Buermann et al. |

FOREIGN PATENT DOCUMENTS

| | | |
|---|---|---|
| WO | WO 00/63437 A2 | 10/2000 |
| WO | WO 00/63437 A3 | 10/2000 |
| WO | WO 2004/018497 A2 | 3/2004 |
| WO | WO 2004/018497 A3 | 3/2004 |
| WO | WO 2005/010145 A2 | 2/2005 |
| WO | WO 2005/010145 A3 | 2/2005 |
| WO | WO 2005/065814 A1 | 7/2005 |
| WO | WO 2007/123744 A2 | 11/2007 |
| WO | WO 2007/123744 A3 | 11/2007 |

OTHER PUBLICATIONS

Dean, F.B. et al. (Apr. 16, 2002). "Comprehensive human genome amplification using multiple displacement amplification," *PNAS USA* 99(8):5261-5266.

Dressman, D. et al. (Jul. 22, 2003, e-published Jul. 11, 2003). "Transforming single DNA molecules into fluorescent magnetic particles for detection and enumeration of genetic variations," *PNAS USA* 100(15):8817-8822.

Drmanac, S. et al. (Jan. 1998). "Accurate sequencing by hybridization for DNA diagnostics and individual genomics," *Nature Biotechnology* 16(1):54-58.

Fodor, S.P. et al. (Feb. 15, 1991). "Light-directed, spatially addressable parallel chemical synthesis," *Science* 251(4995):767-773.

Healy, K. (Aug. 2007). "Nanopore-based single-molecule DNA analysis," *Nanomedicine* 2(4):459-481.

Lage, J.M. et al. (Feb. 2003). "Whole Genome Analysis of Genetic Alterations in Small DNA Samples Using Hyperbranched Strand Displacement Amplification and Array-CGH," *Genome Research* 13(2):294-307.

Lizardi, P.M. et al. (Jul. 19, 1998). "Mutation detection and single-molecule counting using isothermal rolling-circle amplification," *Nat Genet* 19(3):225-232.

Shendure, J. et al. (Sep. 9, 2005, e-published Aug. 4, 2005). "Accurate multiplex polony sequencing of an evolved bacterial genome," *Science* 309(5741):1728-1732.

Soni, G.V. et al. (Nov. 2007, e-published Sep. 21, 2007). "Progress toward Ultrafast DNA Sequencing Using Solid-State Nanopores," *Clin Chem* 53(11):1996-2001.

Walker et al. (1995). *Molecular Methods for Virus Detection*, Wiedbrauk, D.L et al. editors, Academic Press, Inc., Table of Contents.

Walker, G.T. et al. (Apr. 11, 1992). "Strand displacement amplification—an isothermal, in vitro DNA amplification technique," *Nucleic Acids Research* 20(7):1691-1696.

International Search Report dated Nov. 23, 2020, for PCT Application No. PCT/US2020/050126, filed Sep. 10, 2020, 6 pages.

Hutter, D. et al. (Nov. 2010). "Labeled nucleoside triphosphates with reversibly terminating aminoalkoxyl groups," Nucleosides, Nucleotides Nucleic Acids 29(11):879-895.

Written Opinion dated Nov. 23, 2020, for PCT Application No. PCT/US2020/050126, filed Sep. 10, 2020, 9 pages.

Yang, T-F. et al. (2001). "Synthesis of Thymidine Dimer Containing Novel (N-Acetyl)imino Linkage," *Journal of the Chinese Chemical Society* 48:949-952.

* cited by examiner

REVERSIBLE MODIFICATIONS OF NUCLEOTIDES

CROSS-REFERENCES TO RELATED APPLICATIONS

This application claims the benefit of U.S. Provisional Application No. 62/898,152, filed Sep. 10, 2019, which is incorporated herein by reference in its entirety and for all purposes.

BACKGROUND

The present disclosure relates generally to reversible blocking of nucleotides and nucleic acids to inhibit enzyme catalyzed modification of their 3' hydroxyl moieties, and has specific applicability to nucleic acid sequencing processes that employ cyclic reversible termination.

Genomes have been analogized as operating manuals containing instructions for development and functioning of individual organisms. Genomes have been shown to guide growth and development, direct the function of vital organs, influence mood and behavior, etc. The uniqueness of every individual is derived in significant part from the unique composition of their genome. The differences between individuals can be observed as differences in the sequence of nucleotides in the DNA that constitutes their genome. Great strides have been made in identifying how those sequence differences predict risk of disease, chances of having adverse reactions to certain therapeutic drugs, and chances of having certain abilities and personality traits, to name a few.

Recently, the diagnostic potential for genomic information has accelerated due to commercialization of DNA sequencing platforms that are capable of sequencing at the scale of the typical human genome, which has a sequence of 3 billion nucleotides. Although the throughput and cost for sequencing have improved vastly over the last few decades, there are still many diseases for which diagnostic sequence signatures have not been identified and the cost of sequencing is still out of reach for many clinical applications.

Many sequencing technologies that have been developed, including several that are in wide commercial use, employ a cyclic reversible terminator (CRT) process. The CRT process extends a primer along a DNA template of interest such that each cycle results in detection of a single position in the template. The cycles are repeated to effectively walk down the template in DNA while reading the sequence in single nucleotide steps. Performing 100 CRT cycles produces a sequence read of 100 nucleotides. Single nucleotide step size, and as a result single nucleotide resolution for the resulting sequence read, is achieved by incrementing the primer with a nucleotide having a 3' reversible terminator moiety. The primer, after adding the reversibly terminated nucleotide, cannot be further extended until it is treated with an appropriate deblocking reagent to remove the reversible terminator moiety. The accuracy and read length of most CRT processes, including those that are in commercial use today, are known to be compromised due to inefficiencies in the steps that incorporate reversible terminators into primers and in the steps used for deblocking the primers. Moreover, many CRT processes use deblocking reagents that can damage the very DNA that is to be sequenced. Because sequencing is a cumulative process, even small inefficiencies in primer extension, primer deblocking and resistance to DNA damage can add up to a substantial adverse impact over the many cycles of a sequencing process.

Thus, there exists a need for improved reagents and methods for reversible termination of nucleotides and nucleic acids. The present invention satisfies this need and provides related advantages as well.

BRIEF SUMMARY

The present disclosure provides a composition that includes solution containing a nucleotide having a protecting group such as a 3'-O-oxime moiety and a reagent to remove the protecting group and deliver to the protecting group's position a blocking group, such as a reagent having the structure R2-ONH$_2$. A number of R2 moieties are consistent with the present disclosure. In some cases, R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. Alternately or in combination, R2 comprises a moiety having a molecular weight of at least 24, at least 25, at least 26, at least 27, at least 28, at least 29, at least 30, at least 31, at least 32, at least 33, at least 34, at least 35, at least 36, or greater than 36 g/mol. Similarly, an R2 moiety as contemplated herein has a molecular weight of no more than 1000, no more than 500, no more than 400, no more than 300, no more than 250, no more than 200, no more than 150, or no more than 100 g/mol. Alternately or in combination, various R2 embodiments comprise one or more of the following: at least two carbon nuclei, fluorine nucleus, a phosphorous nucleus, a nitrogen nucleus, a silicon nucleus, an oxygen nucleus, a hydroxy moiety, heterocyclic ring, a phenyl ring, or other moiety, alone or in combination with one another.

In particular configurations, a representative nucleotide starting material for methods or compositions herein has the structure:

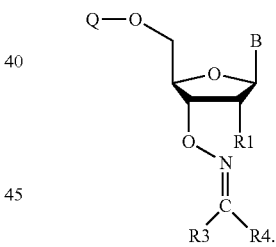

B can be a nucleobase. R1 can independently be a halogen, OCH$_3$, H or OH, or may carry an alternate modification at the 2' R1 position, such that the nucleotide is variously a ribonucleotide or a deoxyribonucleotide. Q can be independently monophosphate, diphosphate, triphosphate, nucleic acid, hydrogen, or other moiety, such as a surface or linker bonded to a surface. R3 and R4 can be independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. By way of example, the protecting group moiety at the 3' position of the nucleotide can be an aldoxime (such that one of R3 or R4 is hydrogen) or a ketoxime (wherein neither R3 nor R4 is hydrogen). Other protecting group moieties are contemplated herein and consistent with the present disclosure.

The present disclosure also provides methods for modifying a nucleotide. The methods can be carried out by reacting a nucleotide having a protecting group such as a 3'-O-oxime moiety with a reagent to remove the protecting group and deliver to the protecting group's position a blocking group, such as a reagent having the structure R2-ONH$_2$ to produce a nucleotide having a 3'-O—NH$_2$ moiety, wherein R2 is independently R2 is —C(R6)(R7)(R8), —C(O)(R6), —P(O)(R6)(R7), —C(R6)(=C(R7)(R8)), —Si(R6)(R7)(R8), —SO$_2$(R6), substituted or unsubstituted cycloalkyl (e.g., C$_3$-C$_8$, C$_3$-C$_6$, or C$_5$-C$_6$), substituted or unsubstituted cycloalkenyl (e.g., C$_3$-C$_8$, C$_3$-C$_6$, or C$_5$-C$_6$), substituted or unsubstituted cycloalkynyl (e.g., C$_3$-C$_8$, C$_3$-C$_6$, or C$_5$-C$_6$), substituted or unsubstituted heteroalicyclyl (e.g., 3 to 8 membered, 3 to 6 membered, or 5 to 6 membered), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl). In some cases R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. R2 moieties may comprise a number of constituents, alone or in combination, to covey the benefits disclosed herein. Some R2 moieties variously comprise at least 2, at least 3, at least 4, at least 5, at least 6, or more than 6 carbon nuclei. Similarly, some R2 comprise at least one of the following: at least 1 nitrogen nucleus, at least one silicon nucleus, at least one phosphorous nucleus, at least one fluorine nucleus or at least one other constituent. R2 moieties are in some cases partially or fully fluorinated, or partially or fully hydrogenated. In some cases an R2 moiety comprises at least one component to facilitate solubility. Reagents having structures to deliver alternate blocking groups or reversible terminator moieties, such as ONHCH$_3$, O—CH$_2$N$_3$, or other moiety such as those consistent with reversible termination of nucleic acid extension, are also contemplated herein. In some configurations, the nucleotide that has the 3'-O-oxime moiety can have the structure:

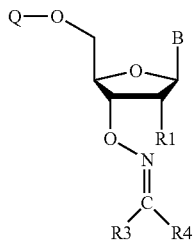

and the nucleotide that has the 3'-O—NH$_2$ moiety can have the structure:

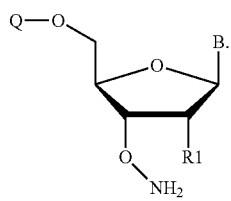

B can be a nucleobase. R1 can independently be a halogen, OCH$_3$, H or OH. Q can be independently monophosphate, diphosphate, triphosphate, nucleic acid, or other moiety, such as a surface or linker bonded to a surface. R3 and R4 can be independently H, CH$_3$, alkyl, alkenyl, alky-nyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. By way of example, the moiety at the 3' position of the nucleotide can be an aldoxime (such that one of R3 or R4 is hydrogen) or a ketoxime (neither of R3 or R4 is hydrogen). In particular configurations, a nucleotide starting material for methods or compositions herein has the structure:

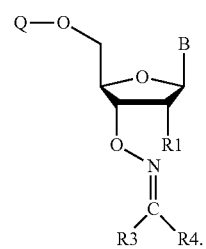

B can be a nucleobase. R1 can independently be a halogen, OCH$_3$, H or OH. Q can be independently monophosphate, diphosphate, triphosphate, nucleic acid, or other moiety, such as a surface or linker bonded to a surface. R3 and R4 can be independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. By way of example, the protecting group moiety at the 3' position of the nucleotide can be an aldoxime (such that one of R3 or R4 is hydrogen) or a ketoxime (wherein neither R3 nor R4 is hydrogen). Other protecting group moieties are contemplated herein and consistent with the present disclosure. The present disclosure also provides methods for modifying a nucleotide. The methods can be carried out by reacting a nucleotide having a protecting group such as a 3'-O-oxime moiety with a reagent to deliver a blocking group, such as a reagent having the structure R2-ONH$_2$ to produce a nucleotide having a 3'-O—NH$_2$ moiety, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. Reagents having structures to deliver alternate blocking groups, such as ONHCH$_3$, O—CH$_2$N$_3$, or other moiety consistent with reversible termination of nucleic acid extension, are also contemplated herein.

The present disclosure further provides a kit that includes a first vessel containing a nucleotide having a 3'-O-oxime moiety and a second vessel containing a reagent having the structure R2-ONH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. In some configurations, the nucleotide can have the structure:

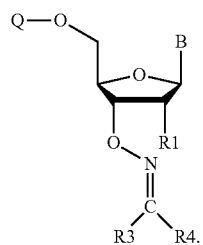

B can be a nucleobase. R1 can independently be a halogen, $OCH_3$, H or OH. Q can be independently monophosphate, diphosphate, triphosphate, nucleic acid, or other moiety, such as a surface or linker bonded to a surface. R3 and R4 can be independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. By way of example, the moiety at the 3' position of the nucleotide can be an aldoxime (such that one of R3 or R4 is hydrogen) or a ketoxime (neither of R3 or R4 is hydrogen).

BRIEF DESCRIPTION OF THE DRAWING

FIG. 1A illustrates that as R2 increases in molecular weight, one sees a decrease in dC degradation. Similarly, as R2 increases in molecular weight, one sees an increase in starting material consumption.

DETAILED DESCRIPTION

Figures 1A, 1B:
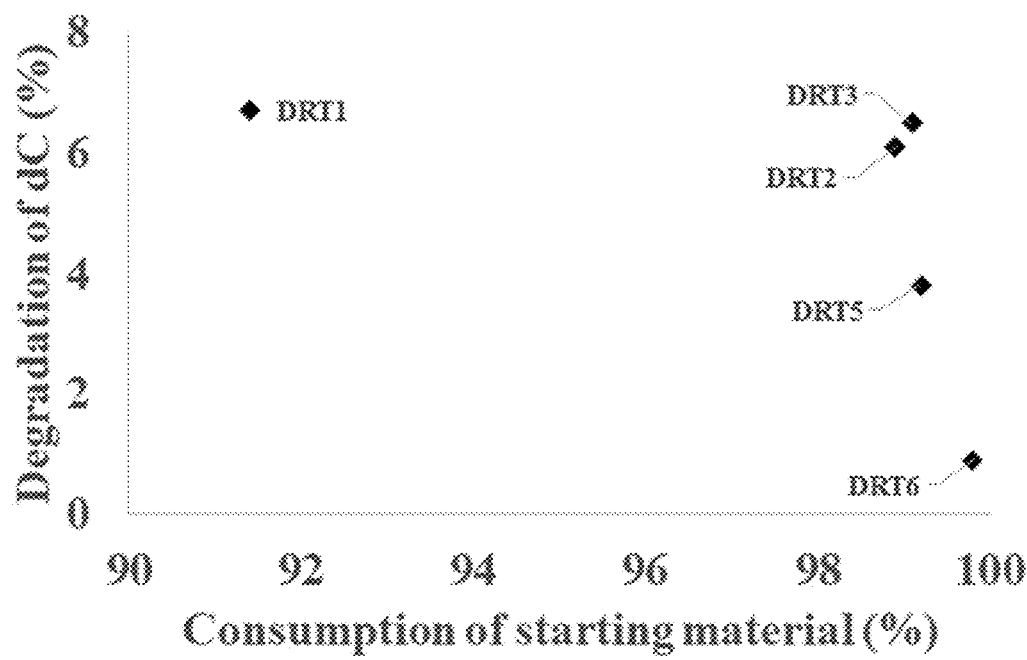
FIG. 1A shows a plot of percent nucleotide degradation vs. percent consumption of the 3'-O—(N-acetone oxime) moiety for 3'-O—(N-acetone oxime)-dCTP when treated with various candidate DRT ('deblocking reversible terminator') aminooxy reagents sharing an —O—$NH_2$ reversible terminator moiety tethered to various R2 groups. Reactions were performed as described in Example 1 and assayed after 1 hour for a 25 C reaction.
FIG. 1B lists the chemical identities of the DRT reagents assayed in FIG. 1A, indicating their various R2 moieties.

The present disclosure provides compositions and methods that are useful for synthesis of nucleotides having moieties at the 3' position, such as moieties that protect the 3' position from modifications such as chemical modifications and enzymatic modifications, such as addition of a nucleotide as effected by template directed DNA polymerase enzymes. A nucleotide that is protected in this way can be referred to as being blocked or terminated. For example, when a nucleotide having a protected 3' position is incorporated into an extending nucleic acid strand as the 3' nucleotide moiety of a nucleic acid primer, the extended primer is effectively blocked from being further extended by a polymerase or ligase. In other words, primer extension has been terminated.

In particular configurations or embodiments, a blocked or terminated nucleotide can have a reversible terminator moiety such as a 3'-$ONH_2$ moiety that, unlike the native hydroxyl found at the 3' position of deoxyribonucleotides and ribonucleotides, is resistant to modification by certain enzymes and chemical reagents. Under certain conditions the 3'-$ONH_2$ moiety can be chemically converted to a hydroxyl, for example when the blocked nucleotide is treated with an acid such as nitrous acid. Replacement of the —O—$NH_2$ moiety as a whole with an —OH moiety or replacement of the —$NH_2$ moiety with an —H both effectively result in deblocking, and the fate of the 3' O in deblocking is immaterial, so long as the final product has a 3' OH available for polymerase-mediated nucleic acid extension. As such the 3'-$ONH_2$ moiety functions as a reversible terminator when coupled with the deblocking reagents of the present disclosure. Other reversible terminators that are readily removed to recover a 3' hydroxy moiety compatible with enzymatic strand extension are consistent with the disclosure herein, such that not all embodiments herein are limited to the preparation of a nucleotide having a 3'-O—$NH_2$ moiety. Exemplary alternatives include 3'-O—$NHCH_3$, —O—$CH_2N_3$, and others known in the art that block strand extension when attached at the 3' position of the 3' end of a nucleic acid strand, while at the same time do not preclude binding by a DNA or other nucleic acid polymerase such that nucleotides carrying such reversible terminators may be added, at their 5' ends, to the 3' hydroxy groups of unblocked nucleotides or nucleotide polymers to produce 3' terminated nucleic acid strands.

Reversible termination of nucleotides are useful for a variety of applications. For example, a variety of nucleic acid sequencing platforms utilize a cyclic reversible terminator (CRT) process in which the sequence of a template nucleic acid is read while incrementally extending a primer nucleic acid along the template. Incremental extension can be achieved in CRT processes by structuring each cycle to include a step of extending the primer through addition of a reversibly terminated nucleotide (or oligonucleotide reversibly terminated at its 3' end) followed by deblocking the extended primer. In each cycle, a detection step is also carried out in order to identify the type of nucleotide that is present at a particular position that has been aligned with respect to the extended primer.

The reversibly terminated nucleotides, and methods for their synthesis, set forth herein provide advantages of very efficiently replacing 3' protecting groups such as 3'-O-oximes or other groups added to facilitate the chemical manipulation of other regions of a nucleic acid, such as addition of a triphosphate moiety to a nucleotide 5' position. Without being bound by theory, it is predicted that because CRT is a generally cumulative process, any errors or inefficiencies in blocking and deblocking steps will produce a cumulatively adverse effect. For example, phasing is the phenomenon whereby individual nucleic acid molecules within a population lose sync with each other during the course of a CRT process, for example due to a defect in removal of a blocking group, leading to failure to incorporate an additional moiety during one or more cycles of a CRT process. Phasing can manifest as extension of one or more primer molecules 'falling behind' the others in the population, or alternately as a defect leading to one or more primer molecules 'going ahead' of others in the population. A phasing rate of, for example, only 0.5% per cycle may result in an accumulated loss of roughly half of true signal for a sequencing or other CRT reaction after 120 cycles. The problem is exacerbated by the proportional increase in background noise due to false signals that arise from members of the population that are out of phase. The accumulated loss in signal-to-noise results in a limitation on read length (which, in turn, results in reduced sequencing throughput) and increased errors especially for later cycles as noise overwhelms signal. The reversibly terminated nucleotides set forth herein can be used to inhibit disruptions in extension phase, thereby improving accuracy and read length reactions such as in nucleic acid sequencing processes. Through practice of the methods and use of the compositions disclosed herein, nucleotide compositions are generated having a very high degree of replacement of a protecting group such as —O-oxime by a reversible group such as an —O—$NH_2$, with a low rate of dC degradation, as depicted in FIG. 1A and as is applicable generally to the R2 moieties disclosed herein. Consequently, reagents generated using the compositions herein or through the methods disclosed herein are in some cases suitable for addition into a nucleic acid sequencing reagent, such as direct addition without further clean-up or purification, to produce a sequencing reaction run having a high degree of accuracy over a substantial length of a run, as depicted in Example 2, below. Such a reagent may further comprise a polymerase surfactant, buffer or other reagent suitable for direct addition into a sequencing device. Without being bound to theory, the performance of a run such as that presented in Example 2 is at least in part due to decreases in phasing defects which may otherwise result from inefficient replacement of a protecting group such as an —O-oxime group with a reversible terminator such as —O—$NH_2$, resulting in either retained protecting groups, unblocked 3' OH moieties, or degraded dC bases along the lines of those presented in FIG. 3.

Without being bound by theory, one possible advantage of the synthetic methods and compositions set forth herein for blocking the 3' position of a nucleotide is that the methods are relatively inert to unwanted side reactions with other moieties of the nucleotide. Accordingly, reversibly terminated nucleotides that are made by methods or involving the compositions set forth herein may not be substantially destroyed or modified in ways that carry over into adverse effects during blocking and deblocking steps that occur during a CRT process or other biochemical process that utilizes the reversibly terminated nucleotides. In various cases, no more than 6%, no more than 5%, no more than 4%, no more than 3%, no more than 2%, no more than 1% or less than 1% of the nucleotides, such as cytosine nucleotides, used in a reaction or represented in a composition herein are modified or degraded through the practice of the disclosure. Accordingly, the methods and compositions set forth herein provide improved sequencing accuracy by providing a sequencing starting material that is relatively free of degraded or modified bases such as degraded or modified cytosine that may interfere with the accuracy, phase or read length of a sequencing reaction. Similarly, the methods and compositions set forth herein facilitate the production of nucleic acid sequencing reagents by generating reversibly terminated nucleotides of a purity that can be, in some cases, directly added to a sequencing reagent without further purification or isolation.

Accordingly, compositions as disclosed herein or produced through methods disclosed herein facilitate accurate sequencing by being or by generating reversibly terminated nucleotides that are relatively clear of degraded or modified bases such as degraded or modified cytosine bases, while being relatively clear of retained 3' protecting groups such as —O-oximes, and having a relatively low concentration of unblocked 3' OH groups. These features, alone or in combination, facilitate sequencing accuracy, phasing or read length of a sequencing reaction. In addition, the higher efficiency of methods and purity of compositions resulting from these methods facilitates more cost-effective sequencing because the compositions require less purification prior to their employment in sequencing reactions, and are in some cases added directly into a sequencing reagent or kit without further isolation or purification.

Definitions

Terms used herein will be understood to take on their ordinary meaning in the relevant art unless specified otherwise. Several terms used herein and their meanings are set forth below.

Where substituent groups are specified by their conventional chemical formulae, written from left to right, they equally encompass the chemically identical substituents that would result from writing the structure from right to left, e.g., —$CH_2O$— is equivalent to —$OCH_2$—. Where a substituent group or moiety is written with internal bonds depicted, it will be understood that the substituent group or moiety may also be depicted without internal bonds explicitly drawn and both representation will be understood to be the same substituent group or moiety, for example —$ONH_2$ and —O—$NH_2$ are the same group.

As used herein, "alkenyl" refers to an alkyl that contains in the straight or branched hydrocarbon chain one or more double bonds. An alkenyl moiety may be unsubstituted or substituted. An alkenyl moiety can, optionally, have a number of carbon atoms that is in a range exemplified herein for alkyl moieties.

As used herein, "alkoxy" refers to the formula —OR wherein R is an alkyl, an alkenyl, an alkynyl, a cycloalkyl, a cycloalkenyl or a cycloalkynyl. A non-limiting list of alkoxys is methoxy, ethoxy, n-propoxy, 1-methylethoxy (isopropoxy), n-butoxy, iso-butoxy, sec-butoxy, or tert-butoxy. An alkoxy moiety may be substituted or unsubstituted.

As used herein, "alkoxyamine" refers to the formula R'—$ONR_2$ wherein R' is an alkyl, an alkenyl, an alkynyl, a cycloalkyl, a cycloalkenyl or a cycloalkynyl. A non-limiting list of alkoxys is methoxy, ethoxy, n-propoxy, 1-methylethoxy (isopropoxy), n-butoxy, iso-butoxy, sec-butoxy, or tert-butoxy, wherein R' is not hydrogen, and wherein one or both R groups that are bonded to nitrogen is independently a hydrogen, an alkyl, an alkenyl, an alkynyl, a cycloalkyl, a cycloalkenyl or a cycloalkynyl. A non-limiting list of alkoxys is methoxy, ethoxy, n-propoxy, 1-methylethoxy (isopropoxy), n-butoxy, iso-butoxy, sec-butoxy, or tert-butoxy. An alkoxyamine moiety may be substituted or unsubstituted.

As used herein, "alkyl" refers to a straight or branched hydrocarbon chain that comprises a fully saturated (no double or triple bonds) hydrocarbon moiety. Alkyl is an uncyclized chain. In some embodiments, the alkyl moiety may have 1 to 20 carbon atoms (whenever it appears herein, a numerical range such as "1 to 20" refers to each integer in the given range inclusive of the endpoints; e.g., "1 to 20 carbon atoms" means that the alkyl moiety may consist of 1 carbon atom, 2 carbon atoms, 3 carbon atoms, etc., up to and including 20 carbon atoms, although the present definition also covers the occurrence of the term "alkyl" where no numerical range is designated). The alkyl moiety may also be a medium size alkyl having about 7 to about 10 carbon atoms. The alkyl moiety can also be a lower alkyl having 1 to 6 carbon atoms. The alkyl moiety of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl moieties include, but are in no way limited to, methyl, ethyl, propyl, isopropyl, butyl, isobutyl, tertiary butyl, pentyl, and hexyls. The alkyl moiety may be substituted or unsubstituted. An alkyl moiety having at least two carbon atoms can be particularly useful, for example, when a methyl moiety is less effective than a longer chain alkyl moiety.

As used herein, "alkynyl" refers to an alkyl that contains in the straight or branched hydrocarbon chain one or more triple bonds. An alkynyl moiety may be unsubstituted or substituted. An alkynyl moiety can, optionally, have a number of carbon atoms that is in a range exemplified herein for alkyl moieties.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the carbon-carbon bonds of a heteroalkyl may be fully saturated (no double or triple carbon-carbon bonds).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne.

As used herein, "amine" refers to a —NR$_2$ moiety wherein one or more R group can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. In embodiments, each R group is independently substituted or unsubstituted.

As used herein, "aminooxy" refers to —O—NR$_2$ moiety, wherein one or more R group can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. In embodiments, each R group is independently substituted or unsubstituted.

As used herein, "array" refers to a population of molecules attached to one or more solid support such that the molecules at one site can be distinguished from molecules at other sites. An array can include different molecules that are each located at different addressable sites on a solid support. Alternatively, an array can include separate solid supports each functioning as a site that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acids, nucleic acid primers, nucleic acid templates, primed template nucleic acids, or nucleic acid enzymes such as polymerases, ligases, exonucleases or combinations thereof.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl moiety can vary. For example, in some embodiments, the aryl moiety can be a $C_6$-$C_{14}$ aryl moiety, a $C_6$-$C_{10}$ aryl moiety, or a $C_6$ moiety. Examples of aryl moieties include, but are not limited to, benzene, naphthalene, and azulene. An aryl moiety may be substituted or unsubstituted. In various embodiments, an aryl moiety is independently a phenyl or naphthyl. In embodiments, a fused ring aryl refers to multiple rings fused together wherein at least one of the fused rings is an aryl ring and wherein the multiple rings are attached to the parent molecular moiety through any carbon atom contained within an aryl ring of the multiple rings. An "arylene", alone or as part of another substituent, means a divalent radical derived from an aryl.

As used herein, "aralkyl" and "aryl(alkyl)" refer to an aryl connected, as a substituent, via a lower alkylene moiety. The lower alkylene and aryl moiety of an aralkyl may be substituted or unsubstituted. Examples include but are not limited to benzyl, 2-phenylalkyl, 3-phenylalkyl, and naphthylalkyl.

As used herein, "attached" refers to the state of two things being joined, fastened, adhered, connected or bound to each other. For example, a nucleic acid can be attached to a solid phase support by a covalent or non-covalent bond. Similarly, two nucleic acids can be attached to each other by a covalent (e.g. phosphodiester) bond or by a non-covalent bond (e.g. hydrogen bonding between bases of the two nucleic acids). A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, "blocking moiety," when used in reference to a nucleotide, means a part of the nucleotide that inhibits or prevents the 3' oxygen of the nucleotide from forming a covalent linkage to another nucleotide or to an oligonucleotide. For example, a blocking moiety can inhibit or prevent polymerase catalyzed formation of a covalent linkage between the 3' position of the nucleotide and a next correct nucleotide during a nucleic acid polymerization reaction. Similarly, a blocking moiety can inhibit or prevent ligase catalyzed formation of a covalent linkage between the 3' position of the nucleotide and an oligonucleotide during a nucleic acid ligation reaction. Notably, blocking moieties as contemplated herein do not interfere with incorporation of the blocked base into an extending primer strand (e.g., catalyzed by a polymerase); rather, once incorporated, a blocked nucleotide interferes with subsequent elongation because the 3' end of the nucleotide is inaccessible to the 5' phosphate of a subsequent nucleotide. The blocking moiety of a "reversibly terminated" nucleotide can be removed from the nucleotide analog, or otherwise modified, without substantial harm to the extending primer strand or its complement, to allow the 3'-oxygen of the nucleotide to be available to covalently link to another nucleotide or to an oligonucleotide. Such a blocking moiety may be referred to herein as a "reversible terminator moiety" because the blocking of primer extension is reversed through removal of the blocking or terminator moiety. A nucleotide that has a blocking moiety such as a reversible terminator moiety can be at the 3' end of a nucleic acid, such as a primer, or can be a monomeric molecule that is not covalently attached to a nucleic acid. Exemplary blocking moieties include 3' $ONH_2$, as well as 3' $ONHCH_3$ and 3' O methylazide (3'-$OCH_2N_3$). In various embodiments, a protecting moiety may also be a blocking moiety (e.g., a 3'-O-oxime moiety may be a blocking moiety). As used herein, R2-block is R2 bonded to a blocking moiety such as a reversible terminator moiety. R2-moieties in solution are in some cases used to stabilize blocking moieties so as to prevent their unwanted removal from nucleotides to form 3' OH groups compatible with polymerase-mediated extension.

As used herein, a "protecting moiety" is a moiety that protects a molecule to which it is attached from cross-reaction or misdirected reaction during a chemical process, such as a nonenzymatic process or a nonspecific chemical process. Unlike blocking moieties such as reversible terminating moieties, protecting moieties are not necessarily readily removed without risk of cross-reaction or degradation to the protected molecule. Exemplary moieties include 3'-O-oxime moieties such as 3'-O-alkoximes or 3' O-ketoximes, which protect ribose 3' positions from cross reaction during 5' phosphorylation reactions, for example. In various embodiments, a protecting moiety is a 3'-O-oxime (e.g., 3'-O-alkoxime or 3'-O-ketoxime). In embodiments, the protecting moiety prevents reactivity of the 3' carbon or 3' oxygen of a nucleotide or nucleoside during a phosphorylation reaction of the nucleotide or nucleoside, such as may occur during the addition of a triphosphate moiety to a nucleotide 5' position.

The term "comprising" is intended herein to be open-ended, including recited elements, but also leaving open the possibility of including additional, unrecited elements.

As used herein, "cycloalkyl" refers to a completely saturated (no double or triple bonds) mono- or multi-cyclic hydrocarbon ring system. When composed of two or more rings, the rings may be joined together in a fused fashion. A cycloalkyl moiety can contain 3 to 10 atoms in the ring(s). In some molecules, a cycloalkyl moiety can contain 3 to 8 atoms in the ring(s). A cycloalkyl moiety may be unsubstituted or substituted. Typical cycloalkyl moieties include, but are not limited to, cyclopropyl, cyclobutyl, cyclopentyl, cyclohexyl, cycloheptyl, and cyclooctyl.

As used herein, "cycloalkenyl" refers to a mono- or multi-cyclic hydrocarbon ring system that contains one or more double bonds in at least one ring; although, if there is more than one, the double bonds do not form a fully delocalized pi-electron system throughout all the rings (otherwise the moiety would be "aryl," as defined herein). When composed of two or more rings, the rings may be connected together in a fused fashion. A cycloalkenyl moiety may be unsubstituted or substituted. A "cycloalkylene", alone or as part of another substituent, means a divalent radical derived from a cycloalkyl.

As used herein, "cycloalkynyl" refers to a mono- or multi-cyclic hydrocarbon ring system that contains one or more triple bonds in at least one ring. If there is more than one triple bond, the triple bonds do not form a fully delocalized pi-electron system throughout all the rings. When composed of two or more rings, the rings may be joined together in a fused fashion. A cycloalkynyl moiety may be unsubstituted or substituted.

As used herein, "deblock" means to remove or modify a blocking moiety such as a reversible terminator moiety of a nucleotide to render the nucleotide extendable, such as through exposure of or generation of a 3' OH. Such a deblocked nucleotide or nucleic acid strand is capable of forming a phosphodiester bond with a second nucleotide, rendering the nucleotide capable of forming a phosphodiester bond involving the 3' carbon of the nucleotide and the 5' carbon of a second nucleotide). For example, a reversibly terminated nucleotide can be present at the 3' end of a primer such that deblocking renders the primer extendable. Alternatively, the nucleotide can be in monomeric form when deblocked.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the phrase "at least one element selected from the list of" A, B, and C is intended to read on sets including one element from the list, two elements form the list or all elements of the list, and may but is not necessarily intended to require a representative of each element A, B, and C unless otherwise designated.

As used herein, "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous linker that is present on a nucleic acid is not found on nucleic acids in their native milieu.

As used herein, "extension," when used in reference to a nucleic acid, means a process of adding at least one nucleotide to the 3' end of the nucleic acid. The term "polymerase extension," when used in reference to a nucleic acid, refers to a polymerase catalyzed process of adding one or more individual nucleotides to the 3' end of the nucleic acid. The term "ligase extension," when used in reference to a nucleic acid, refers to a ligase catalyzed process of adding at least one oligonucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, "extendable," when used in reference to a nucleotide, means that the nucleotide has an oxygen or hydroxyl moiety at the 3' position, and is capable of forming a covalent linkage to a next correct nucleotide (or to an oligonucleotide) if and when incorporated into a nucleic acid. An extendable nucleotide can be at the 3' position of a primer or it can be a monomeric nucleotide. A nucleotide that is extendable will lack blocking moieties such as reversible terminator moieties, and a deblocked nucleotide or nucleic acid strand is often extendable.

As used herein, a "flow cell" is a vessel that includes one or more channels that direct fluid to a detection zone. The detection zone can be coupled to a detector such that a reaction occurring in the vessel can be observed. For example, a flow cell can contain primed template nucleic acid molecules tethered to a solid phase support, to which nucleotides and ancillary reagents are iteratively applied and washed away. The flow cell can include a transparent material that permits the sample to be imaged after a desired reaction occurs. For example, a flow cell can include a glass or plastic slide containing small fluidic channels through which polymerases, dNTPs and buffers can be flowed. The glass or plastic inside the channels can be decorated with one or more primed template nucleic acid molecules to be detected. An external imaging system can be positioned to detect the molecules at a detection zone. Exemplary flow cells, methods for their manufacture and methods for their use are described in US Pat. App. Publ. Nos. 2010/0111768 A1, published May 6, 2010 or 2012/0270305 A1, published Oct. 25, 2012; or WO 05/065814, published Jul. 25, 2005, each of which hereby is incorporated by reference in its entirety herein.

As used herein, "fluid" refers to a liquid or a gas, that is capable of flowing and that changes its shape to fill a vessel. In many conditions, a fluid will change shape at a steady rate when acted upon by a force tending to change its shape. An exemplary fluid is a fluid foam which is a liquid that contains bubbles of gas. Exemplary liquids that can be used, for example, in a fluid foam include those that contain reagents or products of a reaction such as a binding reaction, nucleic acid sequencing reaction or reaction used in an analytical assay. Aqueous liquids can be particularly useful. Exemplary gases include inert gases such as nitrogen ($N_2$) or noble gases. Useful noble gases include, for example, helium (He), neon (Ne), argon (Ar), krypton (Kr) and xenon (Xe). Another useful gas is atmospheric air of planet earth. Further examples of fluid foams and methods for making and using fluid foams are set forth in U.S. Pat. App. Ser. No. 62/883,276, which is incorporated herein by reference.

As used herein, "halogen atom", "halogen" or "halo" means any one of the radio-stable atoms of column 7 of the Periodic Table of the Elements, such as, fluorine, chlorine, bromine, and iodine. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

As used herein, "heterocyclyl" refers to a ring system including at least one heteroatom (e.g., O, N, S). Such systems can be unsaturated, can include some unsaturation, or can contain some aromatic portion, or be all aromatic. A heterocyclyl moiety may be unsubstituted or substituted.

As used herein, "heteroalicyclic" or "heteroalicyclyl" refers to three-, four-, five-, six-, seven-, eight-, nine-, ten-, or more up to 18-membered monocyclic, bicyclic, and tricyclic ring system wherein carbon atoms together with from 1 to 5 heteroatoms constitute the ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, and as such the definition includes oxo-systems and thio-systems such as lactams, lactones, cyclic imides, cyclic thioimides, and cyclic carbamates. When composed of two or more rings, the rings may be joined together in a fused fashion. Additionally, any nitrogens in a heteroalicyclic moiety may be quaternized. Heteroalicyclyl or heteroalicyclic moieties may be unsubstituted or substituted. Examples of such "heteroalicyclic" or "heteroalicyclyl" moieties include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl). In embodiments, a fused ring heteroalicyclyl refers to multiple rings fused together wherein at least one of the fused rings is a heteroalicyclyl ring and wherein the multiple rings are attached to the parent molecular moiety through any atom contained within a heteroalicyclyl ring of the multiple rings. A "heteroalicyclylene," alone or as part of another substituent, means a divalent radical derived from a heteroalicyclyl.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl moiety can vary. For example, in some embodiments, a heteroaryl moiety can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl moiety may be substituted or unsubstituted. In embodiments, the term "heteroaryl" includes fused ring heteroaryl groups wherein multiple rings are fused together and wherein at least one of the fused rings is a heteroaromatic ring and wherein the multiple rings are attached to the parent molecular moiety through any atom contained within a heteroaromatic ring of the multiple rings. A "heteroarylene," alone or as part of another substituent, means a divalent radical derived from a heteroaryl.

As used herein, "(heteroalicyclyl)alkyl" is a heterocyclic or a heteroalicyclic moiety connected, as a substituent, via a lower alkylene moiety. The lower alkylene and heterocyclic or a heterocyclyl of a (heteroalicyclyl)alkyl may be substituted or unsubstituted. Examples include but are not limited to tetrahydro-2H-pyran-4-yl)methyl, (piperidin-4-yl)ethyl, (piperidin-4-yl)propyl, (tetrahydro-2H-thiopyran-4-yl) methyl, and (1,3-thiazinan-4-yl)methyl.

As used herein, "heteroaralkyl" and "heteroaryl(alkyl)" refer to a heteroaryl connected, as a substituent, via a lower alkylene moiety. The lower alkylene and heteroaryl moiety of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

As used herein, "hydroxy" refers to a —OH moiety. Similarly, "hydroxylated" refers to a molecule to which —OH moieties have been added, for example to facilitate solubility.

As used herein, "label" refers to a molecule, or moiety thereof, that provides a detectable characteristic. The detectable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor, such as an antibody or streptavidin; magnetic properties; electrical properties; conductivity; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like.

As used herein, "linker" and "linker moiety" refer to an atom or moiety that joins two different entities. Typically, a linker will provide or comprise a covalent bond, or a series of covalent bonds, between the two entities. However, a linker can include non-covalent bonds such as those that form between a receptor and ligand. Exemplary entities that can be linked include, but are not limited to, a solid support, moiety (e.g. a nucleotide monomer of a nucleic acid or a base of a nucleotide) or molecule (e.g. a nucleic acid or label).

As used herein, "next correct nucleotide" refers to the nucleotide type that will bind and/or incorporate at the 3' end of a primer to complement a base in a template strand to which the primer is hybridized when correctly basepaired. The base in the template strand is referred to as the "next base" and is immediately 5' of the base in the template that is hybridized to the 3' end of the primer. The next correct nucleotide can be referred to as the "cognate" of the next base and vice versa. Cognate nucleotides that interact with each other in a ternary complex or in a double stranded nucleic acid are said to "pair" with each other. In accordance with Watson-Crick pairing rules adenine (A) pairs with thymine (T) or uracil (U), and guanine (G) pairs with cytosine (C) or uracil (U). A nucleotide having a base that is not complementary to the next template base is referred to as an "incorrect", "mismatch" or "non-cognate" nucleotide.

As used herein, "nucleobase" (also referred to as a "nitrogenous base" or a "base") refers to a purine or purine derivative or pyrimidine or pyrimidine derivative that forms the differentiating unit of a nucleotide. The five primary or canonical nucleobases are adenine (A), cytosine (C), guanine (G), thymine (T), and uracil (U). Adenine and guanine are purine bases. Cytosine, uracil, and thymine are pyrimidine bases. Each of the base pairs in a typical double-helix includes a purine and a pyrimidine: either an A paired with a T, an A paired with a U, or a G paired with a C or a G paired with a U. These purine-pyrimidine pairs, are referred to as 'base complements' or are said to be "complementary" to each other. Cytosine nucleobases, in particular, are subject to modification or degradation pursuant to replacing some protecting groups with blocking groups.

As used herein, "nucleic acid" refers to at least two nucleotides covalently linked together. Thus, an exemplary "nucleic acid" is a polynucleotide, such as DNA, RNA, or any combination thereof. Typical nucleic acids can be acted upon by a polymerase during nucleic acid synthesis or detection. The term "nucleic acid" includes single-, double-, or multiple-stranded DNA, RNA and analogs (derivatives) thereof.

As used herein, "nucleotide" can be used to refer to a native nucleotide or analog thereof. Generally, a nucleotide has three moieties: a nucleobase (e.g. purine or pyrimidine), a five-carbon sugar (e.g. ribose or deoxyribose), and at least one phosphate. Examples include, but are not limited to, nucleotide triphosphates (NTPs) such as ribonucleotide triphosphates (rNTPs), deoxyribonucleotide triphosphates (dNTPs), or non-natural analogs thereof such as dideoxyribonucleotide triphosphates (ddNTPs) or reversibly terminated nucleotide triphosphates (rtNTPs). A nucleotide can be in a monomeric form, for example, as a nucleotide triphosphate, nucleotide diphosphate or nucleotide monophosphate. A nucleotide can also be a moiety of a nucleic acid polymer, for example, being identified according to its position in the polymer such as the 3' nucleotide (i.e. the nucleotide moiety that is present at the 3' end of the polymer) or the 5' nucleotide (i.e. the nucleotide moiety that is present at the 5' end of the polymer). A nucleoside contains a nucleobase and a 5-carbon sugar. Thus, a nucleotide is a nucleoside having a phosphate moiety.

As used herein, "optionally substituted," when used in reference to a moiety of a molecule, means that the moiety may be unsubstituted or substituted with one or more of the indicated substituents. Likewise, when a moiety is described as being "substituted or unsubstituted" or "unsubstituted or substituted," the substituent may be selected from one or more the indicated substituents. If no substituents are indicated, it is meant that the indicated "optionally substituted" or "substituted" moiety may be individually and independently substituted with one or more moieties individually and independently selected from a group of functionalities including, but not limited to, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group, di-substituted amino group, and protected derivatives thereof. If no substituents are indicated in reference to an "unsubstituted" moiety, the omitted moiety(ies) may individually and independently be selected from a group of functionalities including, but not limited to, those set forth in the previous sentence or elsewhere herein.

Each of the above terms (e.g., "alkyl," "alkenyl," "alkynyl," "heteroalkyl," "cycloalkyl," "cycloalkenyl," "cycloalkynyl," "heteroalicyclyl," "aryl," "heteroaryl", "alkylene," "alkenylene," "alkynylene," "heteroalkylene," "cycloalkylene," "cycloalkenylene," "cycloalkynylene," "heteroalicyclylene," "arylene," and "heteroarylene") includes both substituted and unsubstituted forms of the indicated radical. Preferred substituents for each type of radical are provided below.

Substituents for the alkyl and heteroalkyl radicals can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'C(O) NR"R'", —NR"C(O)$_2$R', —NRC(NR'R"R'")=NR"", —NRC(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)OR", —NR'OR", —N$_3$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heteroalicyclyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'C(O) NR"R'", —NR"C(O)$_2$R', —NRC(NR'R"R'")=NR"", —NRC(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, cycloalkenyl, cycloalkynyl, heteroalicyclyl, aryl, or heteroaryl) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, cycloalkenyl, cycloalkynyl, or heteroalicyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), selenium (Se), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted alkenyl (e.g., C$_2$-C$_8$ alkenyl, C$_2$-C$_6$ alkenyl, or C$_2$-C$_4$ alkenyl), unsubstituted alkynyl (e.g., C$_2$-C$_8$ alkynyl, C$_2$-C$_6$ alkynyl, or C$_2$-C$_4$ alkynyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted cycloalkenyl (e.g., C$_3$-C$_8$ cycloalkenyl, C$_3$-C$_6$ cycloalkenyl, or C$_5$-C$_6$ cycloalkenyl), unsubstituted cycloalkynyl (e.g., C$_3$-C$_8$ cycloalkynyl, C$_3$-C$_6$ cycloalkynyl, or C$_5$-C$_6$ cycloalkynyl), unsubstituted heteroalicyclyl (e.g., 3 to 8 membered heteroalicyclyl, 3 to 6 membered heteroalicyclyl, or 5 to 6 membered heteroalicyclyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_{20}$, C$_1$-C$_{12}$, C$_1$-C$_8$, C$_1$-C$_6$, C$_1$-C$_4$, or C$_1$-C$_2$), alkenyl (e.g., C$_2$-C$_{20}$, C$_2$-C$_{12}$, C$_2$-C$_8$, C$_2$-C$_6$, or C$_2$-C$_4$), alkynyl (e.g., C$_2$-C$_{20}$, C$_2$-C$_{12}$, C$_2$-C$_8$, C$_2$-C$_6$, or C$_2$-C$_4$), heteroalkyl (e.g., 2 to 20 membered, 2 to 12 membered, 2 to 8 membered, 2 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), cycloalkenyl (e.g., C$_3$-C$_{10}$, C$_3$-C$_8$, C$_3$-C$_6$, C$_4$-C$_6$, or C$_5$-C$_6$), cycloalkynyl (e.g., C$_3$-C$_{10}$, C$_3$-C$_8$, C$_3$-C$_6$, C$_4$-C$_6$, or C$_5$-C$_6$), heteroalicyclyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted alkenyl (e.g., C$_2$-C$_8$ alkenyl, C$_2$-C$_6$ alkenyl, or C$_2$-C$_4$ alkenyl), unsubstituted alkynyl (e.g., C$_2$-C$_8$ alkynyl, C$_2$-C$_6$ alkynyl, or C$_2$-C$_4$ alkynyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted cycloalkenyl (e.g., C$_3$-C$_8$ cycloalkenyl, C$_3$-C$_6$ cycloalkenyl, or C$_5$-C$_6$ cycloalkenyl), unsubstituted cycloalkynyl (e.g., C$_3$-C$_8$ cycloalkynyl, C$_3$-C$_6$ cycloalkynyl, or C$_5$-C$_6$ cycloalkynyl), unsubstituted heteroalicyclyl (e.g., 3 to 8 membered heteroalicyclyl, 3 to 6 membered heteroalicyclyl, or to 6 membered het- (ii) alkyl (e.g., C$_1$-C$_{20}$, C$_1$-C$_{12}$, C$_1$-C$_8$, C$_1$-C$_6$, C$_1$-C$_4$, or C$_1$-C$_2$), alkenyl (e.g., C$_2$-C$_{20}$, C$_2$-C$_{12}$, C$_2$-C$_8$, C$_2$-C$_6$, or C$_2$-C$_4$), alkynyl (e.g., C$_2$-C$_{20}$, C$_2$-C$_{12}$, C$_2$-C$_8$, C$_2$-C$_6$, or C$_2$-C$_4$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), cycloalkenyl (e.g., C$_3$-C$_{10}$, C$_3$-C$_8$, C$_3$-C$_6$, C$_4$-C$_6$, or C$_5$-C$_6$), cycloalkynyl (e.g., C$_3$-C$_{10}$, C$_3$-C$_8$, C$_3$-C$_6$, C$_4$-C$_6$, or C$_5$-C$_6$), heteroalicyclyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted alkenyl (e.g., C$_2$-C$_8$ alkenyl, C$_2$-C$_6$ alkenyl, or C$_2$-C$_4$ alkenyl), unsubstituted alkynyl (e.g., C$_2$-C$_8$ alkynyl, C$_2$-C$_6$ alkynyl, or C$_2$-C$_4$ alkynyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted cycloalkenyl (e.g., C$_3$-C$_8$ cycloalkenyl, C$_3$-C$_6$ cycloalkenyl, or C$_5$-C$_6$ cycloalkenyl), unsubstituted cycloalkynyl (e.g., C$_3$-C$_8$ cycloalkynyl, C$_3$-C$_6$ cycloalkynyl, or C$_5$-C$_6$ cycloalkynyl), unsubstituted heteroalicyclyl (e.g., 3 to 8 membered heteroalicyclyl, 3 to 6 membered heteroalicyclyl, or to 6 membered heteroalicyclyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_{20}$, $C_1$-$C_{12}$, $C_1$-$C_8$, $C_1$-$C_6$, $C_1$-$C_4$, or $C_1$-$C_2$), alkenyl (e.g., $C_2$-$C_{20}$, $C_2$-$C_{12}$, $C_2$-$C_8$, $C_2$-$C_6$, or $C_2$-$C_4$), alkynyl (e.g., $C_2$-$C_{20}$, $C_2$-$C_{12}$, $C_2$-$C_8$, $C_2$-$C_6$, or $C_2$-$C_4$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), cycloalkenyl (e.g., $C_3$-$C_{10}$, $C_3$-$C_8$, $C_3$-$C_6$, $C_4$-$C_6$, or $C_5$-$C_6$), cycloalkynyl (e.g., $C_3$-$C_{10}$, $C_3$-$C_8$, $C_3$-$C_6$, $C_4$-$C_6$, or $C_5$-$C_6$), heteroalicyclyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, unsubstituted alkyl (e.g., $C_1$-$C_8$ alkyl, $C_1$-$C_6$ alkyl, or $C_1$-$C_4$ alkyl), unsubstituted alkenyl (e.g., $C_2$-$C_8$ alkenyl, $C_2$-$C_6$ alkenyl, or $C_2$-$C_4$ alkenyl), unsubstituted alkynyl (e.g., $C_2$-$C_8$ alkynyl, $C_2$-$C_6$ alkynyl, or $C_2$-$C_4$ alkynyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted cycloalkenyl (e.g., $C_3$-$C_8$ cycloalkenyl, $C_3$-$C_6$ cycloalkenyl, or $C_5$-$C_6$ cycloalkenyl), unsubstituted cycloalkynyl (e.g., $C_3$-$C_8$ cycloalkynyl, $C_3$-$C_6$ cycloalkynyl, or $C_5$-$C_6$ cycloalkynyl), unsubstituted heteroalicyclyl (e.g., 3 to 8 membered heteroalicyclyl, 3 to 6 membered heteroalicyclyl, or to 6 membered heteroalicyclyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted alkenyl is a substituted or unsubstituted $C_2$-$C_{20}$ alkenyl, each substituted or unsubstituted alkynyl is a substituted or unsubstituted $C_2$-$C_{20}$ alkynyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted cycloalkenyl is a substituted or unsubstituted $C_3$-$C_8$ cycloalkenyl, each substituted or unsubstituted cycloalkynyl is a substituted or unsubstituted $C_3$-$C_8$ cycloalkynyl, each substituted or unsubstituted heteroalicyclyl is a substituted or unsubstituted 3 to 8 membered heteroalicyclyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted alkenyl is a substituted or unsubstituted $C_2$-$C_8$ alkenyl, each substituted or unsubstituted alkynyl is a substituted or unsubstituted $C_2$-$C_8$ alkynyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted cycloalkenyl is a substituted or unsubstituted $C_3$-$C_7$ cycloalkenyl, each substituted or unsubstituted cycloalkynyl is a substituted or unsubstituted $C_3$-$C_7$ cycloalkynyl, each substituted or unsubstituted heteroalicyclyl is a substituted or unsubstituted 3 to 7 membered heteroalicyclyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted alkenyl, substituted alkynyl, substituted heteroalkyl, substituted cycloalkyl, substituted cycloalkenyl, substituted cycloalkynyl, substituted heteroalicyclyl, substituted aryl, substituted heteroaryl, substituted alkylene, substituted heteroalkylene, substituted cycloalkylene, substituted heteroalicyclylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted alkenyl may be a substituted or unsubstituted $C_2$-$C_{20}$ alkenyl, each substituted or unsubstituted alkynyl may be a substituted or unsubstituted $C_2$-$C_{20}$ alkynyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted cycloalkenyl is a substituted or unsubstituted $C_3$-$C_8$ cycloalkenyl, each substituted or unsubstituted cycloalkynyl is a substituted or unsubstituted $C_3$-$C_8$ cycloalkynyl, each substituted or unsubstituted heteroalicyclyl is a substituted or unsubstituted 3 to 8 membered heteroalicyclyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted alkenylene is a substituted or unsubstituted $C_2$-$C_{20}$ alkenylene, each substituted or unsubstituted alkynylene is a substituted or unsubstituted $C_2$-$C_{20}$ alkynylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted cycloalkenylene is a substituted or unsubstituted $C_3$-$C_8$ cycloalkenylene, each substituted or unsubstituted cycloalkynylene is a substituted or unsubstituted $C_3$-$C_8$ cycloalkynylene, each substituted or unsubstituted heteroalicyclylene is a substituted or unsubstituted 3 to 8 membered heteroalicyclylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted alkenyl is a substituted or unsubstituted $C_2$-$C_8$ alkenyl, each substituted or unsubstituted alkynyl is a substituted or unsubstituted $C_2$-$C_8$ alkynyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted cycloalkenyl is a substituted or unsubstituted $C_3$-$C_7$ cycloalkenyl, each substituted or unsubstituted cycloalkynyl is a substituted or unsubstituted $C_3$-$C_7$ cycloalkynyl, each substituted or unsubstituted heteroalicyclyl is a substituted or unsubstituted 3 to 7 membered heteroalicyclyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted alkenylene is a substituted or unsubstituted $C_2$-$C_8$ alkenylene, each substituted or unsubstituted alkynylene is a substituted or unsubstituted $C_2$-$C_8$ alkynylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted cycloalkenylene is a substituted or unsubstituted $C_3$-$C_7$ cycloalkenylene, each substituted or unsubstituted cycloalkynylene is a substituted or unsubstituted $C_3$-$C_7$ cycloalkynylene, each substituted or unsubstituted heteroalicyclylene is a substituted or unsubstituted 3 to 7 membered heteroalicyclylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the application (e.g., Examples section, figures, or tables below).

In embodiments, a substituted or unsubstituted moiety (e.g., substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted cycloalkenylene, substituted or unsubstituted cycloalkynylene, substituted or unsubstituted heteroalicyclylene, substituted or unsubstituted arylene, and/or substituted or unsubstituted heteroarylene) is unsubstituted (e.g., is an unsubstituted alkyl, unsubstituted alkenyl, unsubstituted alkynyl, unsubstituted heteroalkyl, unsubstituted cycloalkyl, unsubstituted cycloalkenyl, unsubstituted cycloalkynyl, unsubstituted heteroalicyclyl, unsubstituted aryl, unsubstituted heteroaryl, unsubstituted alkylene, unsubstituted alkenylene, unsubstituted alkynylene, unsubstituted heteroalkylene, unsubstituted cycloalkylene, unsubstituted cycloalkenylene, unsubstituted cycloalkynylene, unsubstituted heteroalicyclylene, unsubstituted arylene, and/or unsubstituted heteroarylene, respectively). In embodiments, a substituted or unsubstituted moiety (e.g., substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl, substituted or unsubstituted alkylene, substituted or unsubstituted alkenylene, substituted or unsubstituted alkynylene, substituted or unsubstituted heteroalkylene, substituted or unsubstituted cycloalkylene, substituted or unsubstituted cycloalkenylene, substituted or unsubstituted cycloalkynylene, substituted or unsubstituted heteroalicyclylene, substituted or unsubstituted arylene, and/or substituted or unsubstituted heteroarylene) is substituted (e.g., is a substituted alkyl, substituted alkenyl, substituted alkynyl, substituted heteroalkyl, substituted cycloalkyl, substituted cycloalkenyl, substituted cycloalkynyl, substituted heteroalicyclyl, substituted aryl, substituted heteroaryl, substituted alkylene, substituted alkenylene, substituted alkynylene, substituted heteroalkylene, substituted cycloalkylene, substituted cycloalkenylene, substituted cycloalkynylene, substituted heteroalicyclylene, substituted arylene, and/or substituted heteroarylene, respectively).

In embodiments, a substituted moiety (e.g., substituted alkyl, substituted alkenyl, substituted alkynyl, substituted heteroalkyl, substituted cycloalkyl, substituted cycloalkenyl, substituted cycloalkynyl, substituted heteroalicyclyl, substituted aryl, substituted heteroaryl, substituted alkylene, substituted alkenylene, substituted alkynylene, substituted heteroalkylene, substituted cycloalkylene, substituted cycloalkenylene, substituted cycloalkynylene, substituted heteroalicyclylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted alkenyl, substituted alkynyl, substituted heteroalkyl, substituted cycloalkyl, substituted cycloalkenyl, substituted cycloalkynyl, substituted heteroalicyclyl, substituted aryl, substituted heteroaryl, substituted alkylene, substituted alkenylene, substituted alkynylene, substituted heteroalkylene, substituted cycloalkylene, substituted cycloalkenylene, substituted cycloalkynylene, substituted heteroalicyclylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted alkenyl, substituted alkynyl, substituted heteroalkyl, substituted cycloalkyl, substituted cycloalkenyl, substituted cycloalkynyl, substituted heteroalicyclyl, substituted aryl, substituted heteroaryl, substituted alkylene, substituted alkenylene, substituted alkynylene, substituted heteroalkylene, substituted cycloalkylene, substituted cycloalkenylene, substituted cycloalkynylene, substituted heteroalicyclylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted alkenyl, substituted alkynyl, substituted heteroalkyl, substituted cycloalkyl, substituted cycloalkenyl, substituted cycloalkynyl, substituted heteroalicyclyl, substituted aryl, substituted heteroaryl, substituted alkylene, substituted alkenylene, substituted alkynylene, substituted heteroalkylene, substituted cycloalkylene, substituted cycloalkenylene, substituted cycloalkynylene, substituted heteroalicyclylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an", as used in herein means one or more. In addition, the phrase "substituted with a[n]", as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl", the group may contain one or more unsubstituted $C_1$-$C_{20}$ alkyls, and/or one or more unsubstituted 2 to 20 membered heteroalkyls.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

In this disclosure, "comprises", "comprising", "containing", and "having" and the like can have the meaning ascribed to them in U.S. Patent law and can mean "includes", "including", and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a substance, element, compound, or composition; or moiety thereof, detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g., fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Ph, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, and $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb, and Lu.

The terms "polypeptide", "peptide", and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, "oxime" refers to a moiety having the following structure:

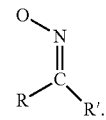

The oxime moiety can be attached to another moiety via the oxygen atom in which case the moiety can be referred to as an "O-oxime" moiety. An aldoxime moiety will have a hydrogen at one of R or R'. A ketoxime will have hydrogen at neither R nor R'. Oximes are exemplary protecting groups in some embodiments disclosed herein. A 3'-O-oxime is an oxime moiety attached to the 3' carbon of a nucleotide or nucleoside through the oxime oxygen.

As used herein, "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase can catalyze the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, "primed template nucleic acid" or "primed template" refers to a nucleic acid having a double stranded region such that one of the strands is a primer and the other strand is a template. The two strands can be parts of a contiguous nucleic acid molecule (e.g. a hairpin structure) or the two strands can be separable molecules that are not covalently attached to each other.

As used herein, "primer" refers to a nucleic acid having a sequence that binds to a nucleic acid at or near a template sequence. In particular configurations, the primer binds in a configuration that allows replication of the template, for example, via polymerase extension of the primer or ligase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof. A primer can have an extendible 3' end or a 3' end that is blocked, such as reversibly terminated, so as to preclude primer extension until removal of the blocking moiety.

As used herein, "site," when used in reference to an array, means a location in an array where a particular molecule is present. A site can contain only a single molecule or it can contain a population of several molecules of the same species (e.g. an ensemble of the molecules). Alternatively, a site can include a population of molecules that are different species (e.g. a population of different template sequences). Sites of an array are typically discrete. The discrete sites can be contiguous or they can have spaces between each other. An array useful herein can have, for example, sites that are separated by less than 100 microns, 50 microns, 10 microns, 5 microns, 1 micron, or 0.5 micron. Alternatively or additionally, an array can have sites that are separated by greater than 0.5 micron, 1 micron, 5 microns, 10 microns, 50 microns or 100 microns. The sites can each have an area of less than 1 square millimeter, 500 square microns, 100 square microns, 25 square microns, 1 square micron or less. The density of sites of sites in an array can be, for example, at least about 10 sites/cm$^2$, 100 sites/cm$^2$, 1×10$^3$ sites/cm$^2$, 1×10$^4$ sites/cm$^2$, 1×10$^5$ sites/cm$^2$, 1×10$^6$ sites/cm$^2$, or higher.

As used herein, "solid support" or "solid phase support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "surface" refers to a portion of a solid support that contacts a fluid. The fluid can be gas or liquid. The surface can be substantially flat or planar. Alternatively, the surface can be rounded or contoured. Exemplary contours that can be included on a surface are wells, depressions, pillars, ridges, channels or the like. Exemplary materials that can be used as a solid support include, but are not limited to, those set forth above.

As used herein, "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, "type" is used to identify molecules that share the same chemical structure. For example, a mixture of nucleotides can include several dCTP molecules. The dCTP molecules will be understood to be the same type of nucleotide as each other, but a different type of nucleotide compared to dATP, dGTP, dTTP etc. Similarly, individual DNA molecules that have the same sequence of nucleotides are the same type, whereas DNA molecules with different sequences are different types. The term "type" can also identify moieties that share the same chemical structure. For example, the cytosine bases in a template nucleic acid will be understood to be the same type of base as each other independent of their position in the template sequence.

As used herein, a "vessel" is a container that functions to isolate one chemical process (e.g., a binding event; an incorporation reaction; addition of a nucleotide to an extending chain, removal of a reversible terminator from a 3' end of a blocked nucleotide or extending primer; or replacement of a protecting moiety by a blocking moiety; or other reaction such as a reaction involving nucleic acid chemistry) from another, or to provide a space in which a chemical process can take place. Non-limiting examples of vessels useful in connection with the disclosed technique include: flow cells, wells of a multi-well plate; microscope slides; tubes (e.g., capillary tubes); droplets, vesicles, test tubes, trays, centrifuge tubes, features in an array, tubing, channels in a substrate or other volumes used in nucleic acid chemistry. As used herein, a "manufactured vessel" is a container that is human-made or human-modified and that functions to isolate one chemical process (e.g., a binding event; an incorporation reaction; addition or removal of a protecting moiety, addition or removal of a blocking moiety such as a reversible terminator) from another, or to provide a space in which a chemical process can take place.

Figure 3:
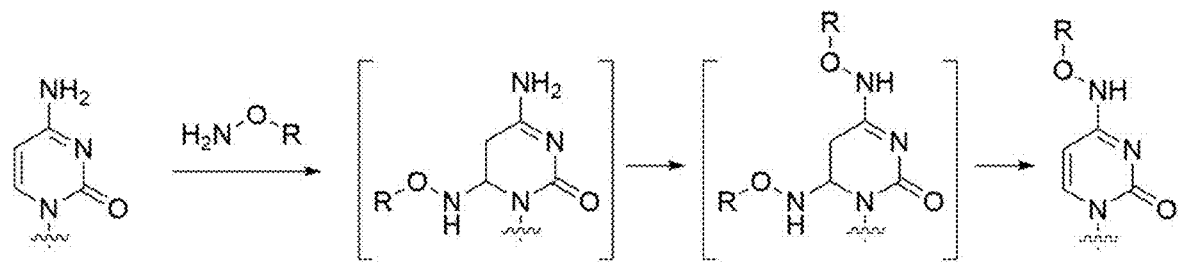
FIG. 3. Example of a deblocking side reaction with cytidine. This side reaction accounts for at least some of the dC degradation quantified in FIG. 1A. As indicated in FIG. 1A, with increasing R2 size one sees an decrease in the side reaction depicted herein.

As used herein, the terms "degrade" and "degradation", when referring to a nucleotide, or a portion of the nucleotide, mean chemical modification of the nucleotide, or a portion of the nucleotide, resulting in a different molecule having at least one modulated function or activity relative to the original (i.e., undegraded) nucleotide, or portion of the nucleotide. In some embodiments the terms "degrade" and "degradation", when referring to a nucleobase, mean chemical modification of the nucleobase resulting in a modulated activity or function of the nucleobase or the nucleotide or nucleoside including the nucleobase. In embodiments, degradation of a nucleobase may be referred to as "nucleotide degradation". In embodiments degradation of a specific type of nucleobase or nucleotide may be referred to as degradation of the specific nucleobase type or nucleotide type, for example "dC degradation" refers to degradation of a deoxycytidine (e.g., degradation of a cytosine nucleobase in a deoxycytidine, degradation of a deoxycytidine in a deoxycytidine triphosphate, degradation of a cytosine nucleobase in an DNA nucleic acid). FIG. 3 depicts an example of a reaction resulting in a degraded dC.

The embodiments set forth below and recited in the claims can be understood in view of the above definitions.

Compositions and methods

The present disclosure provides compositions that comprise a solution containing a nucleotide having a protecting group such as a 3'-O-oxime moiety and a reagent having the structure R2 tethered to a reversible terminator such as R2-ONH$_2$, wherein R2 is —C(R6)(R7)(R8), —C(O)(R6), —P(O)(R6)(R7), —C(R6)(=C(R7)(R8)), —Si(R6)(R7)(R8), —SO$_2$(R6), substituted or unsubstituted cycloalkyl (e.g., $C_3$-$C_8$, $C_3$-$C_6$, or $C_5$-$C_6$), substituted or unsubstituted cycloalkenyl (e.g., $C_3$-$C_8$, $C_3$-$C_6$, or $C_5$-$C_6$), substituted or unsubstituted cycloalkynyl (e.g., $C_3$-$C_8$, $C_3$-$C_6$, or $C_5$-$C_6$), substituted or unsubstituted heteroalicyclyl (e.g., 3 to 8 membered, 3 to 6 membered, or 5 to 6 membered), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, R2 has a molecular weight greater than methyl. In embodiments, R2 has a molecular weight greater than ethyl. In embodiments, R2 has a molecular weight greater than 36 g/mol. In embodiments, R2 has a molecular weight greater than 57 g/mol. In embodiments, R2 has a molecular weight greater than 100 g/mol. In embodiments, R2 has a molecular weight greater than 200 g/mol. In embodiments, R2 has a molecular weight greater than 300 g/mol. In embodiments, R2 has a molecular weight greater than 400 g/mol. In embodiments, R2 has a molecular weight greater than 500 g/mol. In embodiments, R2 has a molecular weight greater than 600 g/mol. In embodiments, R2 has a molecular weight greater than 700 g/mol. In embodiments, R2 has a molecular weight greater than 800 g/mol. In embodiments, R2 has a molecular weight greater than 900 g/mol. In embodiments, R2 has a molecular weight less than or equal to 1000 g/mol. In embodiments, R2 has a molecular weight less than 1000 g/mol. Although not wishing to be limited by mechanism, it is believed that R2 moieties having more steric bulk than hydrogen and methyl yield improved synthetic results compared to smaller moieties, and produce fewer unwanted modifications to nucleic acids and nucleotides. See the results of Example 1A below. In embodiments, R2 is —C(R6)(R7)(R8) and R6, R7, and R8 are not all hydrogen. Similarly, in some cases R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. In particular configurations, the nucleotide has the structure:

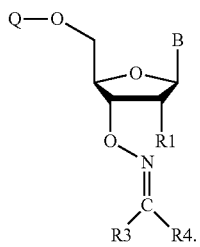

B can be a nucleobase. R1 can independently be a halogen, $OCH_3$, H or OH. Q can be independently monophosphate, diphosphate, triphosphate, hydrogen, or nucleic acid. R3 and R4 can be independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof, or an exogenous label moiety. In embodiments, R3 and R4 can be independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. By way of example, the moiety at the 3' position of the nucleotide can be an aldoxime (i.e. one of R3 or R4 is hydrogen) or a ketoxime (neither of R3 or R4 is hydrogen).

Substituted and unsubstituted B moieties are both consistent with the disclosure herein. In embodiments, B is substituted. In embodiments, B is unsubstituted. In embodiments, a substituted B (e.g., a substituted nucleobase) is substituted with at least one substituent group, size-limited substituent group, or lower substituent group; wherein if the substituted B is substituted with a plurality of groups selected from substituent groups, size-limited substituent groups, and lower substituent groups; each substituent group, size-limited substituent group, and/or lower substituent group may optionally be different. In embodiments, when B is substituted, it is substituted with at least one substituent group. In embodiments, when B is substituted, it is substituted with at least one size-limited substituent group. In embodiments, when B is substituted, it is substituted with at least one lower substituent group. In embodiments, B is a substituted adenine moiety. In embodiments, B is a substituted cytosine moiety. In embodiments, B is a substituted guanine moiety. In embodiments, B is a substituted thymine moiety. In embodiments, B is a substituted uracil moiety. In embodiments, B is an unsubstituted adenine moiety. In embodiments, B is an unsubstituted cytosine moiety. In embodiments, B is an unsubstituted guanine moiety. In embodiments, B is an unsubstituted thymine moiety. In embodiments, B is an unsubstituted uracil moiety.

Similarly, substituted and unsubstituted Q moieties are consistent with the disclosure herein. In embodiments, Q is substituted. In embodiments, Q is unsubstituted. In embodiments, a substituted Q (e.g., a substituted monophosphate, substituted diphosphate, substituted triphosphate, hydrogen atom, and/or substituted nucleic acid) is substituted with at least one substituent group, size-limited substituent group, or lower substituent group; wherein if the substituted Q is substituted with a plurality of groups selected from substituent groups, size-limited substituent groups, and lower substituent groups; each substituent group, size-limited substituent group, and/or lower substituent group may optionally be different. In embodiments, when Q is substituted, it is substituted with at least one substituent group. In embodiments, when Q is substituted, it is substituted with at least one size-limited substituent group. In embodiments, when Q is substituted, it is substituted with at least one lower substituent group.

In embodiments, Q is deoxyribonucleic acid. In embodiments, Q is ribonucleic acid. In embodiments, Q is independently monophosphate, diphosphate, triphosphate, or nucleic acid.

In embodiments, R1 is H. In embodiments, R1 is OH.

In embodiments, a substituted R3 (e.g., substituted alkyl, substituted alkenyl, substituted alkynyl, substituted cycloalkyl, substituted cycloalkenyl, substituted cycloalkynyl, substituted aryl, substituted heteroaryl, substituted heteroalicyclyl, substituted aralkyl, substituted heteroaralkyl, and/or substituted (heteroalicyclyl)alkyl) is substituted with at least one substituent group, size-limited substituent group, or lower substituent group; wherein if the substituted R3 is substituted with a plurality of groups selected from substituent groups, size-limited substituent groups, and lower substituent groups; each substituent group, size-limited substituent group, and/or lower substituent group may optionally be different. In embodiments, when R3 is substituted, it is substituted with at least one substituent group. In embodiments, when R3 is substituted, it is substituted with at least one size-limited substituent group. In embodiments, when R3 is substituted, it is substituted with at least one lower substituent group.

In embodiments, R3 is independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof, or an exogenous label moiety. In embodiments, R3 is independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. In embodiments, R3 is independently an exogenous label moiety.

In embodiments, a substituted R4 (e.g., substituted alkyl, substituted alkenyl, substituted alkynyl, substituted cycloalkyl, substituted cycloalkenyl, substituted cycloalkynyl, substituted aryl, substituted heteroaryl, substituted heteroalicyclyl, substituted aralkyl, substituted heteroaralkyl, and/or substituted (heteroalicyclyl)alkyl) is substituted with at least one substituent group, size-limited substituent group, or lower substituent group; wherein if the substituted R4 is substituted with a plurality of groups selected from substituent groups, size-limited substituent groups, and lower substituent groups; each substituent group, size-limited substituent group, and/or lower substituent group may optionally be different. In embodiments, when R4 is substituted, it is substituted with at least one substituent group. In embodiments, when R4 is substituted, it is substituted with at least one size-limited substituent group. In embodiments, when R4 is substituted, it is substituted with at least one lower substituent group.

In embodiments, R4 is independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof, or an exogenous label moiety. In embodiments, R4 is independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. In embodiments, R4 is independently an exogenous label moiety.

In embodiments, the solution is an aqueous solution. In embodiments, the nucleotide is attached to a solid support and wherein the solid support is in contact with the solution. In embodiments, the reagent that comprises the structure R2-$ONH_2$ is attached to a solid support in contact with the aqueous solution. In embodiments, the nucleobase comprises an exogenous label moiety.

The present disclosure also provides methods for modifying a nucleotide. The methods can be carried out by reacting a nucleotide having a protecting moiety such as a 3'-O-oxime moiety to a reagent having the structure R2-block, wherein block is a blocking moiety such as the reversible terminator moiety —$ONH_2$, to produce a nucleotide having a 3'-O—$NH_2$ moiety or other moiety as a blocking moiety or a reversible terminator. In some cases R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. R2 can be an alkyl other than methyl. In embodiments, R2 is not —$CH_3$. In embodiments, R2 is not hydrogen. In embodiments, R2 is not hydrogen, or —$CH_3$. The present disclosure also provides a method for modifying a nucleotide. The method can be carried out by reacting a nucleotide having a 3'-O-oxime moiety with a reagent having the structure R2-$ONH_2$ to produce a nucleotide having a 3'-O—$NH_2$ moiety, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, a substituted R2 (e.g., substituted alkyl, substituted alkenyl, substituted alkynyl, substituted cycloalkyl, substituted cycloalkenyl, substituted cycloalkynyl, substituted aryl, substituted heteroaryl, substituted heteroalicyclyl, substituted aralkyl, substituted heteroaralkyl, and/or substituted (heteroalicyclyl)alkyl) is substituted with at least one substituent group, size-limited substituent group, or lower substituent group; wherein if the substituted R2 is substituted with a plurality of groups selected from substituent groups, size-limited substituent groups, and lower substituent groups; each substituent group, size-limited substituent group, and/or lower substituent group may optionally be different. In embodiments, when R2 is substituted, it is substituted with at least one substituent group. In embodiments, when R2 is substituted, it is substituted with at least one size-limited substituent group. In embodiments, when R2 is substituted, it is substituted with at least one lower substituent group.

In embodiments, R2 is —C(R6)(R7)(R8), —C(O)(R6), —P(O)(R6)(R7), —C(R6)(=C(R7)(R8)), —Si(R6)(R7)(R8), —$SO_2$(R6), substituted or unsubstituted cycloalkyl (e.g., $C_3$-$C_8$, $C_3$-$C_6$, or $C_5$-$C_6$), substituted or unsubstituted cycloalkenyl (e.g., $C_3$-$C_8$, $C_3$-$C_6$, or $C_5$-$C_6$), substituted or unsubstituted cycloalkynyl (e.g., $C_3$-$C_8$, $C_3$-$C_6$, or $C_5$-$C_6$), substituted or unsubstituted heteroalicyclyl (e.g., 3 to 8 membered, 3 to 6 membered, or 5 to 6 membered), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R2 is —C(R6)(R7)(R8). In embodiments, R2 is —C(O)(R6). In embodiments, R2 is —P(O)(R6)(R7). In embodiments, R2 is —C(R6)(=C(R7)(R8)). In embodiments, R2 is —Si(R6)(R7)(R8). In embodiments, R2 is —$SO_2$(R6). In embodiments, R2 is substituted or unsubstituted cycloalkyl (e.g., $C_3$-$C_8$, $C_3$-$C_6$, or $C_5$-$C_6$). In embodiments, R2 is substituted or unsubstituted cycloalkenyl (e.g., $C_3$-$C_8$, $C_3$-$C_6$, or $C_5$-$C_6$). In embodiments, R2 is substituted or unsubstituted cycloalkynyl (e.g., $C_3$-$C_8$, $C_3$-$C_6$, or $C_5$-$C_6$). In embodiments, R2 is substituted or unsubstituted heteroalicyclyl (e.g., 3 to 8 membered, 3 to 6 membered, or 5 to 6 membered). In embodiments, R2 is substituted or unsubstituted aryl (e.g., $C_6$-$C_{10}$ aryl, $C_{10}$ aryl, or phenyl). In embodiments, R2 is substituted or unsubstituted heteroaryl (e.g., 5 to 10 membered heteroaryl, 5 to 9 membered heteroaryl, or 5 to 6 membered heteroaryl). In embodiments, R2 is unsubstituted cycloalkyl (e.g., $C_3$-$C_8$, $C_3$-$C_6$, or $C_5$-$C_6$). In embodiments, R2 is unsubstituted cycloalkenyl (e.g., $C_3$-$C_8$, $C_3$-$C_6$, or $C_5$-$C_6$). In embodiments, R2 is unsubstituted cycloalkynyl (e.g., $C_3$-$C_8$, $C_3$-$C_6$, or $C_5$-$C_6$). In embodiments, R2 is unsubstituted heteroalicyclyl (e.g., 3 to 8 membered, 3 to 6 membered, or 5 to 6 membered). In embodiments, R2 is unsubstituted aryl (e.g., $C_6$-$C_{10}$ aryl, $C_{10}$ aryl, or phenyl). In embodiments, R2 is unsubstituted heteroaryl (e.g., 5 to 10 membered heteroaryl, 5 to 9 membered heteroaryl, or 5 to 6 membered heteroaryl). In embodiments, R2 is not unsubstituted methyl. In embodiments, R2 is not unsubstituted ethyl. In embodiments, R2 is not unsubstituted propyl.

R6, R7, and R8 are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted alkyl (e.g., $C_1$-$C_8$ alkyl, $C_1$-$C_6$ alkyl, or $C_1$-$C_4$ alkyl), substituted or unsubstituted alkenyl (e.g., $C_2$-$C_8$ alkenyl, $C_2$-$C_6$ alkenyl, or $C_2$-$C_4$ alkenyl), substituted or unsubstituted alkynyl (e.g., $C_2$-$C_8$ alkynyl, $C_2$-$C_6$ alkynyl, or $C_2$-$C_4$ alkynyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$, $C_3$-$C_6$, or $C_5$-$C_6$), substituted or unsubstituted cycloalkenyl (e.g., $C_3$-$C_8$, $C_3$-$C_6$, or $C_5$-$C_6$), substituted or unsubstituted cycloalkynyl (e.g., $C_3$-$C_8$, $C_3$-$C_6$, or $C_5$-$C_6$), substituted or unsubstituted aryl (e.g., $C_6$-$C_{10}$ aryl, $C_{10}$ aryl, or phenyl), substituted or unsubstituted heteroaryl (e.g., 5 to 10 membered heteroaryl, 5 to 9 membered heteroaryl, or 5 to 6 membered heteroaryl), substituted or unsubstituted heteroalicyclyl (e.g., 3 to 8 membered, 3 to 6 membered, or 5 to 6 membered), substituted or unsubstituted aralkyl, substituted or unsubstituted heteroaralkyl, substituted or unsubstituted (heteroalicyclyl)alkyl, or an exogenous label moiety. In embodiments, R6, R7, and R8 are not all hydrogen. In embodiments, R6 is not hydrogen. In embodiments, R7 is not hydrogen. In embodiments, R8 is not hydrogen. In embodiments, R2 is —C(R6)(R7)(R8) and R6, R7, and R8 are not all hydrogen.

In embodiments, R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl (e.g., $C_1$-$C_8$ alkyl, $C_1$-$C_6$ alkyl, or $C_1$-$C_4$ alkyl), substituted or unsubstituted alkenyl (e.g., $C_2$-$C_8$ alkenyl, $C_2$-$C_6$ alkenyl, or $C_2$-$C_4$ alkenyl), substituted or unsubstituted alkynyl (e.g., $C_2$-$C_8$ alkynyl, $C_2$-$C_6$ alkynyl, or $C_2$-$C_4$ alkynyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$, $C_3$-$C_6$, or $C_5$-$C_6$), substituted or unsubstituted cycloalkenyl (e.g., $C_3$-$C_8$, $C_3$-$C_6$, or $C_5$-$C_6$), substituted or unsubstituted cycloalkynyl (e.g., $C_3$-$C_8$, $C_3$-$C_6$, or $C_5$-$C_6$), substituted or unsubstituted aryl (e.g., $C_6$-$C_{10}$ aryl, $C_{10}$ aryl, or phenyl), substituted or unsubstituted heteroaryl (e.g., 5 to 10 membered heteroaryl, 5 to 9 membered heteroaryl, or 5 to 6 membered heteroaryl), substituted or unsubstituted heteroalicyclyl (e.g., 3 to 8 membered, 3 to 6 membered, or 5 to 6 membered), substituted or unsubstituted aralkyl, substituted or unsubstituted heteroaralkyl, or substituted or unsubstituted (heteroalicyclyl)alkyl. In embodiments, R6, R7, and R8 are not all hydrogen. In embodiments, R6 is not hydrogen. In embodiments, R7 is not hydrogen. In embodiments, R8 is not hydrogen. In embodiments, R2 is —C(R6)(R7)(R8) and R6, R7, and R8 are not all hydrogen.

In embodiments, a substituted R6 (e.g., substituted alkyl, substituted alkenyl, substituted alkynyl, substituted heteroalkyl, substituted cycloalkyl, substituted cycloalkenyl, substituted cycloalkynyl, substituted aryl, substituted heteroaryl, substituted heteroalicyclyl, substituted aralkyl, substituted heteroaralkyl, and/or substituted (heteroalicyclyl)alkyl) is substituted with at least one substituent group, size-limited substituent group, or lower substituent group; wherein if the substituted R6 is substituted with a plurality of groups selected from substituent groups, size-limited substituent groups, and lower substituent groups; each substituent group, size-limited substituent group, and/or lower substituent group may optionally be different. In embodiments, when R6 is substituted, it is substituted with at least one substituent group. In embodiments, when R6 is substituted, it is substituted with at least one size-limited substituent group. In embodiments, when R6 is substituted, it is substituted with at least one lower substituent group.

In embodiments, R6 is independently hydrogen. In embodiments, R6 is independently halogen. In embodiments, R6 is independently —CCl$_3$. In embodiments, R6 is independently —CBr$_3$. In embodiments, R6 is independently —CF$_3$. In embodiments, R6 is independently —CI$_3$. In embodiments, R6 is independently —CHCl$_2$. In embodiments, R6 is independently —CHBr$_2$. In embodiments, R6 is independently —CHF$_2$. In embodiments, R6 is independently —CHI$_2$. In embodiments, R6 is independently —CH$_2$Cl. In embodiments, R6 is independently —CH$_2$Br. In embodiments, R6 is independently —CH$_2$F. In embodiments, R6 is independently —CH$_2$I. In embodiments, R6 is independently —CN. In embodiments, R6 is independently —OH. In embodiments, R6 is independently —NH$_2$. In embodiments, R6 is independently —COOH. In embodiments, R6 is independently —CONH$_2$. In embodiments, R6 is independently —NO$_2$. In embodiments, R6 is independently —SH. In embodiments, R6 is independently —SO$_3$H. In embodiments, R6 is independently —SO$_4$H. In embodiments, R6 is independently —SO$_2$NH$_2$. In embodiments, R6 is independently —NHNH$_2$. In embodiments, R6 is independently —ONH$_2$. In embodiments, R6 is independently —NHC(O)NHNH$_2$. In embodiments, R6 is independently —NHC(O)NH$_2$. In embodiments, R6 is independently —NHSO$_2$H. In embodiments, R6 is independently —NHC(O)H. In embodiments, R6 is independently —NHC(O)OH. In embodiments, R6 is independently —NHOH. In embodiments, R6 is independently —OCCl$_3$. In embodiments, R6 is independently —OCF$_3$. In embodiments, R6 is independently —OCBr$_3$. In embodiments, R6 is independently —OC$_3$. In embodiments, R6 is independently —OCHCl$_2$. In embodiments, R6 is independently —OCHBr$_2$. In embodiments, R6 is independently —OCHI$_2$. In embodiments, R6 is independently —OCHF$_2$. In embodiments, R6 is independently —OCH$_2$Cl. In embodiments, R6 is independently —OCH$_2$Br. In embodiments, R6 is independently —OCH$_2$I. In embodiments, R6 is independently —OCH$_2$F. In embodiments, R6 is independently —SF$_5$. In embodiments, R6 is independently —N$_3$. In embodiments, R6 is independently substituted or unsubstituted alkyl (e.g., $C_1$-$C_8$ alkyl, $C_1$-$C_6$ alkyl, or $C_1$-$C_4$ alkyl). In embodiments, R6 is independently substituted or unsubstituted alkenyl (e.g., $C_2$-$C_8$ alkenyl, $C_2$-$C_6$ alkenyl, or $C_2$-$C_4$ alkenyl). In embodiments, R6 is independently substituted or unsubstituted alkynyl (e.g., $C_2$-$C_8$ alkynyl, $C_2$-$C_6$ alkynyl, or $C_2$-$C_4$ alkynyl). In embodiments, R6 is independently substituted or unsubstituted heteroalkyl (e.g., 2 to 8 membered heteroalkyl, 2 to 6 membered heteroalkyl, or 2 to 4 membered heteroalkyl). In embodiments, R6 is independently substituted or unsubstituted cycloalkyl (e.g., $C_3$-$C_8$, $C_3$-$C_6$, or $C_5$-$C_6$). In embodiments, R6 is independently substituted or unsubstituted cycloalkenyl (e.g., $C_3$-$C_8$, $C_3$-$C_6$, or $C_5$-$C_6$). In embodiments, R6 is independently substituted or unsubstituted cycloalkynyl (e.g., $C_3$-$C_8$, $C_3$-$C_6$, or $C_5$-$C_6$). In embodiments, R6 is independently substituted or unsubstituted aryl (e.g., $C_6$-$C_{10}$ aryl, $C_{10}$ aryl, or phenyl). In embodiments, R6 is independently substituted or unsubstituted heteroaryl (e.g., 5 to 10 membered heteroaryl, 5 to 9 membered heteroaryl, or 5 to 6 membered heteroaryl). In embodiments, R6 is independently substituted or unsubstituted heteroalicyclyl (e.g., 3 to 8 membered, 3 to 6 membered, or 5 to 6 membered). In embodiments, R6 is independently substituted or unsubstituted aralkyl. In embodiments, R6 is independently substituted or unsubstituted heteroaralkyl. In embodiments, R6 is independently substituted or unsubstituted (heteroalicyclyl)alkyl. In embodiments, R6 is independently an exogenous label moiety.

In embodiments, R6 is independently unsubstituted alkyl (e.g., $C_1$-$C_8$ alkyl, $C_1$-$C_6$ alkyl, or $C_1$-$C_4$ alkyl). In embodiments, R6 is independently unsubstituted alkenyl (e.g., $C_2$-$C_8$ alkenyl, $C_2$-$C_6$ alkenyl, or $C_2$-$C_4$ alkenyl). In embodiments, R6 is independently unsubstituted alkynyl (e.g., $C_2$-$C_8$ alkynyl, $C_2$-$C_6$ alkynyl, or $C_2$-$C_4$ alkynyl). In embodiments, R6 is independently unsubstituted heteroalkyl (e.g., 2 to 8 membered heteroalkyl, 2 to 6 membered heteroalkyl, or 2 to 4 membered heteroalkyl). In embodiments, R6 is independently unsubstituted cycloalkyl (e.g., $C_3$-$C_8$, $C_3$-$C_6$, or $C_5$-$C_6$). In embodiments, R6 is independently unsubstituted cycloalkenyl (e.g., $C_3$-$C_8$, $C_3$-$C_6$, or $C_5$-$C_6$). In embodiments, R6 is independently unsubstituted cycloalkynyl (e.g., $C_3$-$C_8$, $C_3$-$C_6$, or $C_5$-$C_6$). In embodiments, R6 is independently unsubstituted aryl (e.g., $C_6$-$C_{10}$ aryl, $C_{10}$ aryl, or phenyl). In embodiments, R6 is independently unsubstituted heteroaryl (e.g., 5 to 10 membered heteroaryl, 5 to 9 membered heteroaryl, or 5 to 6 membered heteroaryl). In embodiments, R6 is independently unsubstituted heteroalicyclyl (e.g., 3 to 8 membered, 3 to 6 membered, or 5 to 6 membered). In embodiments, R6 is independently unsubstituted aralkyl. In embodiments, R6 is independently unsubstituted heteroaralkyl. In embodiments, R6 is independently unsubstituted (heteroalicyclyl)alkyl.

In embodiments, a substituted R7 (e.g., substituted alkyl, substituted alkenyl, substituted alkynyl, substituted heteroalkyl, substituted cycloalkyl, substituted cycloalkenyl, substituted cycloalkynyl, substituted aryl, substituted heteroaryl, substituted heteroalicyclyl, substituted aralkyl, substituted heteroaralkyl, and/or substituted (heteroalicyclyl)alkyl) is substituted with at least one substituent group, size-limited substituent group, or lower substituent group; wherein if the substituted R7 is substituted with a plurality of groups selected from substituent groups, size-limited substituent groups, and lower substituent groups; each substituent group, size-limited substituent group, and/or lower substituent group may optionally be different. In embodiments, when R7 is substituted, it is substituted with at least one substituent group. In embodiments, when R7 is substituted, it is substituted with at least one size-limited substituent group. In embodiments, when R7 is substituted, it is substituted with at least one lower substituent group.

In embodiments, R7 is independently hydrogen. In embodiments, R7 is independently halogen. In embodiments, R7 is independently —$CCl_3$. In embodiments, R7 is independently —$CBr_3$. In embodiments, R7 is independently —$CF_3$. In embodiments, R7 is independently —$CI_3$. In embodiments, R7 is independently —$CHCl_2$. In embodiments, R7 is independently —$CHBr_2$. In embodiments, R7 is independently —$CHF_2$. In embodiments, R7 is independently —$CHI_2$. In embodiments, R7 is independently —$CH_2Cl$. In embodiments, R7 is independently —$CH_2Br$. In embodiments, R7 is independently —$CH_2F$. In embodiments, R7 is independently —$CH_2I$. In embodiments, R7 is independently —CN. In embodiments, R7 is independently —OH. In embodiments, R7 is independently —$NH_2$. In embodiments, R7 is independently —COOH. In embodiments, R7 is independently —$CONH_2$. In embodiments, R7 is independently —$NO_2$. In embodiments, R7 is independently —SH. In embodiments, R7 is independently —$SO_3H$. In embodiments, R7 is independently —$SO_4H$. In embodiments, R7 is independently —$SO_2NH_2$. In embodiments, R7 is independently —$NHNH_2$. In embodiments, R7 is independently —$ONH_2$. In embodiments, R7 is independently —$NHC(O)NHNH_2$. In embodiments, R7 is independently —$NHC(O)NH_2$. In embodiments, R7 is independently —$NHSO_2H$. In embodiments, R7 is independently —NHC(O)H. In embodiments, R7 is independently —NHC(O)OH. In embodiments, R7 is independently —NHOH. In embodiments, R7 is independently —$OCCl_3$. In embodiments, R7 is independently —$OCF_3$. In embodiments, R7 is independently —$OCBr_3$. In embodiments, R7 is independently —$OCI_3$. In embodiments, R7 is independently —$OCHCl_2$. In embodiments, R7 is independently —$OCHBr_2$. In embodiments, R7 is independently —$OCHI_2$. In embodiments, R7 is independently —$OCHF_2$. In embodiments, R7 is independently —$OCH_2Cl$. In embodiments, R7 is independently —$OCH_2Br$. In embodiments, R7 is independently —$OCH_2I$. In embodiments, R7 is independently —$OCH_2F$. In embodiments, R7 is independently —$SF_5$. In embodiments, R7 is independently —$N_3$. In embodiments, R7 is independently substituted or unsubstituted alkyl (e.g., $C_1$-$C_8$ alkyl, $C_1$-$C_6$ alkyl, or $C_1$-$C_4$ alkyl). In embodiments, R7 is independently substituted or unsubstituted alkenyl (e.g., $C_2$-$C_8$ alkenyl, $C_2$-$C_6$ alkenyl, or $C_2$-$C_4$ alkenyl). In embodiments, R7 is independently substituted or unsubstituted alkynyl (e.g., $C_2$-$C_8$ alkynyl, $C_2$-$C_6$ alkynyl, or $C_2$-$C_4$ alkynyl). In embodiments, R7 is independently substituted or unsubstituted heteroalkyl (e.g., 2 to 8 membered heteroalkyl, 2 to 6 membered heteroalkyl, or 2 to 4 membered heteroalkyl). In embodiments, R7 is independently substituted or unsubstituted cycloalkyl (e.g., $C_3$-$C_8$, $C_3$-$C_6$, or $C_5$-$C_6$). In embodiments, R7 is independently substituted or unsubstituted cycloalkenyl (e.g., $C_3$-$C_8$, $C_3$-$C_6$, or $C_5$-$C_6$). In embodiments, R7 is independently substituted or unsubstituted cycloalkynyl (e.g., $C_3$-$C_8$, $C_3$-$C_6$, or $C_5$-$C_6$). In embodiments, R7 is independently substituted or unsubstituted aryl (e.g., $C_6$-$C_{10}$ aryl, $C_{10}$ aryl, or phenyl). In embodiments, R7 is independently substituted or unsubstituted heteroaryl (e.g., 5 to 10 membered heteroaryl, 5 to 9 membered heteroaryl, or 5 to 6 membered heteroaryl). In embodiments, R7 is independently substituted or unsubstituted heteroalicyclyl (e.g., 3 to 8 membered, 3 to 6 membered, or 5 to 6 membered). In embodiments, R7 is independently substituted or unsubstituted aralkyl. In embodiments, R7 is independently substituted or unsubstituted heteroaralkyl. In embodiments, R7 is independently substituted or unsubstituted (heteroalicyclyl)alkyl. In embodiments, R7 is independently an exogenous label moiety.

In embodiments, R7 is independently unsubstituted alkyl (e.g., $C_1$-$C_8$ alkyl, $C_1$-$C_6$ alkyl, or $C_1$-$C_4$ alkyl). In embodiments, R7 is independently unsubstituted alkenyl (e.g., $C_2$-$C_8$ alkenyl, $C_2$-$C_6$ alkenyl, or $C_2$-$C_4$ alkenyl). In embodiments, R7 is independently unsubstituted alkynyl (e.g., $C_2$-$C_8$ alkynyl, $C_2$-$C_6$ alkynyl, or $C_2$-$C_4$ alkynyl). In embodiments, R7 is independently unsubstituted heteroalkyl (e.g., 2 to 8 membered heteroalkyl, 2 to 6 membered heteroalkyl, or 2 to 4 membered heteroalkyl). In embodiments, R7 is independently unsubstituted cycloalkyl (e.g., $C_3$-$C_8$, $C_3$-$C_6$, or $C_5$-$C_6$). In embodiments, R7 is independently unsubstituted cycloalkenyl (e.g., $C_3$-$C_8$, $C_3$-$C_6$, or $C_5$-$C_6$). In embodiments, R7 is independently unsubstituted cycloalkynyl (e.g., $C_3$-$C_8$, $C_3$-$C_6$, or $C_5$-$C_6$). In embodiments, R7 is independently unsubstituted aryl (e.g., $C_6$-$C_{10}$ aryl, $C_{10}$ aryl, or phenyl). In embodiments, R7 is independently unsubstituted heteroaryl (e.g., 5 to 10 membered heteroaryl, 5 to 9 membered heteroaryl, or 5 to 6 membered heteroaryl). In embodiments, R7 is independently unsubstituted heteroalicyclyl (e.g., 3 to 8 membered, 3 to 6 membered, or 5 to 6 membered). In embodiments, R7 is independently unsubstituted aralkyl. In embodiments, R7 is independently unsubstituted heteroaralkyl. In embodiments, R7 is independently unsubstituted (heteroalicyclyl)alkyl.

In embodiments, a substituted R8 (e.g., substituted alkyl, substituted alkenyl, substituted alkynyl, substituted heteroalkyl, substituted cycloalkyl, substituted cycloalkenyl, substituted cycloalkynyl, substituted aryl, substituted heteroaryl, substituted heteroalicyclyl, substituted aralkyl, substituted heteroaralkyl, and/or substituted (heteroalicyclyl)alkyl) is substituted with at least one substituent group, size-limited substituent group, or lower substituent group; wherein if the substituted R8 is substituted with a plurality of groups selected from substituent groups, size-limited substituent groups, and lower substituent groups; each substituent group, size-limited substituent group, and/or lower substituent group may optionally be different. In embodiments, when R8 is substituted, it is substituted with at least one substituent group. In embodiments, when R8 is substituted, it is substituted with at least one size-limited substituent group. In embodiments, when R8 is substituted, it is substituted with at least one lower substituent group.

In embodiments, R8 is independently hydrogen. In embodiments, R8 is independently halogen. In embodiments, R8 is independently —CCl$_3$. In embodiments, R8 is independently —CBr$_3$. In embodiments, R8 is independently —CF$_3$. In embodiments, R8 is independently —CI$_3$. In embodiments, R8 is independently —CHCl$_2$. In embodiments, R8 is independently —CHBr$_2$. In embodiments, R8 is independently —CHF$_2$. In embodiments, R8 is independently —CHI$_2$. In embodiments, R8 is independently —CH$_2$Cl. In embodiments, R8 is independently —CH$_2$Br. In embodiments, R8 is independently —CH$_2$F. In embodiments, R8 is independently —CH$_2$I. In embodiments, R8 is independently —CN. In embodiments, R8 is independently —OH. In embodiments, R8 is independently —NH$_2$. In embodiments, R8 is independently —COOH. In embodiments, R8 is independently —CONH$_2$. In embodiments, R8 is independently —NO$_2$. In embodiments, R8 is independently —SH. In embodiments, R8 is independently —SO$_3$H. In embodiments, R8 is independently —SO$_4$H. In embodiments, R8 is independently —SO$_2$NH$_2$. In embodiments, R8 is independently —NHNH$_2$. In embodiments, R8 is independently —ONH$_2$. In embodiments, R8 is independently —NHC(O)NHNH$_2$. In embodiments, R8 is independently —NHC(O)NH$_2$. In embodiments, R8 is independently —NHSO$_2$H. In embodiments, R8 is independently —NHC(O)H. In embodiments, R8 is independently —NHC(O)OH. In embodiments, R8 is independently —NHOH. In embodiments, R8 is independently —OCCl$_3$. In embodiments, R8 is independently —OCF$_3$. In embodiments, R8 is independently —OCBr$_3$. In embodiments, R8 is independently —OCI$_3$. In embodiments, R8 is independently —OCHCl$_2$. In embodiments, R8 is independently —OCHBr$_2$. In embodiments, R8 is independently —OCHI$_2$. In embodiments, R8 is independently —OCHF$_2$. In embodiments, R8 is independently —OCH$_2$Cl. In embodiments, R8 is independently —OCH$_2$Br. In embodiments, R8 is independently —OCH$_2$I. In embodiments, R8 is independently —OCH$_2$F. In embodiments, R8 is independently —SF$_5$. In embodiments, R8 is independently —N$_3$. In embodiments, R8 is independently substituted or unsubstituted alkyl (e.g., $C_1$-$C_8$ alkyl, $C_1$-$C_6$ alkyl, or $C_1$-$C_4$ alkyl). In embodiments, R8 is independently substituted or unsubstituted alkenyl (e.g., $C_2$-$C_8$ alkenyl, $C_2$-$C_6$ alkenyl, or $C_2$-$C_4$ alkenyl). In embodiments, R8 is independently substituted or unsubstituted alkynyl (e.g., $C_2$-$C_8$ alkynyl, $C_2$-$C_6$ alkynyl, or $C_2$-$C_4$ alkynyl). In embodiments, R8 is independently substituted or unsubstituted heteroalkyl (e.g., 2 to 8 membered heteroalkyl, 2 to 6 membered heteroalkyl, or 2 to 4 membered heteroalkyl). In embodiments, R8 is independently substituted or unsubstituted cycloalkyl (e.g., $C_3$-$C_8$, $C_3$-$C_6$, or $C_5$-$C_6$). In embodiments, R8 is independently substituted or unsubstituted cycloalkenyl (e.g., $C_3$-$C_8$, $C_3$-$C_6$, or $C_5$-$C_6$). In embodiments, R8 is independently substituted or unsubstituted cycloalkynyl (e.g., $C_3$-$C_8$, $C_3$-$C_6$, or $C_5$-$C_6$). In embodiments, R8 is independently substituted or unsubstituted aryl (e.g., $C_6$-$C_{10}$ aryl, $C_{10}$ aryl, or phenyl). In embodiments, R8 is independently substituted or unsubstituted heteroaryl (e.g., 5 to 10 membered heteroaryl, 5 to 9 membered heteroaryl, or 5 to 6 membered heteroaryl). In embodiments, R8 is independently substituted or unsubstituted heteroalicyclyl (e.g., 3 to 8 membered, 3 to 6 membered, or 5 to 6 membered). In embodiments, R8 is independently substituted or unsubstituted aralkyl. In embodiments, R8 is independently substituted or unsubstituted heteroaralkyl. In embodiments, R8 is independently substituted or unsubstituted (heteroalicyclyl)alkyl. In embodiments, R8 is independently an exogenous label moiety.

In embodiments, R8 is independently unsubstituted alkyl (e.g., $C_1$-$C_8$ alkyl, $C_1$-$C_6$ alkyl, or $C_1$-$C_4$ alkyl). In embodiments, R8 is independently unsubstituted alkenyl (e.g., $C_2$-$C_8$ alkenyl, $C_2$-$C_6$ alkenyl, or $C_2$-$C_4$ alkenyl). In embodiments, R8 is independently unsubstituted alkynyl (e.g., $C_2$-$C_8$ alkynyl, $C_2$-$C_6$ alkynyl, or $C_2$-$C_4$ alkynyl). In embodiments, R8 is independently unsubstituted heteroalkyl (e.g., 2 to 8 membered heteroalkyl, 2 to 6 membered heteroalkyl, or 2 to 4 membered heteroalkyl). In embodiments, R8 is independently unsubstituted cycloalkyl (e.g., $C_3$-$C_8$, $C_3$-$C_6$, or $C_5$-$C_6$). In embodiments, R8 is independently unsubstituted cycloalkenyl (e.g., $C_3$-$C_8$, $C_3$-$C_6$, or $C_5$-$C_6$). In embodiments, R8 is independently unsubstituted cycloalkynyl (e.g., $C_3$-$C_8$, $C_3$-$C_6$, or $C_5$-$C_6$). In embodiments, R8 is independently unsubstituted aryl (e.g., $C_6$-$C_{10}$ aryl, $C_{10}$ aryl, or phenyl). In embodiments, R8 is independently unsubstituted heteroaryl (e.g., 5 to 10 membered heteroaryl, 5 to 9 membered heteroaryl, or 5 to 6 membered heteroaryl). In embodiments, R8 is independently unsubstituted heteroalicyclyl (e.g., 3 to 8 membered, 3 to 6 membered, or 5 to 6 membered). In embodiments, R8 is independently unsubstituted aralkyl. In embodiments, R8 is independently unsubstituted heteroaralkyl. In embodiments, R8 is independently unsubstituted (heteroalicyclyl)alkyl.

Turning to FIG. 1A, one sees that with increasing R2 size, one observes a decreasing percentage of dC degradation in final reaction product as observed after 60 minutes of a 25 C reaction. One also observes that R2 moieties having at least two carbon atoms perform better in terms of starting material consumption than do smaller R2 moieties.

In some configurations, the nucleotide that has the 3'-O-oxime moiety can have the structure:

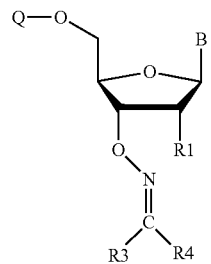

and the nucleotide that has the 3'-O—NH₂ moiety can have the structure:

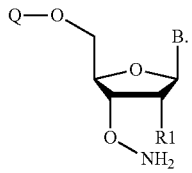

B can be a nucleobase. R1 can independently be a halogen, OCH₃, H or OH. Q can be independently monophosphate, diphosphate, triphosphate, or nucleic acid. R3 and R4 can be independently H, CH₃, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. By way of example, the moiety at the 3' position of the nucleotide can be an aldoxime (i.e. one of R3 or R4 is hydrogen) or a ketoxime (neither of R3 or R4 is hydrogen).

In embodiments, the reaction occurs in an aqueous solution. In embodiments, the nucleotide is attached to a solid support in contact with the aqueous solution.

In embodiments, the nucleotide that is produced comprises a deoxynucleotide. In embodiments, the nucleotide that is produced includes:

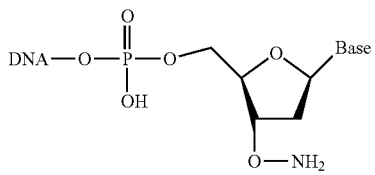

wherein Base is the nucleobase, and wherein DNA is independently a single stranded deoxyribonucleic acid or double stranded deoxyribonucleic acid. In embodiments, Base has a value of B.

In embodiments, the reagent is independently one of:

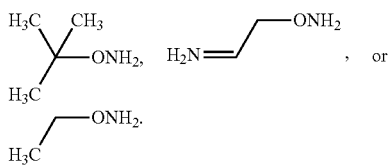

Figure 2:
FIG. 2 presents examples of deblocking reagents. All examples in this figure share a common —O—$NH_2$ reversible terminator moiety (at right in each molecule as presented) tethered to various R2 groups (at left in each molecule as presented) ranging in molecular weight and chemical structure. Similar deblocking reagents having R2 groups as disclosed herein tethered to alternate reversible terminator moieties, such as —O—$NHCH_3$, —O—$CH_2N_3$, or other moiety such as those consistent with reversible termination of nucleic acid extension, are also contemplated herein in combination with the R2 moieties presented here or otherwise disclosed herein.
Figure 2:
Figure 2:
Figure 2:
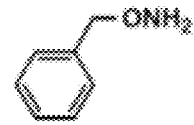
Figure 2:
Figure 2:
Figure 2:
Figure 2:
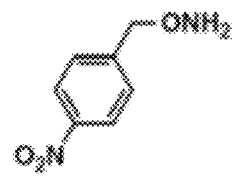
Figure 2:
Figure 2:
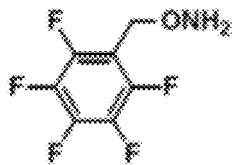
Figure 2:
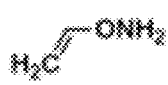
Figure 2:
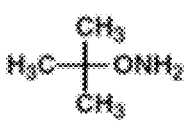
Figure 2:
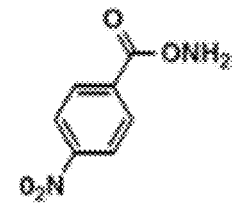
Figure 2:
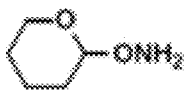
Figure 2:
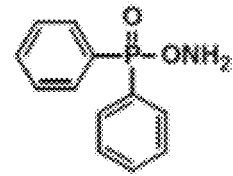
Figure 2:
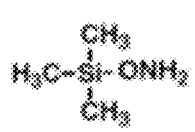
Figure 2:
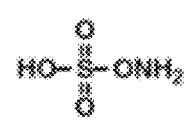
Figure 2:
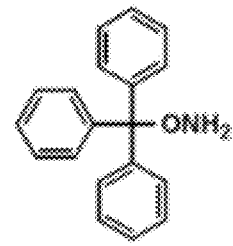

Additional individual examples of the reagent include the molecules listed in FIG. 1B and the molecules listed in FIG. 2. The present disclosure also provides a method for modifying a nucleotide. The method can be carried out by reacting a nucleotide having a 3'-O-oxime moiety with a reagent having the structure R2-ONH₂ to produce a nucleotide having a 3'-O—NH₂ moiety, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. In some configurations, the nucleotide that has the 3'-O-oxime moiety can have the structure:

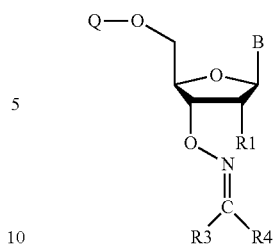

and the nucleotide that has the 3'-O—NH₂ moiety can have the structure:

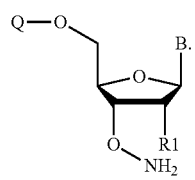

B can be a nucleobase. R1 can independently be a halogen, OCH₃, H or OH. Q can be independently monophosphate, diphosphate, triphosphate, or nucleic acid. R3 and R4 can be independently H, CH₃, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. By way of example, the moiety at the 3' position of the nucleotide can be an aldoxime (i.e. one of R3 or R4 is hydrogen) or a ketoxime (neither of R3 or R4 is hydrogen).

A method or composition of the present disclosure can include any of a variety of nucleotides. The nucleotide can be a native nucleotide, nucleotide analog or modified nucleotide as desired to suit a particular application or configuration set forth herein. Optionally, a nucleotide has a nitrogenous base, five-carbon sugar, and phosphate group, wherein any moiety of the nucleotide may be modified, removed and/or replaced as compared to a native nucleotide. For example, the 5' oxygen of a nucleotide need not have a phosphate moiety and can instead be protected with an exogenous moiety such as dimethoxytrityl (DMT) moiety. Reactive atoms in the base moiety of a nucleotide can be protected with exogenous moieties if desired. Often, methods and compositions disclosed herein comprise cytosine bases, and the cytosine bases are preserved in an undegraded or unmodified form at a higher rate than comparable methods or compositions in the prior art, as represented for example by the point DRT 1 in FIG. 1A.

Nucleotides that are used in a composition, method, apparatus or system herein can include terminators that reversibly prevent subsequent nucleotide incorporation at the 3'-end of the primer after the analog has been incorporated into the primer. For example, U.S. Pat. No. 7,544,794 (published Jun. 9, 2009), U.S. Pat. No. 8,034,923 (published Oct. 11, 2011) and U.S. Pat. No. 10,472,383 (published Nov. 12, 2019) (the disclosures of each of which being incorporated herein by reference in their respective entireties) describe reversible terminators in which the 3'—OH group is replaced by a 3'-ONH₂ moiety. These reversible terminators are resistant to modification by nucleic acid enzymes such as polymerases and ligases such that they prevent addition of a subsequent base at the 3' blocked position, thereby terminating extension of the nucleic acid strand when they are incorporated. The amino moiety can be removed from a nucleotide (for example, when the nucleotide is at the 3' end of a primer) by nitrous acid (HONO), thereby deblocking the nucleotide. The deblocked nucleotide will have a 3'OH that can be acted upon by a polymerase such that the 3' oxygen forms a covalent bond with the 5' phosphate of another nucleotide in a reaction known as an incorporation reaction or extension reaction. Removal of the amino moiety from a nucleotide via a deblocking step can similarly allow the nucleotide to be acted upon by a ligase such that the 3' oxygen forms a covalent bond with the 5' phosphate of an oligonucleotide in an incorporation or extension reaction.

A number of blocking moieties are consistent with the disclosure herein. Some blocking moieties share the characteristic that they do not prohibit the nucleotide to which they are bound from being incorporated at their 5' ends to an available 3' OH moiety by a nucleotide polymerizing enzyme, so as to incorporate the nucleotide that blocks further extension. Generally, larger moieties such as protecting moieties are often too large to be incorporated by nucleic acid polymerase enzyme. In embodiments, 3'-reversible terminators and 3' blocking moieties include —ONH$_2$, —ONHCH$_3$, —OCH$_2$N$_3$, and —ONHCOCH$_3$. In embodiments, a 3'-blocking moiety is —ONH$_2$. In embodiments, a 3'-blocking moiety is —ONHCH$_3$. In embodiments, a 3'-blocking moiety is —OCH$_2$N$_3$. In embodiments, a 3'-blocking moiety is and —ONHCOCH$_3$. In embodiments, a 3'-blocking moiety is a 3'-O-oxime moiety. In embodiments, a 3'-reversible terminator moiety is a 3'-O-oxime moiety.

The present disclosure provides new and useful reagents and methods for synthesizing reversibly terminated nucleotides, such as those that have a 3'-ONH$_2$ moiety. Such reversibly terminated nucleotides can be synthesized by reacting a precursor nucleotide, having a 3'-O-oxime moiety, with an alkoxyamine reagent having the structure R2-ONH$_2$. Particularly useful reagents include those in which R2 is a moiety other than hydrogen. For example, R2 can be alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. Particularly useful R2 moieties include, for example, —CH$_2$CH$_3$, —CH$_2$CHCH$_2$, and —C(CH$_3$)$_3$. In embodiments, R2 is as described herein, including in embodiments, claims, and figures. Thus, useful alkoxyamine reagents can include one or more of the following molecules:

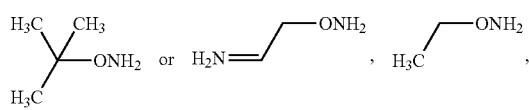

as well as any of the molecules listed in FIG. 1A or FIG. 2.

Any of a variety of substitutions can be made to the above R2 moieties. For example, one or more of the hydrogens in the —CH$_2$CH$_3$ or —CH$_2$CHCH$_2$ moieties can be substituted with a carbonyl (—CO$_2$), alcohol (—OH), amine (—NH$_2$) or halogen (e.g. Bromine, Fluorine, Chlorine, or Iodine). Similarly, one or more of the hydrogens in one or more of the methyls of the —C(CH$_3$)$_3$ moiety can be substituted in this way. In particular, applications the additional steric bulk provided by these types of substitutions can beneficially favor conversion of a 3'-O-oxime moiety of a nucleotide to a 3'-O—NH$_2$ moiety over unwanted side reactions that modify the nucleobase moiety of the nucleotide.

In embodiments, R2 is independently

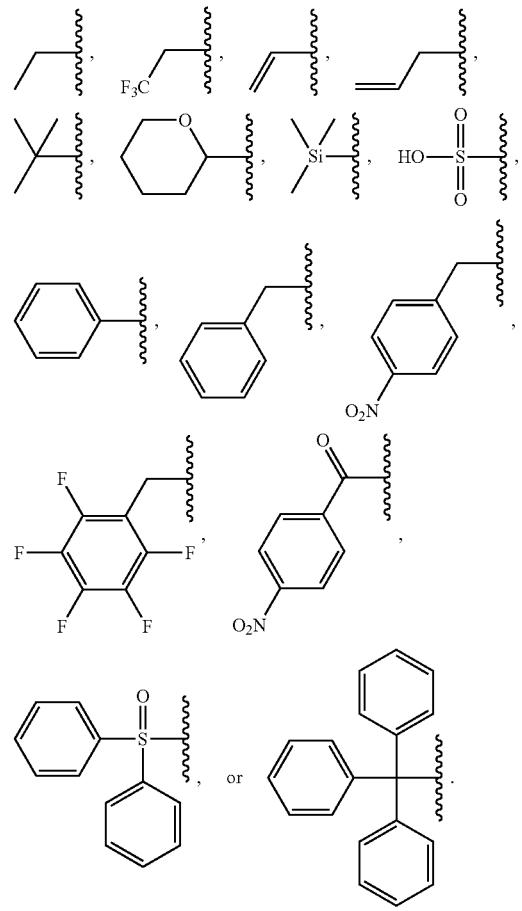

In embodiments, R2 is independently

In embodiments, R2 is independently

In embodiments, R2 is independently

In embodiments, R2 is independently

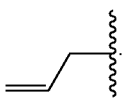

In embodiments, R2 is independently

In embodiments, R2 is independently

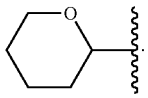

In embodiments, R2 is independently

In embodiments, R2 is independently

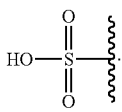

In embodiments, R2 is independently

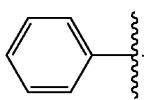

In embodiments, R2 is independently

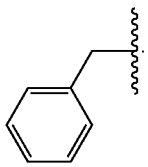

In embodiments, R2 is independently

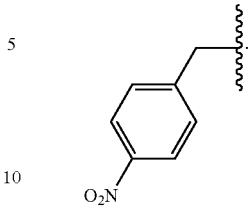

In embodiments, R2 is independently

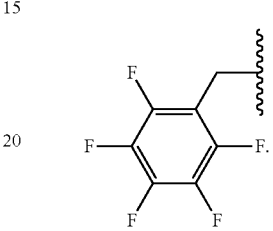

In embodiments, R2 is independently

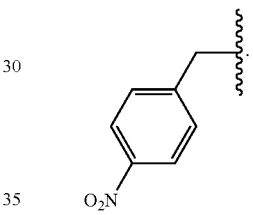

In embodiments, R2 is independently

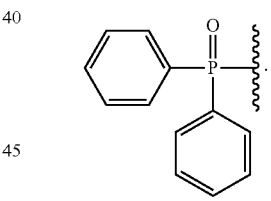

In embodiments, R2 is independently

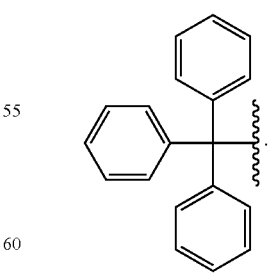

In some configurations of the methods and compositions set forth herein, R2 in the formula R2-ONH$_2$ can be CH$_3$. However, R2 need not be CH$_3$. Rather, R2 can be a higher order alkyl than a methyl (i.e. R2 can have more than one carbon). Accordingly, R2 can be an alkyl other than methyl.

In embodiments, R2 is not —CH₃. In embodiments, R2 is not hydrogen. In embodiments, R2 is not hydrogen, or —CH₃. In embodiments, R2 is —C(R6)(R7)(R8), —C(O)(R6), —P(O)(R6)(R7), —C(R6)(=C(R7)(R8)), —Si(R6)(R7)(R8), —SO₂(R6), substituted or unsubstituted cycloalkyl (e.g., C₃-C₈, C₃-C₆, or C₅-C₆), substituted or unsubstituted cycloalkenyl (e.g., C₃-C₈, C₃-C₆, or C₅-C₆), substituted or unsubstituted cycloalkynyl (e.g., C₃-C₈, C₃-C₆, or C₅-C₆), substituted or unsubstituted heteroalicyclyl (e.g., 3 to 8 membered, 3 to 6 membered, or 5 to 6 membered), substituted or unsubstituted aryl (e.g., C₆-C₁₀ aryl, C₁₀ aryl, or phenyl), or substituted or unsubstituted heteroaryl (e.g., 5 to 10 membered heteroaryl, 5 to 9 membered heteroaryl, or 5 to 6 membered heteroaryl). In embodiments, R2 has a molecular weight greater than methyl. In embodiments, R2 has a molecular weight greater than ethyl. In embodiments, R2 has a molecular weight greater than 36 g/mol. In embodiments, R2 has a molecular weight greater than 57 g/mol. In embodiments, R2 has a molecular weight greater than 100 g/mol. In embodiments, R2 has a molecular weight greater than 200 g/mol. In embodiments, R2 has a molecular weight greater than 300 g/mol. In embodiments, R2 has a molecular weight greater than 400 g/mol. In embodiments, R2 has a molecular weight greater than 500 g/mol. In embodiments, R2 has a molecular weight greater than 600 g/mol. In embodiments, R2 has a molecular weight greater than 700 g/mol. In embodiments, R2 has a molecular weight greater than 800 g/mol. In embodiments, R2 has a molecular weight greater than 900 g/mol. In embodiments, R2 has a molecular weight less than or equal to 1000 g/mol. In embodiments, R2 has a molecular weight less than 1000 g/mol. Although not wishing to be limited by mechanism, it is believed that R2 moieties having more steric bulk than hydrogen and methyl yield improved synthetic results compared to smaller moieties, and produce fewer unwanted modifications to nucleic acids and nucleotides. See the results of Example 1 below. In embodiments, R2 is —C(R6)(R7)(R8) and R6, R7, and R8 are not all hydrogen. In embodiments, R2 is not unsubstituted methyl. In embodiments, R2 is not unsubstituted ethyl. In embodiments, R2 is not unsubstituted propyl.

Through the disclosure herein, one observes the following. R2 moieties as disclosed herein perform substantially better than do prior art reagents in driving reactions to near completion. In a 60 minute reaction performed at 25° C., for example, one observes that R2 moieties as disclosed herein exhibit starting material consumption of at least 92%, at least 93%, at least 94%, at least 95%, at least 96%, at least 97%, at least 98%, at least 99% or greater than 99% consumption of nucleotide starting material, whereas prior art approaches achieve less than 92%.

Similarly, one observes that with increasing R2 size, one sees a decreasing amount of nucleotide such as dC base degradation, such that R2 moieties as disclosed herein come to the above-mentioned completion percentages with no more than 6%, no more than 5%, no more than 4%, no more than 3%, no more than 2%, no more than 1%, or less than 1% degradation of dC.

Similarly, in some cases one sees a correlation between R2 size and reduction of nucleotide such as dC degradation. Accordingly, disclosed herein are R2 moieties having molecular weights of at least any of the following values: 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or greater than 100. In embodiments, R2 moieties are in some cases limited by solubility, such that in embodiments larger moieties become insoluble. Accordingly, in embodiments, R2 moieties are variously limited to no more than any of the following molecular weights: 1000, 900, 800, 700, 650, 600, 550, 500, 450, 400, 350, 300, 290, 280, 270, 260, 250, 240, 230, 220, 210, 200, 190, 180, 170, 160, 150, 140, 130, 120, 110, 100, or less than 100 g/mol.

R2 moieties may comprise a number of constituents, alone or in combination, to covey the benefits disclosed herein. Some R2 moieties variously comprise at least 2, at least 3, at least 4, at least 5, at least 6, or more than 6 carbon nuclei. Similarly, some R2 comprise at least one of the following: at least 1 nitrogen nucleus, at least one silicon nucleus, at least one phosphorous nucleus, at least one fluorine nucleus or at least one other constituent. R2 moieties are in some cases partially or fully fluorinated, or partially or fully hydrogenated. In some cases an R2 moiety comprises at least one component to facilitate solubility.

Alkoxyamine reagents having the structure R2-ONH₂, wherein R2 is —CH₂CH₃, —CH₂CHCH₂, and —C(CH₃)₃ are soluble in aqueous solution making them particularly useful for nucleotide synthesis and modification. Other R2 moieties that provide aqueous solubility can also be used. In some configurations, synthesis can be carried out using alkoxyamine reagents that are not soluble, or only sparingly soluble, in aqueous solutions. For example, synthesis can be carried out in non-aqueous solutions or in liquids formed by mixtures of aqueous and organic solvents. Exemplary alkoxyamine reagents that can be useful in non-aqueous or partially aqueous liquids include those having phenyl moieties and/or halogen moieties, such as:

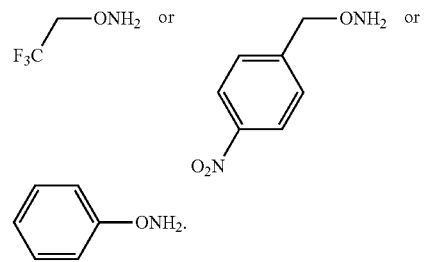

Alternately, some moieties that provide aqueous solubility might include hydroxyls, amines, carboxyls, or other hydrophilic or polar moieties.

The above alkoxyamine reagents have a primary amine in the aminooxy moiety. An alkoxyamine reagent can have a secondary amine in the aminooxy moiety. For example, an alkoxyamine reagent can have the structure

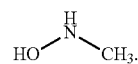

In particular configurations of the methods or compositions set forth herein, an alkoxyamine reagent having the structure R2-ONH₂ can be attached to a solid support. In embodiments, the reagent that comprises the structure R2-ONH₂ is attached to a solid support in contact with the aqueous solution. For example, the reagent can be attached via the nitrogen atom by substituting one of the hydrogens with a linkage to the solid support. A benefit of using solid support attached reagent is that the reaction will yield a solid support attached product that can be purified from reactants and other reaction components by separating the solid support from the liquid where the reaction occurred. Attachment of the reagent to the solid support can also occur via a linkage to the R2 moiety.

Generally, a solution that is used to synthesize a nucleotide having a 3'-ONH$_2$ moiety using an alkoxyamine reagent set forth herein can have a pH of 4 to 8. As the pH decreases in this range, the rate of converting the 3'-O-oxime moiety of a nucleotide to 3'-O—NH$_2$ moiety increases. However, as pH approaches the lower end of the range the risk of side reactions that cause unwanted modification to other moieties of the nucleotide also increases. Accordingly, pH for a synthetic reaction set forth herein can be in a range from 5 to 8, 6 to 8, or 7 to 8. If desired the pH can be in a range of 4 to 7, 4 to 6, or 4 to 5, as well as 5 to 7, 5 to 6, or 6 to 7, or any upper and lower range value encompassed by the range of lower and upper pH values disclosed herein. Similarly pH for a synthetic reaction set forth herein can be at least 4, at least 5, at least 6, at least 7, or no more than 8, no more than 7, no more than 6, or no more than 5.

Nucleotides having reversible terminators other than 3'-O-oxime or 3'-ONH$_2$ can be used in a method or composition herein. For example, nucleotides having different types of reversible terminators can be useful when it is desired to block a population of primers such that one or more subpopulation of the primers can be selectively deblocked. More specifically, a first subpopulation of primers can be blocked with a 3'-O-oxime or 3'-ONH$_2$ moiety and a second population can be blocked with a second type of blocking moiety. The second type of blocking moiety can, advantageously be deblocked by a method that is orthogonal to the deblocking methods set forth herein for the 3'-O-oxime or 3'-ONH$_2$ moiety. Orthogonal methods are those that do not substantially cross react. Accordingly, the 3'-O-oxime or 3'-ONH$_2$ moiety can be deblocked by a method that does not substantially deblock the second blocking moiety, and the second blocking moiety can be deblocked by a method that does not substantially deblock the 3'-O-oxime or 3'-ONH$_2$ moiety, respectively.

Examples of other types of reversible terminator moieties and their deblocking methods include, but are not limited to, the following. Useful reversible terminator moieties include those that can be chemically deblocked such as 3' azidomethyl which can be removed by phosphines, esters which can be deblocked by base hydrolysis or metal catalysts, and others set forth in U.S. Pat. Nos. 7,427,673; 7,414,116; 7,057,026; 7,544,794 or 8,034,923; or PCT publications WO 91/06678 or WO 07/123744, each of which is incorporated herein by reference. Other useful reversible terminators include 3' photoreactive moieties that can be removed by light such as those described in U.S. Pat. Nos. 7,964,352; 9,399,798 and 10,041,115 (each of which is incorporated herein by reference in its entirety), or enzymatically removable moieties such as 3' phosphate moieties that can be removed by phosphatases such as those set forth in U.S. Pat. No. 10,378,051 (which is incorporated herein by reference in its entirety).

Nucleotides having irreversible terminators can be used in a method or composition herein. For example, nucleotides having irreversible terminators can be useful when it is desired to block a population of primers such that a first subpopulation of the primers can be deblocked and a second subpopulation is resistant to deblocking. More specifically, a first subpopulation of primers can be blocked with a 3'-ONH$_2$ moiety and a second population can be blocked with an irreversible blocking moiety. Irreversible nucleotides include 2', 3'-dideoxynucleotides (ddNTPs such as ddGTP, ddATP, ddTTP, ddCTP). Dideoxynucleotides lack the 3'—OH group of dNTPs that would otherwise participate in polymerase-mediated or ligase-mediated primer extension. Thus, the 3' position has a hydrogen moiety instead of the native hydroxyl moiety.

Nucleotides that are used for particular configurations of the methods and compositions herein, for example, to participate in stabilized ternary complexes, need not include blocking groups (e.g. reversible terminators) that prevent subsequent nucleotide incorporation at the 3'-end of the primer after the analog has been incorporated into the primer. This can be the case whether or not an extension step is carried out using nucleotide(s) having a blocking group such as a reversible terminator.

A nucleotide that is a constituent of compositions herein or produced through method herein, for example, during synthesis procedures or during a sequencing process, can optionally include an exogenous label. An exogenously labeled nucleotide can include a reversible or irreversible terminator moiety, an exogenously labeled nucleotide can be non-incorporable, an exogenously labeled nucleotide can lack terminator moieties, an exogenously labeled nucleotide can be incorporable or an exogenously labeled nucleotide can be both incorporable and non-terminated. An exogenously labeled nucleotide can be a moiety in a nucleic acid, for example, being the 3' nucleotide of a primer. Exogenously labeled nucleotides can be particularly useful in a Sequencing By Binding™ process when used to form a stabilized ternary complex with a non-labeled polymerase. Exogenously labeled nucleotides can be useful in a sequencing by synthesis process when incorporated into a primer by polymerase.

Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore labels include, but are not limited to rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; Malachite green; CY dyes (GE Biosciences), including Cy3 (and its derivatives), Cy5 (and its derivatives) and Cy7 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (borondipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610, ATTO 635; ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED, EPOCH YAKIMA YELLOW, EPOCH GIG HARBOR GREEN; Tokyo green (M. Kamiya, et al., 2005 *Angew. Chem. Int. Ed.* 44:5439-5441); and CF dyes including CF 647 and CF555 (Biotium), and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland. In embodiments, an exogenous label is a detectable moiety. In embodiments, an exogenous label is a detectable agent.

An exogenous label can be attached to a nucleotide or nucleic acid via a linker. A linker that is present in a nucleotide or nucleic acid can be, but need not be, cleavable. For example, the exogenous label can be attached to the nucleobase of a nucleotide or nucleic acid via a linker and the linker can be inert to an alkoxyamine reagent having formula $R2-ONH_2$ and or the linker can be inert to nitrous acid (HONO). The linker can be stable to conditions used in methods set forth herein such that the covalent structure of the linker is not changed during any particular step, or throughout all steps, of a method set forth herein. Alternatively, the linker that attaches an exogenous label to a nucleobase can be reactive with an alkoxyamine reagent having formula $R2-ONH_2$ such that the reaction detaches the exogenous label from the nucleobase. For example, the linker can include a moiety having the structure:

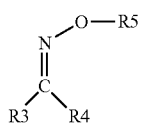

wherein at least one of R3, R4 or R5 is attached to the exogenous label directly or via a second moiety of the linker and wherein at least one of R3, R4 or R5 is attached to the nucleobase directly or via a third moiety of the linker. Another useful linker moiety is a hydrazone. For example, the linker can include a moiety having the structure:

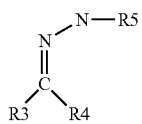

wherein at least one of R3, R4 or R5 is attached to the exogenous label directly or via a second moiety of the linker and wherein at least one of R3, R4 or R5 is attached to the nucleobase directly or via a third moiety of the linker. These linker moieties can be reacted with an $R2-ONH_2$ molecule to cleave the exogenous label from the nucleobase. In embodiments, B, Base, R3, R4, R5, R6, R7, or R8 may independently include an exogenous label. In embodiments, B, Base, R3, R4, R5, R6, R7, or R8 may independently include a label. In embodiments, B, Base, R3, R4, R5, R6, R7, or R8 may independently include a detectable moiety. In embodiments, B, Base, R3, R4, R5, R6, R7, or R8 may independently include a fluorphore moiety. In embodiments, R3, R4, R5, R6, R7, or R8 independently is an exogenous label. In embodiments, R3, R4, R5, R6, R7, or R8 independently is a label. In embodiments, R3, R4, R5, R6, R7, or R8 independently is a detectable moiety. In embodiments, R3, R4, R5, R6, R7, or R8 independently is a fluorphore moiety. In embodiments, the blocking moiety is an exogenous label moiety. In embodiments, the blocking moiety includes an exogenous label moiety. In embodiments, the protecting moiety is an exogenous label moiety. In embodiments, the protecting moiety includes an exogenous label moiety.

R5 is independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof, or an exogenous label moiety.

In embodiments, a substituted R5 (e.g., substituted alkyl, substituted alkenyl, substituted alkynyl, substituted cycloalkyl, substituted cycloalkenyl, substituted cycloalkynyl, substituted aryl, substituted heteroaryl, substituted heteroalicyclyl, substituted aralkyl, substituted heteroaralkyl, and/or substituted (heteroalicyclyl)alkyl) is substituted with at least one substituent group, size-limited substituent group, or lower substituent group; wherein if the substituted R5 is substituted with a plurality of groups selected from substituent groups, size-limited substituent groups, and lower substituent groups; each substituent group, size-limited substituent group, and/or lower substituent group may optionally be different. In embodiments, when R5 is substituted, it is substituted with at least one substituent group. In embodiments, when R5 is substituted, it is substituted with at least one size-limited substituent group. In embodiments, when R5 is substituted, it is substituted with at least one lower substituent group.

In embodiments, R5 is independently H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. In embodiments, R5 is independently an exogenous label moiety.

In alternative embodiments, a nucleotide, nucleic acid, reactant for a method set forth herein or product of a method set forth herein can lack exogenous labels. For example, a nucleic acid, nucleotide, polymerase and/or stabilized ternary complex can lack one, several or all of the exogenous labels described herein or in the references that are cited and incorporated herein. For example, a non-labeled ternary complex can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. Nos. 2017/0191125 A1 or 2017/0022553 A1; or U.S. Pat. No. 10,246,744, each of which is incorporated herein by reference.

In embodiments, the nucleobase includes an exogenous label moiety (e.g., connected to the nucleobase through a linker, a fluorophore moiety, an antigen for antibody recognition). In embodiments, the nucleobase is substituted with an exogenous label moiety (e.g., connected to the nucleobase through a linker, a fluorophore moiety, an antigen for antibody recognition). In embodiments, the nucleobase is covalently bonded to the exogenous label moiety through a linker. In embodiments, the linker includes

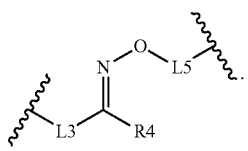

In embodiments, the linker includes

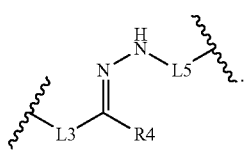

In embodiments, the linker is

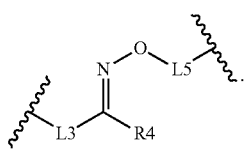

In embodiments, the linker is

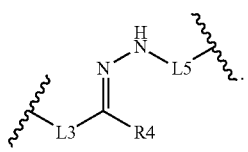

L3 and L5 are each independently a covalent linker. In embodiments, L5 is bonded to a nucleobase. In embodiments, L3 is bonded to a nucleobase. In embodiments L5 is bonded to an exogenous label moiety. In embodiments, L3 is bonded to an exogenous label moiety. In embodiments, L5 is -L5A-L5B-L5C-L5D-L5E-. In embodiments, L3 is -L3A-L3B-L3C-L3D-L3E-. In embodiment, the linker connecting the nucleobase to the exogenous label moiety is -L6-L7-L8-L9-L10-. L3A, L3B, L3C, L3D, L3E, L5A, L5B, L5C, L5D, L5E, L6, L7, L8, L9, and L10 are independently a bond, —NH—, —O—, —S—, —SO$_2$—, —C(O)—, —C(O)NH—, —NHC(O)—, —NHC(O)NH—, —C(O)O—, —OC(O)—, —SO$_2$NH—, —NHSO$_2$—, substituted or unsubstituted alkylene (e.g., C$_1$-C$_8$, C$_1$-C$_6$, or C$_1$-C$_4$), substituted or unsubstituted alkenylene (e.g., C$_2$-C$_8$, C$_2$-C$_6$, or C$_2$-C$_4$), substituted or unsubstituted alkynylene (e.g., C$_2$-C$_8$, C$_2$-C$_6$, or C$_2$-C$_4$), substituted or unsubstituted heteroalkylene (e.g., 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted cycloalkenylene (e.g., C$_3$-C$_8$, C$_3$-C$_6$, or C$_5$-C$_6$), substituted or unsubstituted cycloalkynylene (e.g., C$_3$-C$_8$, C$_3$-C$_6$, or C$_5$-C$_6$), substituted or unsubstituted arylene (e.g., C$_6$-C$_{10}$ aryl, C$_{10}$ aryl, or phenylene), substituted or unsubstituted heteroarylene (e.g., 5 to 10 membered, 5 to 9 membered, or 5 to 6 membered), substituted or unsubstituted heteroalicyclylene (e.g., 3 to 8 membered, 3 to 6 membered, or 5 to 6 membered), substituted or unsubstituted aralkylene, substituted or unsubstituted heteroaralkylene, or substituted or unsubstituted (heteroalicyclyl)alkylene.

In embodiments, L3 is substituted. In embodiments, L3 is unsubstituted. In embodiments, a substituted L3 (e.g., a substituted covalent linker) is substituted with at least one substituent group, size-limited substituent group, or lower substituent group; wherein if the substituted L3 is substituted with a plurality of groups selected from substituent groups, size-limited substituent groups, and lower substituent groups; each substituent group, size-limited substituent group, and/or lower substituent group may optionally be different. In embodiments, when L3 is substituted, it is substituted with at least one substituent group. In embodiments, when L3 is substituted, it is substituted with at least one size-limited substituent group. In embodiments, when L3 is substituted, it is substituted with at least one lower substituent group.

In embodiments, L5 is substituted. In embodiments, L5 is unsubstituted. In embodiments, a substituted L5 (e.g., a substituted covalent linker) is substituted with at least one substituent group, size-limited substituent group, or lower substituent group; wherein if the substituted L5 is substituted with a plurality of groups selected from substituent groups, size-limited substituent groups, and lower substituent groups; each substituent group, size-limited substituent group, and/or lower substituent group may optionally be different. In embodiments, when L5 is substituted, it is substituted with at least one substituent group. In embodiments, when L5 is substituted, it is substituted with at least one size-limited substituent group. In embodiments, when L5 is substituted, it is substituted with at least one lower substituent group.

In embodiments, a substituted L3A (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L3A is substituted with a plurality of groups selected from substituent groups, size-limited substituent groups, and lower substituent groups; each substituent group, size-limited substituent group, and/or lower substituent group may optionally be different. In embodiments, when L3A is substituted, it is substituted with at least one substituent group. In embodiments, when L3A is substituted, it is substituted with at least one size-limited substituent group. In embodiments, when L3A is substituted, it is substituted with at least one lower substituent group.

In embodiments, a substituted L3B (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L3B is substituted with a plurality of groups selected from substituent groups, size-limited substituent groups, and lower substituent groups; each substituent group, size-limited substituent group, and/or lower substituent group may optionally be different. In embodiments, when L3B is substituted, it is substituted with at least one substituent group. In embodiments, when L3B is substituted, it is substituted with at least one size-limited substituent group. In embodiments, when L3B is substituted, it is substituted with at least one lower substituent group.

In embodiments, a substituted L3C (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L3C is substituted with a plurality of groups selected from substituent groups, size-limited substituent groups, and lower substituent groups; each substituent group, size-limited substituent group, and/or lower substituent group may optionally be different. In embodiments, when L3C is substituted, it is substituted with at least one substituent group. In embodiments, when L3C is substituted, it is substituted with at least one size-limited substituent group. In embodiments, when L3C is substituted, it is substituted with at least one lower substituent group.

In embodiments, a substituted L3D (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L3D is substituted with a plurality of groups selected from substituent groups, size-limited substituent groups, and lower substituent groups; each substituent group, size-limited substituent group, and/or lower substituent group may optionally be different. In embodiments, when L3D is substituted, it is substituted with at least one substituent group. In embodiments, when L3D is substituted, it is substituted with at least one size-limited substituent group. In embodiments, when L3D is substituted, it is substituted with at least one lower substituent group.

In embodiments, a substituted L3E (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L3E is substituted with a plurality of groups selected from substituent groups, size-limited substituent groups, and lower substituent groups; each substituent group, size-limited substituent group, and/or lower substituent group may optionally be different. In embodiments, when L3E is substituted, it is substituted with at least one substituent group. In embodiments, when L3E is substituted, it is substituted with at least one size-limited substituent group. In embodiments, when L3E is substituted, it is substituted with at least one lower substituent group.

In embodiments, a substituted L5A (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L5A is substituted with a plurality of groups selected from substituent groups, size-limited substituent groups, and lower substituent groups; each substituent group, size-limited substituent group, and/or lower substituent group may optionally be different. In embodiments, when L5A is substituted, it is substituted with at least one substituent group. In embodiments, when L5A is substituted, it is substituted with at least one size-limited substituent group. In embodiments, when L5A is substituted, it is substituted with at least one lower substituent group.

In embodiments, a substituted L5B (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L5B is substituted with a plurality of groups selected from substituent groups, size-limited substituent groups, and lower substituent groups; each substituent group, size-limited substituent group, and/or lower substituent group may optionally be different. In embodiments, when L5B is substituted, it is substituted with at least one substituent group. In embodiments, when L5B is substituted, it is substituted with at least one size-limited substituent group. In embodiments, when L5B is substituted, it is substituted with at least one lower substituent group.

In embodiments, a substituted L5C (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L5C is substituted with a plurality of groups selected from substituent groups, size-limited substituent groups, and lower substituent groups; each substituent group, size-limited substituent group, and/or lower substituent group may optionally be different. In embodiments, when L5C is substituted, it is substituted with at least one substituent group. In embodiments, when L5C is substituted, it is substituted with at least one size-limited substituent group. In embodiments, when L5C is substituted, it is substituted with at least one lower substituent group.

In embodiments, a substituted L5D (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L5D is substituted with a plurality of groups selected from substituent groups, size-limited substituent groups, and lower substituent groups; each substituent group, size-limited substituent group, and/or lower substituent group may optionally be different. In embodiments, when L5D is substituted, it is substituted with at least one substituent group. In embodiments, when L5D is substituted, it is substituted with at least one size-limited substituent group. In embodiments, when L5D is substituted, it is substituted with at least one lower substituent group.

In embodiments, a substituted L5E (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L5E is substituted with a plurality of groups selected from substituent groups, size-limited substituent groups, and lower substituent groups; each substituent group, size-limited substituent group, and/or lower substituent group may optionally be different. In embodiments, when L5E is substituted, it is substituted with at least one substituent group. In embodiments, when L5E is substituted, it is substituted with at least one size-limited substituent group. In embodiments, when L5E is substituted, it is substituted with at least one lower substituent group.

In embodiments, a substituted L6 (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L6 is substituted with a plurality of groups selected from substituent groups, size-limited substituent groups, and lower substituent groups; each substituent group, size-limited substituent group, and/or lower substituent group may optionally be different. In embodiments, when L6 is substituted, it is substituted with at least one substituent group. In embodiments, when L6 is substituted, it is substituted with at least one size-limited substituent group. In embodiments, when L6 is substituted, it is substituted with at least one lower substituent group.

In embodiments, a substituted L7 (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L7 is substituted with a plurality of groups selected from substituent groups, size-limited substituent groups, and lower substituent groups; each substituent group, size-limited substituent group, and/or lower substituent group may optionally be different. In embodiments, when L7 is substituted, it is substituted with at least one substituent group. In embodiments, when L7 is substituted, it is substituted with at least one size-limited substituent group. In embodiments, when L7 is substituted, it is substituted with at least one lower substituent group.

In embodiments, a substituted L8 (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L8 is substituted with a plurality of groups selected from substituent groups, size-limited substituent groups, and lower substituent groups; each substituent group, size-limited substituent group, and/or lower substituent group may optionally be different. In embodiments, when L8 is substituted, it is substituted with at least one substituent group. In embodiments, when L8 is substituted, it is substituted with at least one size-limited substituent group. In embodiments, when L8 is substituted, it is substituted with at least one lower substituent group.

In embodiments, a substituted L9 (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L9 is substituted with a plurality of groups selected from substituent groups, size-limited substituent groups, and lower substituent groups; each substituent group, size-limited substituent group, and/or lower substituent group may optionally be different. In embodiments, when L9 is substituted, it is substituted with at least one substituent group. In embodiments, when L9 is substituted, it is substituted with at least one size-limited substituent group. In embodiments, when L9 is substituted, it is substituted with at least one lower substituent group.

In embodiments, a substituted L10 (e.g., substituted alkylene, substituted alkenylene, substituted alkynylene, substituted heteroalkylene, substituted cycloalkylene, substituted cycloalkenylene, substituted cycloalkynylene, substituted arylene, substituted heteroarylene, substituted heteroalicyclylene, substituted aralkylene, substituted heteroaralkylene, and/or substituted (heteroalicyclyl)alkylene) is substituted with at least one substituent group, size-limited substituent group, or lower substituent group; wherein if the substituted L10 is substituted with a plurality of groups selected from substituent groups, size-limited substituent groups, and lower substituent groups; each substituent group, size-limited substituent group, and/or lower substituent group may optionally be different. In embodiments, when L10 is substituted, it is substituted with at least one substituent group. In embodiments, when L10 is substituted, it is substituted with at least one size-limited substituent group. In embodiments, when L10 is substituted, it is substituted with at least one lower substituent group.

Alternatively, a nucleotide that is used herein, for example, for extension of a primer or to participate in forming a ternary complex can lack exogenous labels (i.e. the nucleotide can be "non-labeled"). A non-labeled nucleotide can include a reversible terminator such as a 3'-$ONH_2$ moiety or an irreversible terminator moiety. A non-labeled nucleotide can be non-incorporable, a non-labeled nucleotide can lack terminator moieties, a non-labeled nucleotide can be incorporable, or a non-labeled nucleotide can be both incorporable and non-terminated. Non-labeled nucleotides can be useful, for example, in a Sequencing By Binding™ (SBB™) process when a label on a polymerase is used to detect a stabilized ternary complex or when label-free detection is used. Non-labeled nucleotides can also be useful in an extension step of a SBB™ method or other method set forth herein. It will be understood that absence of a moiety or function for a nucleotide refers to the nucleotide having no such function or moiety. However, it will also be understood that one or more of the functions or moieties set forth herein for a nucleotide, or analog thereof, or otherwise known in the art for a nucleotide, or analog thereof, can be specifically omitted in a method or composition set forth herein.

The nucleobase of a nucleotide can be a purine or pyrimidine. For example, the nucleobase can be a canonical or primary nucleobase such as adenine, cytosine, guanine, thymine, or uracil. Other nucleobases can be useful such as those that are complementary to one or more of the primary or canonical nucleobases. In embodiments, the nucleobase is complementary to adenine, cytosine, guanine, thymine, or uracil. Modified nucleotides can be used, for example, methylated nucleobases such as 5-methylcytosine or 7-methylguanosine, or hydroxylated and methylated nucleobases such as 5-hydroxymethylcytosine. Other useful nucleobases include, for example, hypoxanthine, xanthine, inosine, isoguanine or isocytosine. Isoguanine and isocytosine can be particularly useful since they are complementary to each other, and specific for each other so as to form a third base pair when compared to the two native base pairs, Adenine:Thymine and Cytosine:Guanine. A particularly useful nucleobase is 7-deazaguanine, which can provide a convenient nucleobase for synthetic procedures that attach a label to the nucleobase while also being capable of pairing with cytosine when the labeled nucleobase is present in a nucleic acid strand. In embodiments, the nucleobase is independently 5-methylcytosine, hypoxanthine, xanthine, inosine, isoguanine, isocytosine, or 7-deazaguanine. In embodiments, the nucleobase (e.g., B, Base) includes an exogenous label (e.g., detectable moiety, fluorophore moiety, antigen) optionally bonded directly to the nucleobase or optionally bonded through a linker (e.g., L5).

The sugar moiety of a nucleotide can be a deoxyribose, ribose or analog thereof. For example, a nucleotide can have one of the following structures:

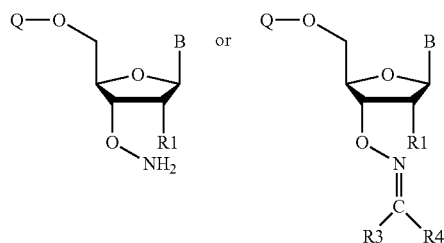

wherein R1 is H, B is a nucleobase and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. This deoxyribonucleotide can be in a monomeric form whereby Q is a hydrogen, exogenous protecting moiety, or at least one phosphate (e.g. monophosphate, diphosphate, triphosphate or greater than three phosphates, any of the preceding which can be substituted or unsubstituted). Alternatively, the nucleotide can be a moiety of a nucleic acid, for example, wherein Q is a deoxyribonucleic acid (DNA). The DNA can be single stranded or double stranded. In configurations in which the DNA is double stranded the nucleotide can be a moiety of a primer strand, for example, being at the 3' end of the primer, or the nucleotide moiety can be in the template strand. The nucleotide can be a moiety of a nucleic acid that is a mixed hybrid formed by strands having different backbones such as a DNA:RNA hybrid, DNA:PNA hybrid, RNA:PNA hybrid or the like (wherein PNA is peptide nucleic acid).

Alternatively, the sugar moiety of a nucleotide can have one of the following structures:

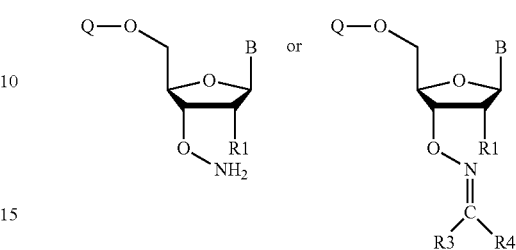

wherein R1 is OH, B is a nucleobase and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. This ribonucleotide can be in a monomeric form whereby Q is at least one phosphate (e.g. monophosphate, diphosphate, triphosphate or greater than three phosphates, any of the preceding which can be substituted or unsubstituted). Alternatively, the nucleotide can be a moiety of a nucleic acid, for example, wherein Q is a ribonucleic acid (RNA). The RNA can be single stranded or double stranded. In configurations in which the RNA is double stranded the nucleotide can be a moiety of a primer strand, for example, being at the 3' end of the primer, or the nucleotide moiety can be in the template strand. The nucleotide can be a moiety of a nucleic acid that is a mixed hybrid formed by strands having different backbones such as a DNA:RNA hybrid, DNA:PNA hybrid, RNA:PNA hybrid or the like (wherein PNA is peptide nucleic acid).

Nucleic acids that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs such as PNA or others known in the art can also be used herein. Nucleic acid primers, probes or templates can be DNA, RNA or analogs thereof.

A nucleic acid may be single stranded or double stranded. A double stranded nucleic acid may possess a single-stranded nick or a gap. Where double-stranded, a nucleic acid molecule can be blunt-ended or have an overhang (e.g. 5' overhang or 3' overhang). Such nucleic acid molecules can be produced by any chemical or enzymatic method known in the art. Examples of such methods include phosphoramidite synthesis or replication in vivo or in vitro. A nucleic acid of the present disclosure can be linear (e.g. having free 3' and 5' ends) or it can be circular (e.g. lacking 5' and 3' ends)

Deoxyribonucleic acid (DNA) is a particularly useful nucleic acid. The DNA can be single- or double-stranded deoxyribonucleic acid. Deoxyribonucleotides are typically joined by phosphodiester bonds, although in some cases, nucleic acid analogs are included that may have alternate backbones, such as, phosphoramide (e.g. Beaucage, et al., *Tetrahedron*, 49 (10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470

(1988); and Pauwels, et al., *Chemica Scripta*, 26:141 (1986)), phosphorothioate (e.g. Mag, et al., *Nucleic Acids Res.*, 19:1437 (1991); and U.S. Pat. No. 5,644,048), phosphorodithioate (e.g. Briu, et al., *J. Am. Chem. Soc.*, 111:2321 (1989)), O-methylphophoroamidite linkages (e.g. Eckstein, *Oligonucleotides and Analogues: A Practical Approach*, Oxford University Press), and peptide nucleic acid (PNA) backbones and linkages (e.g. Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996)). Other analog nucleic acids include those with positive backbones (e.g. Denpcy, et al., *Proc, Natl. Acad. Sci. USA*, 92:6097 (1995)); non-ionic backbones (e.g. U.S. Pat. Nos. 5,386,023; 5,637,684; 5,602,240; 5,216, 141; and U.S. Pat. No. 4,469,863; Kiedrowski, et al., *Angew. Chem. Intl. Ed.* English, 30:423 (1991); Letsinger, et al., *J. Am. Chem. Soc.*, 110:4470 (1988); Letsinger, et al., *Nucleosides & Nucleotides*, 13:1597 (1994); Chapters 2 and 3, *ASC Symposium Series* 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including for example, those described in U.S. Pat. Nos. 5,235,033 and 5,034,506, and Chapters 6 and 7, *ACS Symposium Series* 580, "Carbohydrate Modifications in Antisense Research", Ed. Y. S. Sanghui and P. Dan Cook. Nucleic acids containing one or more carbocyclic sugars are also included within the definition of nucleic acids (e.g. Jenkins, et al., *Chem. Soc. Rev.*, (1995) pp. 169 176). Several nucleic acid analogs are described in Rawls, C & E News, Jun. 2, 1997, page 35. All of these references are hereby expressly incorporated by reference. These modifications of the ribose-phosphate backbone may be present to facilitate the addition of exogenous moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acid analogs and non-natural analogs may be made.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; an aplicomplexan alveolate pathogen such as *Plasmodium falciparum*; an environmental sample; or any other eukaryotic, eubacterial or archaeal source. Nucleic acids can also be derived from a eubacterial prokaryote such as a bacterium, *Escherichia coli*, Staphylococci or *Mycoplasma pneumoniae*; an archaean prokaryote; a virus such as Hepatitis C virus, a coronavirus, or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference. Cells, tissues, biological fluids, proteins and other samples can be obtained from these organisms and used in a composition, apparatus or method set forth herein.

A nucleic acid can be obtained from a preparative method such as genome isolation, genome fragmentation, gene cloning and/or amplification. The nucleic acid can be obtained from an amplification technique such as polymerase chain reaction (PCR), rolling circle amplification (RCA), multiple displacement amplification (MDA) or the like. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

In some configurations of the methods and compositions set forth herein, a single nucleotide or single nucleic acid molecule can be manipulated, modified or detected. The single nucleotide or single nucleic acid molecule can be in solution phase, or solid phase (e.g. attached to a surface). In some configurations, the single molecule is subjected to detection under conditions wherein individual molecules are resolved one from the other (e.g. single molecule sequencing). Alternatively, multiple nucleotides of a particular type or multiple copies of a nucleic acid can be made or used. The resulting ensemble can be manipulated, modified or detected, for example, in a nucleic acid sequencing protocol. For example, a nucleic acid can be amplified in solution or on a surface (e.g. on the inner wall of a flow cell) using techniques set forth in further detail below.

In multiplex embodiments, multiple different nucleic acid molecules (i.e. a population having a variety of different sequences) are manipulated or detected. The molecules can optionally be attached to a surface in a flow cell or other vessel. The nucleic acids can be attached at unique sites on the surface and single nucleic acid molecules that are spatially distinguishable one from the other can be manipulated, modified or detected in parallel. Alternatively, the nucleic acids can be amplified on the surface to produce a plurality of surface attached ensembles. The ensembles can be spatially distinguishable from each other and manipulated, modified or detected in parallel.

A method set forth herein can use any of a variety of nucleic acid amplification techniques. Exemplary techniques that can be used include, but are not limited to, polymerase chain reaction (PCR), rolling circle amplification (RCA), multiple displacement amplification (MDA), bridge amplification, or random prime amplification (RPA). In particular configurations, one or more primers used for amplification can be attached to a surface in a flow cell. In such embodiments, extension of the surface-attached primers along template nucleic acids will result in complementary copies of the templates being attached to the surface. Such amplification methods can be used for analytical purposes such as real time PCR or quantitative PCR. Alternatively, amplification can be used to prepare nucleic acids for downstream applications such as nucleic acid sequencing. Preparative amplification methods that result in one or more sites on a solid support, where each site is attached to multiple copies of a particular nucleic acid template, can be referred to as "clustering" methods. Primers that are used for DNA amplification techniques can include a 3'-O-oxime moiety to be converted to a reversible terminator moiety as disclosed herein, or a 3'-ONH$_2$ or other reversible terminator moiety as disclosed herein such that deprotection methods set forth herein can be used to generate a reversibly terminated primer suitable for deblocking so as to initiate extension or to control extension at one or more points in an amplification reaction.

In PCR techniques, one or both primers used for amplification can be attached to a surface. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. Nos. 5,641,658 or 7,115,400; U.S. Patent Pub. Nos. 2002/0055100 A1, 2004/0096853 A1, 2004/0002090 A1, 2007/0128624 A1 or 2008/0009420 A1, each of which is incorporated herein by reference. PCR amplification can also be carried out with one of the amplification primers attached to the surface and the second primer in solution. An exemplary format that uses a combination of one solid phase-attached primer and a solution phase primer is known as primer walking and can be carried out as described in U.S. Pat. No. 9,476,080, which is incorporated herein by reference. Another example is emulsion PCR which can be carried out as described, for example, in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference. One or both of the primers used in a PCR technique can include a 3'-O-oxime moiety or 3'-ONH$_2$ moiety, for example, prior to initiation of amplification or at a point where amplification is to be stopped or paused. Amplification can proceed by deblocking the 3' position using a method set forth herein.

RCA techniques can be used in a method set forth herein. Exemplary reagents that can be used in an RCA reaction and methods by which RCA can produce amplicons are described, for example, in Lizardi et al., *Nat. Genet.* 19:225-232 (1998) or US Pat. App. Pub. No. 2007/0099208 A1, each of which is incorporated herein by reference. Primers used for RCA can be in solution or attached to a surface in a flow cell. The primers can optionally include a 3'-O-oxime moiety or 3'-ONH$_2$ moiety, for example, prior to initiation of amplification or at a point where amplification is to be stopped or paused. Amplification can proceed by deblocking the 3' position using a method set forth herein.

MDA techniques can also be used in a method of the present disclosure. Some reagents and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); or U.S. Pat. Nos. 5,455,166; 5,130,238; or 6,214,587, each of which is incorporated herein by reference. Primers used for MDA can be in solution or attached to a surface in a flow cell. The primers can optionally include a 3'-O-oxime moiety or 3'-ONH$_2$ moiety, for example, prior to initiation of amplification or at a point where amplification is to be stopped or paused. Amplification can proceed by deblocking the 3' position using a method set forth herein.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Primers used herein can be DNA, RNA or analogs thereof.

A nucleic acid that is used in a method or composition herein can be linear, for example, being flanked by a 3' end and a 5' end. Alternatively, a nucleic acid can be circular, thereby lacking a 3' and 5' end. Whether linear, circular or in any other conformation, a nucleic acid that is used herein can have a size that is desired for a particular use or that is a result of manipulations carried out on the nucleic acid. For example, a nucleic acid can have a length that is at least 50 bases, 100 bases, $1\times10^3$ bases, $1\times10^4$ bases, $1\times10^5$ bases, $1\times10^6$ bases or longer. Alternatively or additionally, the nucleic acid length can be at most $1\times10^6$ bases, $1\times10^5$ bases, $1\times10^4$ bases, $1\times10^3$ bases, 100 bases, 50 bases or shorter. When a population of nucleic acids is used, the average length for the population can have a lower and/or upper limit selected from those ranges.

A nucleotide can be attached to a solid support. The nucleotide can be in monomeric form or it can be a moiety of a nucleic acid. Typically, the nucleotide will be attached to the solid support via a moiety other than the 3' position. As such the 3' position can be blocked or deblocked as set forth herein. Accordingly, the nucleotide although being attached to a solid support can be in contact with a solution. The solution can contain reagents for blocking or deblocking the solid-phase nucleotide. By way of example, the attached nucleotide can have one of the following structures:

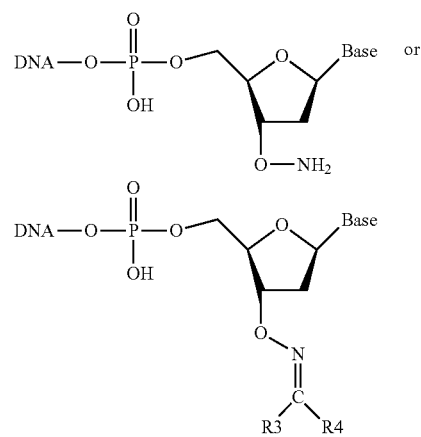

wherein Base is a nucleobase, and wherein DNA is independently a single stranded deoxyribonucleic acid or double stranded deoxyribonucleic acid. Optionally, the nucleotide can be attached to the solid support via the DNA. Alternatively, the sugar can be a ribose instead of deoxyribose, and the nucleotide can be at the 3' end of RNA instead of DNA. In this case the RNA can be single stranded or double stranded. Optionally, the nucleotide can be attached to the solid support via the RNA.

In embodiments, a substituted Base (e.g., a substituted nucleobase) is substituted with at least one substituent group, size-limited substituent group, or lower substituent group; wherein if the substituted Base is substituted with a plurality of groups selected from substituent groups, size-limited substituent groups, and lower substituent groups; each substituent group, size-limited substituent group, and/or lower substituent group may optionally be different. In embodiments, when Base is substituted, it is substituted with at least one substituent group. In embodiments, when Base is substituted, it is substituted with at least one size-limited substituent group. In embodiments, when Base is substituted, it is substituted with at least one lower substituent group.

A particularly useful solid support is an array. Arrays provide an advantage of multiplex processing of analytes, whereby the multiple different types of analytes are manipulated or detected in parallel. Although it is also possible to serially process different types of analytes using methods or compositions set forth herein, parallel processing can provide cost savings, time savings and uniformity of assay conditions. An array can include at least 2, 10, 100, $1 \times 10^3$, $1 \times 10^4$, $1 \times 10^5$, $1 \times 10^6$, $1 \times 10^9$, or more different analyte sites. Alternatively or additionally, an array can include at most $1 \times 10^9$, $1 \times 10^6$, $1 \times 10^5$, $1 \times 10^4$, $1 \times 10^3$, 100, 10, 2 or fewer, different analyte sites.

An array can be attached to an inner surface of a vessel (e.g. the inner wall of a flow cell) or to a solid support inside of a vessel (e.g. a bead or other solid support inside of a flow cell). The vessel or solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The material can be selected based on properties desired for a particular use. For example, materials that are transparent to a desired wavelength of radiation are useful for analytical techniques that will utilize radiation at that wavelength. Conversely, it may be desirable to select a material that does not pass radiation of a certain wavelength (e.g. being opaque, absorptive or reflective). Other properties of a material that can be exploited are inertness or reactivity to reagents used in a downstream process, such as those set forth herein, or ease of manipulation, or low cost of manufacture.

A particularly useful solid support for use in a flow cell or other vessel is a particle such as a bead or microsphere. Populations of beads can be used for attachment of populations of analytes such as nucleotides, nucleic acids, reversibly terminated primers, deblocked primers, extendable primers, polymerases, stabilized ternary complexes or the like. In some configurations, each bead has a single type of stabilized ternary complex, a single type of component capable of forming the complex, or a single type of some other analyte set forth herein or in references cited herein. For example, an individual bead can be attached to a single type of ternary complex, a single type of template allele, a single type of template locus, a single type of primer, single type of reversibly terminated primer, single type of deblocked primer, single type of extendable primer, or a single type of nucleotide. Alternatively, different types of components need not be separated on a bead-by-bead basis. As such, a single bead can bear multiple different types of: ternary complexes, template nucleic acids, primers (whether blocked or extendable), primed template nucleic acids (whether the primers are blocked or extendable) and/or nucleotides (whether blocked or extendable). The composition of a bead can vary, depending for example, on the format, chemistry and/or method of attachment to be used. Exemplary bead compositions include solid supports, and chemical functionalities thereon, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, controlled pore glass (CPG), latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

Beads can have a symmetrical shape, such as spherical, polyhedral, cylindrical or the like. Alternatively, beads can have an irregular or non-symmetric shape. Exemplary sizes for beads used herein can have average diameter that is at least about nm, 100 nm, 1 µm, 5 µm, 10 µm, 100 µm, 1 mm or larger. Alternatively or additionally, beads used herein can have average diameter that is at most about 1 mm, 100 µm, 10 µm, 5 µm, 1 µm, 100 nm, 10 nm, 1 nm or smaller. Beads in these size ranges can be used as array features or as particles in a fluid.

Exemplary compositions and techniques that can be used to make an array of beads include, without limitation, those used for BeadChip™ Arrays available from Illumina, Inc. (San Diego, Calif.) those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

Other useful arrays include those that are used in nucleic acid sequencing applications. For example, arrays that are used to immobilize amplicons of genomic fragments (often referred to as clusters) can be particularly useful. Examples of nucleic acid sequencing arrays that can be used herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference. Arrays formed on flow cells used for commercial sequencing platforms, such as those developed by Illumina (San Diego, Calif.), Life Technologies (a subsidiary of Thermo Fisher, Waltham Mass.), Pacific Biosciences (Menlo Park, Calif.), MGI (a subsidiary of BGI, Shenzhen, Guangdong, China), can also be useful.

A nucleic acid or other analyte can be attached to a support in a way that provides detection at a single molecule level or at an ensemble level. For example, a plurality of different nucleic acids can be attached to a solid support in a way that an individual nucleic acid molecule that is in a blocked or deblocked state on the support can be distinguished from all neighboring nucleic acid molecules on the support. As such, one or more different templates can be attached to a solid support in a format where each single molecule template is physically isolated and detected in a way that the single molecule is resolved from all other molecules on the solid support, for example, in a sequencing process set forth herein.

Alternatively, a composition or method of the present disclosure can employ one or more ensembles, an ensemble being a population of analytes of the same type such as a population of nucleic acids having a common template sequence. Cluster methods can be used to attach one or more nucleic acid ensembles to a solid support. As such, an array can have a plurality of ensembles, each of the ensembles being referred to as a cluster or array site in that format. Clusters can be formed using methods known in the art such as bridge amplification, emulsion PCR or other methods set forth herein. The nucleic acids in a cluster can include a reversibly terminated nucleotide, deblocked nucleotide or extendable nucleotide A system of the present disclosure can be configured to use a flow cell. The flow cell can include a detection channel where an analytical reaction of interest can be observed. The analytical reaction can occur in solution phase within the flow cell. Alternatively, an analytical reaction can occur on a solid support within the detection channel. For example, a reagent solution can be flowed over a solid support that is attached to analytes of interest, such as nucleic acids, and a resulting reaction can be observed on the solid support. Nucleic acids that are present in a flow cell, whether surface attached or not, can include a 3' nucleotide that is reversibly terminated, deblocked or extendable. A flow cell allows convenient fluidic manipulation by passing solutions through an ingress opening, into the detection channel and out of the interior via an egress opening. For example, the detection channel can have an observation area or volume such as an optically transparent window through which optical signals can be observed, an electrical contact through which electronic signals can be observed or the like. A particularly useful flow cell has a window that is transparent to excitation radiation and emission radiation used for luminescence detection. Exemplary flow cells that can be used herein are described, for example, in US Pat. App. Pub. No. 2010/0111768 A1, WO 05/065814 or US Pat. App. Pub. No. 2012/0270305 A1, each of which is incorporated herein by reference.

The present disclosure provides a method for sequencing a nucleic acid. The method can be carried out on a primed template nucleic acid in which the primer has a 3' $ONH_2$ reversible terminator moiety that is reacted with a deblocking reagent having nitrous acid (HONO), thereby converting the primer to an extendable primer having a 3' hydroxyl moiety. In some configurations, the reversibly terminated primer can have the following structure:

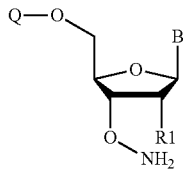

wherein B is a nucleobase; R1 is independently halogen, $OCH_3$, H or OH; and Q is a nucleic acid primer.

Alternatively, a sequencing method can be carried out on a primed template nucleic acid in which the primer has a 3'-O-oxime protecting moiety that is removed by treatment with a reagent having the structure R2-$ONH_2$ or other reversible terminator and, thereby converting the primer to a reversibly terminated primer which can then be converted to an extendable primer having a 3' hydroxyl moiety by, for example, reaction with nitrous acid (HONO). Alternatively, a sequencing method can be carried out on a primed template nucleic acid in which the primer has a 3'-O-oxime reversible terminator moiety that is deblocked by treatment with a reagent having the structure R2-$ONH_2$ and with nitrous acid (HONO), thereby converting the primer to an extendable primer having a 3' hydroxyl moiety. R2 can independently be alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, R2 is —C(R6)(R7)(R8), —C(O)(R6), —P(O)(R6)(R7), —C(R6)(=C(R7)(R8)), —Si(R6)(R7)(R8), —$SO_2$(R6), substituted or unsubstituted cycloalkyl (e.g., $C_3$-$C_8$, $C_3$-$C_6$, or $C_5$-$C_6$), substituted or unsubstituted cycloalkenyl (e.g., $C_3$-$C_8$, $C_3$-$C_6$, or $C_5$-$C_6$), substituted or unsubstituted cycloalkynyl (e.g., $C_3$-$C_8$, $C_3$-$C_6$, or $C_5$-$C_6$), substituted or unsubstituted heteroalicyclyl (e.g., 3 to 8 membered, 3 to 6 membered, or 5 to 6 membered), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R2 is —C(R6)(R7)(R8). In embodiments, R2 is —C(O)(R6). In embodiments, R2 is —P(O)(R6)(R7). In embodiments, R2 is —C(R6)(=C(R7)(R8)). In embodiments, R2 is —Si(R6)(R7)(R8). In embodiments, R2 is —$SO_2$(R6). In embodiments, R2 is substituted or unsubstituted cycloalkyl (e.g., $C_3$-$C_8$, $C_3$-$C_6$, or $C_5$-$C_6$). In embodiments, R2 is substituted or unsubstituted cycloalkenyl (e.g., $C_3$-$C_8$, $C_3$-$C_6$, or $C_5$-$C_6$). In embodiments, R2 is substituted or unsubstituted cycloalkynyl (e.g., $C_3$-$C_8$, $C_3$-$C_6$, or $C_5$-$C_6$). In embodiments, R2 is substituted or unsubstituted heteroalicyclyl (e.g., 3 to 8 membered, 3 to 6 membered, or 5 to 6 membered). In embodiments, R2 is substituted or unsubstituted aryl (e.g., $C_6$-$C_{10}$ aryl, $C_{10}$ aryl, or phenyl). In embodiments, R2 is substituted or unsubstituted heteroaryl (e.g., 5 to 10 membered heteroaryl, 5 to 9 membered heteroaryl, or 5 to 6 membered heteroaryl). In embodiments, R2 is unsubstituted cycloalkyl (e.g., $C_3$-$C_8$, $C_3$-$C_6$, or $C_5$-$C_6$). In embodiments, R2 is unsubstituted cycloalkenyl (e.g., $C_3$-$C_8$, $C_3$-$C_6$, or $C_5$-$C_6$). In embodiments, R2 is unsubstituted cycloalkynyl (e.g., $C_3$-$C_8$, $C_3$-$C_6$, or $C_5$-$C_6$). In embodiments, R2 is unsubstituted heteroalicyclyl (e.g., 3 to 8 membered, 3 to 6 membered, or 5 to 6 membered). In embodiments, R2 is unsubstituted aryl (e.g., $C_6$-$C_{10}$ aryl, $C_{10}$ aryl, or phenyl). In embodiments, R2 is unsubstituted heteroaryl (e.g., 5 to 10 membered heteroaryl, 5 to 9 membered heteroaryl, or 5 to 6 membered heteroaryl). In embodiments, R2 is not unsubstituted methyl. In embodiments, R2 is not unsubstituted ethyl. In embodiments, R2 is not unsubstituted propyl.

R6, R7, and R8 are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OC_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$SF_5$, —$N_3$, substituted or unsubstituted alkyl (e.g., $C_1$-$C_8$ alkyl, $C_1$-$C_6$ alkyl, or $C_1$-$C_4$ alkyl), substituted or unsubstituted alkenyl (e.g., $C_2$-$C_8$ alkenyl, $C_2$-$C_6$ alkenyl, or $C_2$-$C_4$ alkenyl), substituted or unsubstituted alkynyl (e.g., $C_2$-$C_8$ alkynyl, $C_2$-$C_6$ alkynyl, or $C_2$-$C_4$ alkynyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$, $C_3$-$C_6$, or $C_5$-$C_6$), substituted or unsubstituted cycloalkenyl (e.g., $C_3$-$C_8$, $C_3$-$C_6$, or $C_5$-$C_6$), substituted or unsubstituted cycloalkynyl (e.g., $C_3$-$C_8$, $C_3$-$C_6$, or $C_5$-$C_6$), substituted or unsubstituted aryl (e.g., $C_6$-$C_{10}$ aryl, $C_{10}$ aryl, or phenyl), substituted or unsubstituted heteroaryl (e.g., 5 to 10 membered heteroaryl, 5 to 9 membered heteroaryl, or 5 to 6 membered heteroaryl), substituted or unsubstituted heteroalicyclyl (e.g., 3 to 8 membered, 3 to 6 membered, or 5 to 6 membered), substituted or unsubstituted aralkyl, substituted or unsubstituted heteroaralkyl, or substituted or unsubstituted (heteroalicyclyl)alkyl. In embodiments, R6, R7, and R8 are not all hydrogen. In embodiments, R2 is —C(R6)(R7)(R8) and R6, R7, and R8 are not all hydrogen.

In embodiments, R6 is independently hydrogen. In embodiments, R6 is independently halogen. In embodiments, R6 is independently —CCl$_3$. In embodiments, R6 is independently —CBr$_3$. In embodiments, R6 is independently —CF$_3$. In embodiments, R6 is independently —CI$_3$. In embodiments, R6 is independently —CHCl$_2$. In embodiments, R6 is independently —CHBr$_2$. In embodiments, R6 is independently —CHF$_2$. In embodiments, R6 is independently —CHI$_2$. In embodiments, R6 is independently —CH$_2$Cl. In embodiments, R6 is independently —CH$_2$Br. In embodiments, R6 is independently —CH$_2$F. In embodiments, R6 is independently —CH$_2$I. In embodiments, R6 is independently —CN. In embodiments, R6 is independently —OH. In embodiments, R6 is independently —NH$_2$. In embodiments, R6 is independently —COOH. In embodiments, R6 is independently —CONH$_2$. In embodiments, R6 is independently —NO$_2$. In embodiments, R6 is independently —SH. In embodiments, R6 is independently —SO$_3$H. In embodiments, R6 is independently —SO$_4$H. In embodiments, R6 is independently —SO$_2$NH$_2$. In embodiments, R6 is independently —NHNH$_2$. In embodiments, R6 is independently —ONH$_2$. In embodiments, R6 is independently —NHC(O)NHNH$_2$. In embodiments, R6 is independently —NHC(O)NH$_2$. In embodiments, R6 is independently —NHSO$_2$H. In embodiments, R6 is independently —NHC(O)H. In embodiments, R6 is independently —NHC(O)OH. In embodiments, R6 is independently —NHOH. In embodiments, R6 is independently —OCCl$_3$. In embodiments, R6 is independently —OCF$_3$. In embodiments, R6 is independently —OCBr$_3$. In embodiments, R6 is independently —OCI$_3$. In embodiments, R6 is independently —OCHCl$_2$. In embodiments, R6 is independently —OCHBr$_2$. In embodiments, R6 is independently —OCHI$_2$. In embodiments, R6 is independently —OCHF$_2$. In embodiments, R6 is independently —OCH$_2$Cl. In embodiments, R6 is independently —OCH$_2$Br. In embodiments, R6 is independently —OCH$_2$I. In embodiments, R6 is independently —OCH$_2$F. In embodiments, R6 is independently —SF$_5$. In embodiments, R6 is independently —N$_3$. In embodiments, R6 is independently substituted or unsubstituted alkyl (e.g., C$_1$-C$_8$ alkyl, C$_1$-C$_6$ alkyl, or C$_1$-C$_4$ alkyl). In embodiments, R6 is independently substituted or unsubstituted alkenyl (e.g., C$_2$-C$_8$ alkenyl, C$_2$-C$_6$ alkenyl, or C$_2$-C$_4$ alkenyl). In embodiments, R6 is independently substituted or unsubstituted alkynyl (e.g., C$_2$-C$_8$ alkynyl, C$_2$-C$_6$ alkynyl, or C$_2$-C$_4$ alkynyl). In embodiments, R6 is independently substituted or unsubstituted heteroalkyl (e.g., 2 to 8 membered heteroalkyl, 2 to 6 membered heteroalkyl, or 2 to 4 membered heteroalkyl). In embodiments, R6 is independently substituted or unsubstituted cycloalkyl (e.g., C$_3$-C$_8$, C$_3$-C$_6$, or C$_5$-C$_6$). In embodiments, R6 is independently substituted or unsubstituted cycloalkenyl (e.g., C$_3$-C$_8$, C$_3$-C$_6$, or C$_5$-C$_6$). In embodiments, R6 is independently substituted or unsubstituted cycloalkynyl (e.g., C$_3$-C$_8$, C$_3$-C$_6$, or C$_5$-C$_6$). In embodiments, R6 is independently substituted or unsubstituted aryl (e.g., C$_6$-C$_{10}$ aryl, C$_{10}$ aryl, or phenyl). In embodiments, R6 is independently substituted or unsubstituted heteroaryl (e.g., 5 to 10 membered heteroaryl, 5 to 9 membered heteroaryl, or 5 to 6 membered heteroaryl). In embodiments, R6 is independently substituted or unsubstituted heteroalicyclyl (e.g., 3 to 8 membered, 3 to 6 membered, or 5 to 6 membered). In embodiments, R6 is independently substituted or unsubstituted aralkyl. In embodiments, R6 is independently substituted or unsubstituted heteroaralkyl. In embodiments, R6 is independently substituted or unsubstituted (heteroalicyclyl)alkyl.

In embodiments, R6 is independently unsubstituted alkyl (e.g., C$_1$-C$_8$ alkyl, C$_1$-C$_6$ alkyl, or C$_1$-C$_4$ alkyl). In embodiments, R6 is independently unsubstituted alkenyl (e.g., C$_2$-C$_8$ alkenyl, C$_2$-C$_6$ alkenyl, or C$_2$-C$_4$ alkenyl). In embodiments, R6 is independently unsubstituted alkynyl (e.g., C$_2$-C$_8$ alkynyl, C$_2$-C$_6$ alkynyl, or C$_2$-C$_4$ alkynyl). In embodiments, R6 is independently unsubstituted heteroalkyl (e.g., 2 to 8 membered heteroalkyl, 2 to 6 membered heteroalkyl, or 2 to 4 membered heteroalkyl). In embodiments, R6 is independently unsubstituted cycloalkyl (e.g., C$_3$-C$_8$, C$_3$-C$_6$, or C$_5$-C$_6$). In embodiments, R6 is independently unsubstituted cycloalkenyl (e.g., C$_3$-C$_8$, C$_3$-C$_6$, or C$_5$-C$_6$). In embodiments, R6 is independently unsubstituted cycloalkynyl (e.g., C$_3$-C$_8$, C$_3$-C$_6$, or C$_5$-C$_6$). In embodiments, R6 is independently unsubstituted aryl (e.g., C$_6$-C$_{10}$ aryl, C$_{10}$ aryl, or phenyl). In embodiments, R6 is independently unsubstituted heteroaryl (e.g., 5 to 10 membered heteroaryl, 5 to 9 membered heteroaryl, or 5 to 6 membered heteroaryl). In embodiments, R6 is independently unsubstituted heteroalicyclyl (e.g., 3 to 8 membered, 3 to 6 membered, or 5 to 6 membered). In embodiments, R6 is independently unsubstituted aralkyl. In embodiments, R6 is independently unsubstituted heteroaralkyl. In embodiments, R6 is independently unsubstituted (heteroalicyclyl)alkyl.

In embodiments, R7 is independently hydrogen. In embodiments, R7 is independently halogen. In embodiments, R7 is independently —CCl$_3$. In embodiments, R7 is independently —CBr$_3$. In embodiments, R7 is independently —CF$_3$. In embodiments, R7 is independently —CI$_3$. In embodiments, R7 is independently —CHCl$_2$. In embodiments, R7 is independently —CHBr$_2$. In embodiments, R7 is independently —CHF$_2$. In embodiments, R7 is independently —CHI$_2$. In embodiments, R7 is independently —CH$_2$Cl. In embodiments, R7 is independently —CH$_2$Br. In embodiments, R7 is independently —CH$_2$F. In embodiments, R7 is independently —CH$_2$I. In embodiments, R7 is independently —CN. In embodiments, R7 is independently —OH. In embodiments, R7 is independently —NH$_2$. In embodiments, R7 is independently —COOH. In embodiments, R7 is independently —CONH$_2$. In embodiments, R7 is independently —NO$_2$. In embodiments, R7 is independently —SH. In embodiments, R7 is independently —SO$_3$H. In embodiments, R7 is independently —SO$_4$H. In embodiments, R7 is independently —SO$_2$NH$_2$. In embodiments, R7 is independently —NHNH$_2$. In embodiments, R7 is independently —ONH$_2$. In embodiments, R7 is independently —NHC(O)NHNH$_2$. In embodiments, R7 is independently —NHC(O)NH$_2$. In embodiments, R7 is independently —NHSO$_2$H. In embodiments, R7 is independently —NHC(O)H. In embodiments, R7 is independently —NHC(O)OH. In embodiments, R7 is independently —NHOH. In embodiments, R7 is independently —OCCl$_3$. In embodiments, R7 is independently —OCF$_3$. In embodiments, R7 is independently —OCBr$_3$. In embodiments, R7 is independently —OCI$_3$. In embodiments, R7 is independently —OCHCl$_2$. In embodiments, R7 is independently —OCHBr$_2$. In embodiments, R7 is independently —OCHI$_2$. In embodiments, R7 is independently —OCHF$_2$. In embodiments, R7 is independently —OCH$_2$Cl. In embodiments, R7 is independently —OCH$_2$Br. In embodiments, R7 is independently —OCH$_2$I. In embodiments, R7 is independently —OCH$_2$F. In embodiments, R7 is independently —SF$_5$. In embodiments, R7 is independently —N$_3$. In embodiments, R7 is independently substituted or unsubstituted alkyl (e.g., $C_1$-$C_8$ alkyl, $C_1$-$C_6$ alkyl, or $C_1$-$C_4$ alkyl). In embodiments, R7 is independently substituted or unsubstituted alkenyl (e.g., $C_2$-$C_8$ alkenyl, $C_2$-$C_6$ alkenyl, or $C_2$-$C_4$ alkenyl). In embodiments, R7 is independently substituted or unsubstituted alkynyl (e.g., $C_2$-$C_8$ alkynyl, $C_2$-$C_6$ alkynyl, or $C_2$-$C_4$ alkynyl). In embodiments, R7 is independently substituted or unsubstituted heteroalkyl (e.g., 2 to 8 membered heteroalkyl, 2 to 6 membered heteroalkyl, or 2 to 4 membered heteroalkyl). In embodiments, R7 is independently substituted or unsubstituted cycloalkyl (e.g., $C_3$-$C_8$, $C_3$-$C_6$, or $C_5$-$C_6$). In embodiments, R7 is independently substituted or unsubstituted cycloalkenyl (e.g., $C_3$-$C_8$, $C_3$-$C_6$, or $C_5$-$C_6$). In embodiments, R7 is independently substituted or unsubstituted cycloalkynyl (e.g., $C_3$-$C_8$, $C_3$-$C_6$, or $C_5$-$C_6$). In embodiments, R7 is independently substituted or unsubstituted aryl (e.g., $C_6$-$C_{10}$ aryl, $C_{10}$ aryl, or phenyl). In embodiments, R7 is independently substituted or unsubstituted heteroaryl (e.g., 5 to 10 membered heteroaryl, 5 to 9 membered heteroaryl, or 5 to 6 membered heteroaryl). In embodiments, R7 is independently substituted or unsubstituted heteroalicyclyl (e.g., 3 to 8 membered, 3 to 6 membered, or 5 to 6 membered). In embodiments, R7 is independently substituted or unsubstituted aralkyl. In embodiments, R7 is independently substituted or unsubstituted heteroaralkyl. In embodiments, R7 is independently substituted or unsubstituted (heteroalicyclyl)alkyl.

In embodiments, R7 is independently unsubstituted alkyl (e.g., $C_1$-$C_8$ alkyl, $C_1$-$C_6$ alkyl, or $C_1$-$C_4$ alkyl). In embodiments, R7 is independently unsubstituted alkenyl (e.g., $C_2$-$C_8$ alkenyl, $C_2$-$C_6$ alkenyl, or $C_2$-$C_4$ alkenyl). In embodiments, R7 is independently unsubstituted alkynyl (e.g., $C_2$-$C_8$ alkynyl, $C_2$-$C_6$ alkynyl, or $C_2$-$C_4$ alkynyl). In embodiments, R7 is independently unsubstituted heteroalkyl (e.g., 2 to 8 membered heteroalkyl, 2 to 6 membered heteroalkyl, or 2 to 4 membered heteroalkyl). In embodiments, R7 is independently unsubstituted cycloalkyl (e.g., $C_3$-$C_8$, $C_3$-$C_6$, or $C_5$-$C_6$). In embodiments, R7 is independently unsubstituted cycloalkenyl (e.g., $C_3$-$C_8$, $C_3$-$C_6$, or $C_5$-$C_6$). In embodiments, R7 is independently unsubstituted cycloalkynyl (e.g., $C_3$-$C_8$, $C_3$-$C_6$, or $C_5$-$C_6$). In embodiments, R7 is independently unsubstituted aryl (e.g., $C_6$-$C_{10}$ aryl, $C_{10}$ aryl, or phenyl). In embodiments, R7 is independently unsubstituted heteroaryl (e.g., 5 to 10 membered heteroaryl, 5 to 9 membered heteroaryl, or 5 to 6 membered heteroaryl). In embodiments, R7 is independently unsubstituted heteroalicyclyl (e.g., 3 to 8 membered, 3 to 6 membered, or 5 to 6 membered). In embodiments, R7 is independently unsubstituted aralkyl. In embodiments, R7 is independently unsubstituted heteroaralkyl. In embodiments, R7 is independently unsubstituted (heteroalicyclyl)alkyl.

In embodiments, R8 is independently hydrogen. In embodiments, R8 is independently halogen. In embodiments, R8 is independently —$CCl_3$. In embodiments, R8 is independently —$CBr_3$. In embodiments, R8 is independently —$CF_3$. In embodiments, R8 is independently —$CI_3$. In embodiments, R8 is independently —$CHCl_2$. In embodiments, R8 is independently —$CHBr_2$. In embodiments, R8 is independently —$CHF_2$. In embodiments, R8 is independently —$CHI_2$. In embodiments, R8 is independently —$CH_2Cl$. In embodiments, R8 is independently —$CH_2Br$. In embodiments, R8 is independently —$CH_2F$. In embodiments, R8 is independently —$CH_2I$. In embodiments, R8 is independently —CN. In embodiments, R8 is independently —OH. In embodiments, R8 is independently —$NH_2$. In embodiments, R8 is independently —COOH. In embodiments, R8 is independently —$CONH_2$. In embodiments, R8 is independently —$NO_2$. In embodiments, R8 is independently —SH. In embodiments, R8 is independently —$SO_3H$. In embodiments, R8 is independently —$SO_4H$. In embodiments, R8 is independently —$SO_2NH_2$. In embodiments, R8 is independently —$NHNH_2$. In embodiments, R8 is independently —$ONH_2$. In embodiments, R8 is independently —$NHC(O)NHNH_2$. In embodiments, R8 is independently —$NHC(O)NH_2$. In embodiments, R8 is independently —$NHSO_2H$. In embodiments, R8 is independently —NHC(O)H. In embodiments, R8 is independently —NHC(O)OH. In embodiments, R8 is independently —NHOH. In embodiments, R8 is independently —$OCCl_3$. In embodiments, R8 is independently —$OCF_3$. In embodiments, R8 is independently —$OCBr_3$. In embodiments, R8 is independently —$OCI_3$. In embodiments, R8 is independently —$OCHCl_2$. In embodiments, R8 is independently —$OCHBr_2$. In embodiments, R8 is independently —$OCHI_2$. In embodiments, R8 is independently —$OCHF_2$. In embodiments, R8 is independently —$OCH_2Cl$. In embodiments, R8 is independently —$OCH_2Br$. In embodiments, R8 is independently —$OCH_2I$. In embodiments, R8 is independently —$OCH_2F$. In embodiments, R8 is independently —$SF_5$. In embodiments, R8 is independently —$N_3$. In embodiments, R8 is independently substituted or unsubstituted alkyl (e.g., $C_1$-$C_8$ alkyl, $C_1$-$C_6$ alkyl, or $C_1$-$C_4$ alkyl). In embodiments, R8 is independently substituted or unsubstituted alkenyl (e.g., $C_2$-$C_8$ alkenyl, $C_2$-$C_6$ alkenyl, or $C_2$-$C_4$ alkenyl). In embodiments, R8 is independently substituted or unsubstituted alkynyl (e.g., $C_2$-$C_8$ alkynyl, $C_2$-$C_6$ alkynyl, or $C_2$-$C_4$ alkynyl). In embodiments, R8 is independently substituted or unsubstituted heteroalkyl (e.g., 2 to 8 membered heteroalkyl, 2 to 6 membered heteroalkyl, or 2 to 4 membered heteroalkyl). In embodiments, R8 is independently substituted or unsubstituted cycloalkyl (e.g., $C_3$-$C_8$, $C_3$-$C_6$, or $C_5$-$C_6$). In embodiments, R8 is independently substituted or unsubstituted cycloalkenyl (e.g., $C_3$-$C_8$, $C_3$-$C_6$, or $C_5$-$C_6$). In embodiments, R8 is independently substituted or unsubstituted cycloalkynyl (e.g., $C_3$-$C_8$, $C_3$-$C_6$, or $C_5$-$C_6$). In embodiments, R8 is independently substituted or unsubstituted aryl (e.g., $C_6$-$C_{10}$ aryl, $C_{10}$ aryl, or phenyl). In embodiments, R8 is independently substituted or unsubstituted heteroaryl (e.g., 5 to 10 membered heteroaryl, 5 to 9 membered heteroaryl, or 5 to 6 membered heteroaryl). In embodiments, R8 is independently substituted or unsubstituted heteroalicyclyl (e.g., 3 to 8 membered, 3 to 6 membered, or 5 to 6 membered). In embodiments, R8 is independently substituted or unsubstituted aralkyl. In embodiments, R8 is independently substituted or unsubstituted heteroaralkyl. In embodiments, R8 is independently substituted or unsubstituted (heteroalicyclyl)alkyl.

In embodiments, R8 is independently unsubstituted alkyl (e.g., $C_1$-$C_8$ alkyl, $C_1$-$C_6$ alkyl, or $C_1$-$C_4$ alkyl). In embodiments, R8 is independently unsubstituted alkenyl (e.g., $C_2$-$C_8$ alkenyl, $C_2$-$C_6$ alkenyl, or $C_2$-$C_4$ alkenyl). In embodiments, R8 is independently unsubstituted alkynyl (e.g., $C_2$-$C_8$ alkynyl, $C_2$-$C_6$ alkynyl, or $C_2$-$C_4$ alkynyl). In embodiments, R8 is independently unsubstituted heteroalkyl (e.g., 2 to 8 membered heteroalkyl, 2 to 6 membered heteroalkyl, or 2 to 4 membered heteroalkyl). In embodiments, R8 is independently unsubstituted cycloalkyl (e.g., $C_3$-$C_8$, $C_3$-$C_6$, or $C_5$-$C_6$). In embodiments, R8 is independently unsubstituted cycloalkenyl (e.g., $C_3$-$C_8$, $C_3$-$C_6$, or $C_5$-$C_6$). In embodiments, R8 is independently unsubstituted cycloalkynyl (e.g., $C_3$-$C_8$, $C_3$-$C_6$, or $C_5$-$C_6$). In embodiments, R8 is independently unsubstituted aryl (e.g., $C_6$-$C_{10}$ aryl, $C_{10}$ aryl, or phenyl). In embodiments, R8 is independently unsubstituted heteroaryl (e.g., 5 to 10 membered heteroaryl, 5 to 9 membered heteroaryl, or 5 to 6 membered heteroaryl). In embodiments, R8 is independently unsubstituted heteroalicyclyl (e.g., 3 to 8 membered, 3 to 6 membered, or 5 to 6 membered). In embodiments, R8 is independently unsubstituted aralkyl. In embodiments, R8 is independently unsubstituted heteroaralkyl. In embodiments, R8 is independently unsubstituted (heteroalicyclyl)alkyl.

The deprotecting treatment can be carried out by reacting the 3'-O-oxime reversible terminator moiety with R2-ONH$_2$ to produce 3'-ONH$_2$ reversible terminator moiety and then treating the 3'-ONH$_2$ moiety with HONO to produce a 3' hydroxyl moiety. In some configurations, the protected primer can have the following structure:

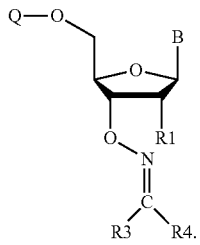

wherein B is a nucleobase; R1 is independently halogen, OCH$_3$, H or OH; and Q is a nucleic acid primer. R3 and R4 can independently be H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. The deblocking treatment can be carried out by reacting the 3'-O-oxime reversible terminator moiety with R2-ONH$_2$ to produce 3'-ONH$_2$ moiety and then treating the 3'-ONH$_2$ moiety with HONO to produce a 3' hydroxyl moiety. In some configurations, the reversibly terminated primer can have the following structure:

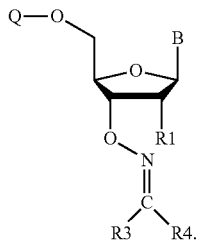

wherein B is a nucleobase; R1 is independently halogen, OCH$_3$, H or OH; and Q is a nucleic acid primer. R3 and R4 can independently be H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, R2 is —C(R6)(R7)(R8), —C(O)(R6), —P(O)(R6)(R7), —C(R6)(=C(R7)(R8)), —Si(R6)(R7)(R8), —SO$_2$(R6), substituted or unsubstituted cycloalkyl (e.g., C$_3$-C$_8$, C$_3$-C$_6$, or C$_5$-C$_6$), substituted or unsubstituted cycloalkenyl (e.g., C$_3$-C$_8$, C$_3$-C$_6$, or C$_5$-C$_6$), substituted or unsubstituted cycloalkynyl (e.g., C$_3$-C$_8$, C$_3$-C$_6$, or C$_5$-C$_6$), substituted or unsubstituted heteroalicyclyl (e.g., 3 to 8 membered, 3 to 6 membered, or 5 to 6 membered), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R2 is —C(R6)(R7)(R8). In embodiments, R2 is —C(O)(R6). In embodiments, R2 is —P(O)(R6)(R7). In embodiments, R2 is —C(R6)(=C(R7)(R8)). In embodiments, R2 is —Si(R6)(R7)(R8). In embodiments, R2 is —SO$_2$(R6). In embodiments, R2 is substituted or unsubstituted cycloalkyl (e.g., C$_3$-C$_8$, C$_3$-C$_6$, or C$_5$-C$_6$). In embodiments, R2 is substituted or unsubstituted cycloalkenyl (e.g., C$_3$-C$_8$, C$_3$-C$_6$, or C$_5$-C$_6$). In embodiments, R2 is substituted or unsubstituted cycloalkynyl (e.g., C$_3$-C$_8$, C$_3$-C$_6$, or C$_5$-C$_6$). In embodiments, R2 is substituted or unsubstituted heteroalicyclyl (e.g., 3 to 8 membered, 3 to 6 membered, or 5 to 6 membered). In embodiments, R2 is substituted or unsubstituted aryl (e.g., C$_6$-C$_{10}$ aryl, C$_{10}$ aryl, or phenyl). In embodiments, R2 is substituted or unsubstituted heteroaryl (e.g., 5 to 10 membered heteroaryl, 5 to 9 membered heteroaryl, or 5 to 6 membered heteroaryl). In embodiments, R2 is unsubstituted cycloalkyl (e.g., C$_3$-C$_8$, C$_3$-C$_6$, or C$_5$-C$_6$). In embodiments, R2 is unsubstituted cycloalkenyl (e.g., C$_3$-C$_8$, C$_3$-C$_6$, or C$_5$-C$_6$). In embodiments, R2 is unsubstituted cycloalkynyl (e.g., C$_3$-C$_8$, C$_3$-C$_6$, or C$_5$-C$_6$). In embodiments, R2 is unsubstituted heteroalicyclyl (e.g., 3 to 8 membered, 3 to 6 membered, or 5 to 6 membered). In embodiments, R2 is unsubstituted aryl (e.g., C$_6$-C$_{10}$ aryl, C$_{10}$ aryl, or phenyl). In embodiments, R2 is unsubstituted heteroaryl (e.g., 5 to 10 membered heteroaryl, 5 to 9 membered heteroaryl, or 5 to 6 membered heteroaryl). In embodiments, R6, R7, and R8 are not all hydrogen. In embodiments, R2 is —C(R6)(R7)(R8) and R6, R7, and R8 are not all hydrogen. In embodiments, R2 is not unsubstituted methyl. In embodiments, R2 is not unsubstituted ethyl. In embodiments, R2 is not unsubstituted propyl.

R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl (e.g., C$_1$-C$_8$ alkyl, C$_1$-C$_6$ alkyl, or C$_1$-C$_4$ alkyl), substituted or unsubstituted alkenyl (e.g., C$_2$-C$_8$ alkenyl, C$_2$-C$_6$ alkenyl, or C$_2$-C$_4$ alkenyl), substituted or unsubstituted alkynyl (e.g., C$_2$-C$_8$ alkynyl, C$_2$-C$_6$ alkynyl, or C$_2$-C$_4$ alkynyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$, C$_3$-C$_6$, or C$_5$-C$_6$), substituted or unsubstituted cycloalkenyl (e.g., C$_3$-C$_8$, C$_3$-C$_6$, or C$_5$-C$_6$), substituted or unsubstituted cycloalkynyl (e.g., C$_3$-C$_8$, C$_3$-C$_6$, or C$_5$-C$_6$), substituted or unsubstituted aryl (e.g., C$_6$-C$_{10}$ aryl, C$_{10}$ aryl, or phenyl), substituted or unsubstituted heteroaryl (e.g., 5 to 10 membered heteroaryl, 5 to 9 membered heteroaryl, or 5 to 6 membered heteroaryl), substituted or unsubstituted heteroalicyclyl (e.g., 3 to 8 membered, 3 to 6 membered, or 5 to 6 membered), substituted or unsubstituted aralkyl, substituted or unsubstituted heteroaralkyl, or substituted or unsubstituted (heteroalicyclyl)alkyl.

In embodiments, R6 is independently hydrogen. In embodiments, R6 is independently halogen. In embodiments, R6 is independently —CCl$_3$. In embodiments, R6 is independently —CBr$_3$. In embodiments, R6 is independently —CF$_3$. In embodiments, R6 is independently —CI$_3$. In embodiments, R6 is independently —CHCl$_2$. In embodiments, R6 is independently —CHBr$_2$. In embodiments, R6 is independently —CHF$_2$. In embodiments, R6 is independently —CHI$_2$. In embodiments, R6 is independently —CH$_2$Cl. In embodiments, R6 is independently —CH$_2$Br. In embodiments, R6 is independently —CH$_2$F. In embodiments, R6 is independently —CH$_2$I. In embodiments, R6 is independently —CN. In embodiments, R6 is independently —OH. In embodiments, R6 is independently —NH$_2$. In embodiments, R6 is independently —COOH. In embodiments, R6 is independently —CONH$_2$. In embodiments, R6 is independently —NO$_2$. In embodiments, R6 is independently —SH. In embodiments, R6 is independently —SO$_3$H. In embodiments, R6 is independently —SO$_4$H. In embodiments, R6 is independently —SO$_2$NH$_2$. In embodiments, R6 is independently —NHNH$_2$. In embodiments, R6 is independently —ONH$_2$. In embodiments, R6 is independently —NHC(O)NHNH$_2$. In embodiments, R6 is independently —NHC(O)NH$_2$. In embodiments, R6 is independently —NHSO$_2$H. In embodiments, R6 is independently —NHC(O)H. In embodiments, R6 is independently —NHC(O)OH. In embodiments, R6 is independently —NHOH. In embodiments, R6 is independently —OCCl$_3$. In embodiments, R6 is independently —OCF$_3$. In embodiments, R6 is independently —OCBr$_3$. In embodiments, R6 is independently —OC$_3$. In embodiments, R6 is independently —OCHCl$_2$. In embodiments, R6 is independently —OCHBr$_2$. In embodiments, R6 is independently —OCHI$_2$. In embodiments, R6 is independently —OCHF$_2$. In embodiments, R6 is independently —OCH$_2$Cl. In embodiments, R6 is independently —OCH$_2$Br. In embodiments, R6 is independently —OCH$_2$I. In embodiments, R6 is independently —OCH$_2$F. In embodiments, R6 is independently —SF$_5$. In embodiments, R6 is independently —N$_3$. In embodiments, R6 is independently substituted or unsubstituted alkyl (e.g., C$_1$-C$_8$ alkyl, C$_1$-C$_6$ alkyl, or C$_1$-C$_4$ alkyl). In embodiments, R6 is independently substituted or unsubstituted alkenyl (e.g., C$_2$-C$_8$ alkenyl, C$_2$-C$_6$ alkenyl, or C$_2$-C$_4$ alkenyl). In embodiments, R6 is independently substituted or unsubstituted alkynyl (e.g., C$_2$-C$_8$ alkynyl, C$_2$-C$_6$ alkynyl, or C$_2$-C$_4$ alkynyl). In embodiments, R6 is independently substituted or unsubstituted heteroalkyl (e.g., 2 to 8 membered heteroalkyl, 2 to 6 membered heteroalkyl, or 2 to 4 membered heteroalkyl). In embodiments, R6 is independently substituted or unsubstituted cycloalkyl (e.g., C$_3$-C$_8$, C$_3$-C$_6$, or C$_5$-C$_6$). In embodiments, R6 is independently substituted or unsubstituted cycloalkenyl (e.g., C$_3$-C$_8$, C$_3$-C$_6$, or C$_5$-C$_6$). In embodiments, R6 is independently substituted or unsubstituted cycloalkynyl (e.g., C$_3$-C$_8$, C$_3$-C$_6$, or C$_5$-C$_6$). In embodiments, R6 is independently substituted or unsubstituted aryl (e.g., C$_6$-C$_{10}$ aryl, C$_{10}$ aryl, or phenyl). In embodiments, R6 is independently substituted or unsubstituted heteroaryl (e.g., 5 to 10 membered heteroaryl, 5 to 9 membered heteroaryl, or 5 to 6 membered heteroaryl). In embodiments, R6 is independently substituted or unsubstituted heteroalicyclyl (e.g., 3 to 8 membered, 3 to 6 membered, or 5 to 6 membered). In embodiments, R6 is independently substituted or unsubstituted aralkyl. In embodiments, R6 is independently substituted or unsubstituted heteroaralkyl. In embodiments, R6 is independently substituted or unsubstituted (heteroalicyclyl)alkyl.

In embodiments, R6 is independently unsubstituted alkyl (e.g., C$_1$-C$_8$ alkyl, C$_1$-C$_6$ alkyl, or C$_1$-C$_4$ alkyl). In embodiments, R6 is independently unsubstituted alkenyl (e.g., C$_2$-C$_8$ alkenyl, C$_2$-C$_6$ alkenyl, or C$_2$-C$_4$ alkenyl). In embodiments, R6 is independently unsubstituted alkynyl (e.g., C$_2$-C$_8$ alkynyl, C$_2$-C$_6$ alkynyl, or C$_2$-C$_4$ alkynyl). In embodiments, R6 is independently unsubstituted heteroalkyl (e.g., 2 to 8 membered heteroalkyl, 2 to 6 membered heteroalkyl, or 2 to 4 membered heteroalkyl). In embodiments, R6 is independently unsubstituted cycloalkyl (e.g., C$_3$-C$_8$, C$_3$-C$_6$, or C$_5$-C$_6$). In embodiments, R6 is independently unsubstituted cycloalkenyl (e.g., C$_3$-C$_8$, C$_3$-C$_6$, or C$_5$-C$_6$). In embodiments, R6 is independently unsubstituted cycloalkynyl (e.g., C$_3$-C$_8$, C$_3$-C$_6$, or C$_5$-C$_6$). In embodiments, R6 is independently unsubstituted aryl (e.g., C$_6$-C$_{10}$ aryl, C$_{10}$ aryl, or phenyl). In embodiments, R6 is independently unsubstituted heteroaryl (e.g., 5 to 10 membered heteroaryl, 5 to 9 membered heteroaryl, or 5 to 6 membered heteroaryl). In embodiments, R6 is independently unsubstituted heteroalicyclyl (e.g., 3 to 8 membered, 3 to 6 membered, or 5 to 6 membered). In embodiments, R6 is independently unsubstituted aralkyl. In embodiments, R6 is independently unsubstituted heteroaralkyl. In embodiments, R6 is independently unsubstituted (heteroalicyclyl)alkyl.

In embodiments, R7 is independently hydrogen. In embodiments, R7 is independently halogen. In embodiments, R7 is independently —CCl$_3$. In embodiments, R7 is independently —CBr$_3$. In embodiments, R7 is independently —CF$_3$. In embodiments, R7 is independently —CI$_3$. In embodiments, R7 is independently —CHCl$_2$. In embodiments, R7 is independently —CHBr$_2$. In embodiments, R7 is independently —CHF$_2$. In embodiments, R7 is independently —CHI$_2$. In embodiments, R7 is independently —CH$_2$Cl. In embodiments, R7 is independently —CH$_2$Br. In embodiments, R7 is independently —CH$_2$F. In embodiments, R7 is independently —CH$_2$I. In embodiments, R7 is independently —CN. In embodiments, R7 is independently —OH. In embodiments, R7 is independently —NH$_2$. In embodiments, R7 is independently —COOH. In embodiments, R7 is independently —CONH$_2$. In embodiments, R7 is independently —NO$_2$. In embodiments, R7 is independently —SH. In embodiments, R7 is independently —SO$_3$H. In embodiments, R7 is independently —SO$_4$H. In embodiments, R7 is independently —SO$_2$NH$_2$. In embodiments, R7 is independently —NHNH$_2$. In embodiments, R7 is independently —ONH$_2$. In embodiments, R7 is independently —NHC(O)NHNH$_2$. In embodiments, R7 is independently —NHC(O)NH$_2$. In embodiments, R7 is independently —NHSO$_2$H. In embodiments, R7 is independently —NHC(O)H. In embodiments, R7 is independently —NHC(O)OH. In embodiments, R7 is independently —NHOH. In embodiments, R7 is independently —OCCl$_3$. In embodiments, R7 is independently —OCF$_3$. In embodiments, R7 is independently —OCBr$_3$. In embodiments, R7 is independently —OCI$_3$. In embodiments, R7 is independently —OCHCl$_2$. In embodiments, R7 is independently —OCHBr$_2$. In embodiments, R7 is independently —OCHI$_2$. In embodiments, R7 is independently —OCHF$_2$. In embodiments, R7 is independently —OCH$_2$Cl. In embodiments, R7 is independently —OCH$_2$Br. In embodiments, R7 is independently —OCH$_2$I. In embodiments, R7 is independently —OCH$_2$F. In embodiments, R7 is independently —SF$_5$. In embodiments, R7 is independently —N$_3$. In embodiments, R7 is independently substituted or unsubstituted alkyl (e.g., C$_1$-C$_8$ alkyl, C$_1$-C$_6$ alkyl, or C$_1$-C$_4$ alkyl). In embodiments, R7 is independently substituted or unsubstituted alkenyl (e.g., C$_2$-C$_8$ alkenyl, C$_2$-C$_6$ alkenyl, or C$_2$-C$_4$ alkenyl). In embodiments, R7 is independently substituted or unsubstituted alkynyl (e.g., C$_2$-C$_8$ alkynyl, C$_2$-C$_6$ alkynyl, or C$_2$-C$_4$ alkynyl). In embodiments, R7 is independently substituted or unsubstituted heteroalkyl (e.g., 2 to 8 membered heteroalkyl, 2 to 6 membered heteroalkyl, or 2 to 4 membered heteroalkyl). In embodiments, R7 is independently substituted or unsubstituted cycloalkyl (e.g., C$_3$-C$_8$, C$_3$-C$_6$, or C$_5$-C$_6$). In embodiments, R7 is independently substituted or unsubstituted cycloalkenyl (e.g., C$_3$-C$_8$, C$_3$-C$_6$, or C$_5$-C$_6$). In embodiments, R7 is independently substituted or unsubstituted cycloalkynyl (e.g., $C_3$-$C_8$, $C_3$-$C_6$, or $C_5$-$C_6$). In embodiments, R7 is independently substituted or unsubstituted aryl (e.g., $C_6$-$C_{10}$ aryl, $C_{10}$ aryl, or phenyl). In embodiments, R7 is independently substituted or unsubstituted heteroaryl (e.g., 5 to 10 membered heteroaryl, 5 to 9 membered heteroaryl, or 5 to 6 membered heteroaryl). In embodiments, R7 is independently substituted or unsubstituted heteroalicyclyl (e.g., 3 to 8 membered, 3 to 6 membered, or 5 to 6 membered). In embodiments, R7 is independently substituted or unsubstituted aralkyl. In embodiments, R7 is independently substituted or unsubstituted heteroaralkyl. In embodiments, R7 is independently substituted or unsubstituted (heteroalicyclyl)alkyl.

In embodiments, R7 is independently unsubstituted alkyl (e.g., $C_1$-$C_8$ alkyl, $C_1$-$C_6$ alkyl, or $C_1$-$C_4$ alkyl). In embodiments, R7 is independently unsubstituted alkenyl (e.g., $C_2$-$C_8$ alkenyl, $C_2$-$C_6$ alkenyl, or $C_2$-$C_4$ alkenyl). In embodiments, R7 is independently unsubstituted alkynyl (e.g., $C_2$-$C_8$ alkynyl, $C_2$-$C_6$ alkynyl, or $C_2$-$C_4$ alkynyl). In embodiments, R7 is independently unsubstituted heteroalkyl (e.g., 2 to 8 membered heteroalkyl, 2 to 6 membered heteroalkyl, or 2 to 4 membered heteroalkyl). In embodiments, R7 is independently unsubstituted cycloalkyl (e.g., $C_3$-$C_8$, $C_3$-$C_6$, or $C_5$-$C_6$). In embodiments, R7 is independently unsubstituted cycloalkenyl (e.g., $C_3$-$C_8$, $C_3$-$C_6$, or $C_5$-$C_6$). In embodiments, R7 is independently unsubstituted cycloalkynyl (e.g., $C_3$-$C_8$, $C_3$-$C_6$, or $C_5$-$C_6$). In embodiments, R7 is independently unsubstituted aryl (e.g., $C_6$-$C_{10}$ aryl, $C_{10}$ aryl, or phenyl). In embodiments, R7 is independently unsubstituted heteroaryl (e.g., 5 to 10 membered heteroaryl, 5 to 9 membered heteroaryl, or 5 to 6 membered heteroaryl). In embodiments, R7 is independently unsubstituted heteroalicyclyl (e.g., 3 to 8 membered, 3 to 6 membered, or 5 to 6 membered). In embodiments, R7 is independently unsubstituted aralkyl. In embodiments, R7 is independently unsubstituted heteroaralkyl. In embodiments, R7 is independently unsubstituted (heteroalicyclyl)alkyl.

In embodiments, R8 is independently hydrogen. In embodiments, R8 is independently halogen. In embodiments, R8 is independently —$CCl_3$. In embodiments, R8 is independently —$CBr_3$. In embodiments, R8 is independently —$CF_3$. In embodiments, R8 is independently —$CI_3$. In embodiments, R8 is independently —$CHCl_2$. In embodiments, R8 is independently —$CHBr_2$. In embodiments, R8 is independently —$CHF_2$. In embodiments, R8 is independently —$CHI_2$. In embodiments, R8 is independently —$CH_2Cl$. In embodiments, R8 is independently —$CH_2Br$. In embodiments, R8 is independently —$CH_2F$. In embodiments, R8 is independently —$CH_2I$. In embodiments, R8 is independently —CN. In embodiments, R8 is independently —OH. In embodiments, R8 is independently —$NH_2$. In embodiments, R8 is independently —COOH. In embodiments, R8 is independently —$CONH_2$. In embodiments, R8 is independently —$NO_2$. In embodiments, R8 is independently —SH. In embodiments, R8 is independently —$SO_3H$. In embodiments, R8 is independently —$SO_4H$. In embodiments, R8 is independently —$SO_2NH_2$. In embodiments, R8 is independently —$NHNH_2$. In embodiments, R8 is independently —$ONH_2$. In embodiments, R8 is independently —NHC(O)$NHNH_2$. In embodiments, R8 is independently —NHC(O)$NH_2$. In embodiments, R8 is independently —$NHSO_2H$. In embodiments, R8 is independently —NHC(O)H. In embodiments, R8 is independently —NHC(O)OH. In embodiments, R8 is independently —NHOH. In embodiments, R8 is independently —$OCCl_3$. In embodiments, R8 is independently —$OCF_3$. In embodiments, R8 is independently —$OCBr_3$. In embodiments, R8 is independently —$OCI_3$. In embodiments, R8 is independently —$OCHCl_2$. In embodiments, R8 is independently —$OCHBr_2$. In embodiments, R8 is independently —$OCHI_2$. In embodiments, R8 is independently —$OCHF_2$. In embodiments, R8 is independently —$OCH_2Cl$. In embodiments, R8 is independently —$OCH_2Br$. In embodiments, R8 is independently —$OCH_2I$. In embodiments, R8 is independently —$OCH_2F$. In embodiments, R8 is independently —$SF_5$. In embodiments, R8 is independently —$N_3$. In embodiments, R8 is independently substituted or unsubstituted alkyl (e.g., $C_1$-$C_8$ alkyl, $C_1$-$C_6$ alkyl, or $C_1$-$C_4$ alkyl). In embodiments, R8 is independently substituted or unsubstituted alkenyl (e.g., $C_2$-$C_8$ alkenyl, $C_2$-$C_6$ alkenyl, or $C_2$-$C_4$ alkenyl). In embodiments, R8 is independently substituted or unsubstituted alkynyl (e.g., $C_2$-$C_8$ alkynyl, $C_2$-$C_6$ alkynyl, or $C_2$-$C_4$ alkynyl). In embodiments, R8 is independently substituted or unsubstituted heteroalkyl (e.g., 2 to 8 membered heteroalkyl, 2 to 6 membered heteroalkyl, or 2 to 4 membered heteroalkyl). In embodiments, R8 is independently substituted or unsubstituted cycloalkyl (e.g., $C_3$-$C_8$, $C_3$-$C_6$, or $C_5$-$C_6$). In embodiments, R8 is independently substituted or unsubstituted cycloalkenyl (e.g., $C_3$-$C_8$, $C_3$-$C_6$, or $C_5$-$C_6$). In embodiments, R8 is independently substituted or unsubstituted cycloalkynyl (e.g., $C_3$-$C_8$, $C_3$-$C_6$, or $C_5$-$C_6$). In embodiments, R8 is independently substituted or unsubstituted aryl (e.g., $C_6$-$C_{10}$ aryl, $C_{10}$ aryl, or phenyl). In embodiments, R8 is independently substituted or unsubstituted heteroaryl (e.g., 5 to 10 membered heteroaryl, 5 to 9 membered heteroaryl, or 5 to 6 membered heteroaryl). In embodiments, R8 is independently substituted or unsubstituted heteroalicyclyl (e.g., 3 to 8 membered, 3 to 6 membered, or 5 to 6 membered). In embodiments, R8 is independently substituted or unsubstituted aralkyl. In embodiments, R8 is independently substituted or unsubstituted heteroaralkyl. In embodiments, R8 is independently substituted or unsubstituted (heteroalicyclyl)alkyl.

In embodiments, R8 is independently unsubstituted alkyl (e.g., $C_1$-$C_8$ alkyl, $C_1$-$C_6$ alkyl, or $C_1$-$C_4$ alkyl). In embodiments, R8 is independently unsubstituted alkenyl (e.g., $C_2$-$C_8$ alkenyl, $C_2$-$C_6$ alkenyl, or $C_2$-$C_4$ alkenyl). In embodiments, R8 is independently unsubstituted alkynyl (e.g., $C_2$-$C_8$ alkynyl, $C_2$-$C_6$ alkynyl, or $C_2$-$C_4$ alkynyl). In embodiments, R8 is independently unsubstituted heteroalkyl (e.g., 2 to 8 membered heteroalkyl, 2 to 6 membered heteroalkyl, or 2 to 4 membered heteroalkyl). In embodiments, R8 is independently unsubstituted cycloalkyl (e.g., $C_3$-$C_8$, $C_3$-$C_6$, or $C_5$-$C_6$). In embodiments, R8 is independently unsubstituted cycloalkenyl (e.g., $C_3$-$C_8$, $C_3$-$C_6$, or $C_5$-$C_6$). In embodiments, R8 is independently unsubstituted cycloalkynyl (e.g., $C_3$-$C_8$, $C_3$-$C_6$, or $C_5$-$C_6$). In embodiments, R8 is independently unsubstituted aryl (e.g., $C_6$-$C_{10}$ aryl, $C_{10}$ aryl, or phenyl). In embodiments, R8 is independently unsubstituted heteroaryl (e.g., 5 to 10 membered heteroaryl, 5 to 9 membered heteroaryl, or 5 to 6 membered heteroaryl). In embodiments, R8 is independently unsubstituted heteroalicyclyl (e.g., 3 to 8 membered, 3 to 6 membered, or 5 to 6 membered). In embodiments, R8 is independently unsubstituted aralkyl. In embodiments, R8 is independently unsubstituted heteroaralkyl. In embodiments, R8 is independently unsubstituted (heteroalicyclyl)alkyl.

Sequencing is commonly carried out using a DNA template and DNA primer. Accordingly, the primer used in a sequencing process can have the following structure:

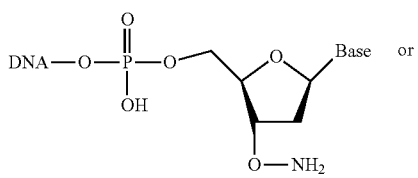

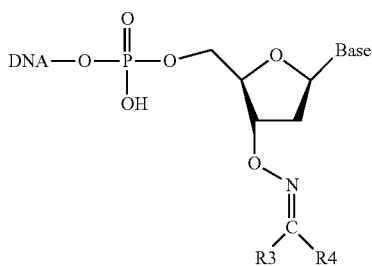

wherein Base is a nucleobase, and wherein DNA is the deoxyribonucleic acid primer. It will be understood that RNA can be used in place of DNA for a sequencing process. R3 and R4 can independently be H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

A sequencing method of the present disclosure can include an extension step, whereby a nucleotide is added to the 3' end of a deblocked primer. The nucleotide is typically added via polymerase catalysis. The nucleotide can include a reversible terminator moiety so that only a single nucleotide is added to the primer in the extension step. Similarly, a sequencing method can include an extension step, whereby an oligonucleotide is added to the 3' end of the deblocked primer. The oligonucleotide is typically added via ligase catalysis. The nucleotide at the 3' end of the oligonucleotide can include a reversible terminator moiety so that only a single oligonucleotide is added to the primer in the extension step. A reversibly terminated nucleotide or oligonucleotide can include an exogenous label or, alternatively, the reversibly terminated nucleotide or oligonucleotide can lack exogenous labels. By way of example, the reversibly terminated nucleotide that is used for primer extension can have the structure:

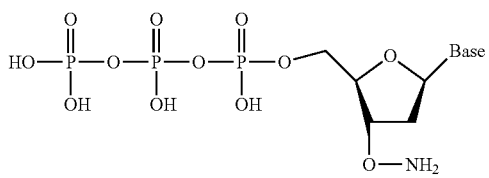

and can be produced through deblocking of a nucleotide such as

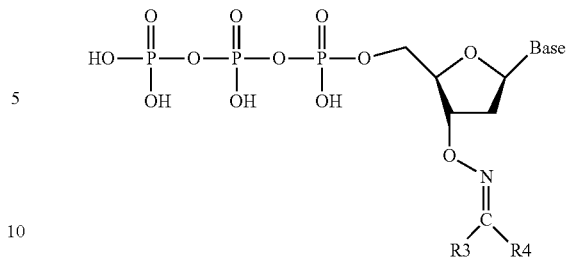

wherein Base is the nucleobase. R3 and R4 can independently be H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In some sequencing processes, a nucleotide or oligonucleotide that is added to a primer in an extension step can have an exogenous label moiety such that the exogenous label is attached to the extended primer. Labelling an extended primer can be useful for a sequencing by synthesis method or sequencing by ligation method such as those set forth in further detail in the description and cited references below. In alternative sequencing processes the nucleotide or oligonucleotide that is added in an extension step will lack exogenous label moieties such that the extended primer will not have an exogenous label. Non-labelled extended primers can be useful for a Sequencing By Synthesis™ method such as those set forth in further detail in the description and cited references below.

The use of reversibly terminated nucleotides and deblocking methods set forth herein can beneficially facilitate cyclical techniques that employ repeated cycles of reagent delivery and product detection. Each cycle can include one step or multiple steps. For example, each cycle can include all steps needed to detect signals that are indicative of a single nucleotide position in a template nucleic acid. Such sequencing processes can be referred to as cyclical reversible terminator (CRT) techniques. Each cycle in a CRT technique can include steps for (i) adding a single reversibly terminated nucleotide (or single reversibly terminated oligonucleotide) to increment a nascent primer to a nucleotide position that is to be detected; (ii) detecting a nucleotide at the single nucleotide position or at an adjacent position, and (iii) deblocking the nascent primer to allow a return to step (i) to start a subsequent cycle.

A specific example of a useful CRT nucleic acid sequencing process is a Sequencing By Binding™ (SBB™) reaction, for example, as described in commonly owned US Pat. App. Pub. Nos. 2017/0022553 A1; 2018/0044727 A1; 2018/0187245 A1; or 2018/0208983 A1, each of which is incorporated herein by reference. SBB™ methods for determining the sequence of a template nucleic acid molecule can optionally be based on formation of a ternary complex (between polymerase, primed nucleic acid and next correct nucleotide) under specified conditions. The method can include an examination phase followed by a nucleotide incorporation phase (also referred to as an extension phase).

The examination phase of an SBB™ process can be carried out for at least one template nucleic acid molecule that is hybridized to a primer. The primer can be reversibly terminated. The primed template can be contacted with a reaction mixture that includes a polymerase and at least one nucleotide type. Interaction of polymerase and a nucleotide with the primed template nucleic acid molecule(s) can be observed under conditions where the nucleotide is not covalently added to the primer(s); and the next base in each template nucleic acid can be identified using the observed interaction of the polymerase and nucleotide with the primed template nucleic acid molecule(s). The interaction between the primed template, polymerase and nucleotide can be detected in a variety of schemes. For example, the nucleotide can contain a detectable label. Nucleotides with different nucleobase types can be distinguished by different labels, respectively. Each type of nucleobase can have a distinguishable label with respect to other types of nucleobases. Alternatively, some or all of the different nucleobase types can have the same label and the different nucleotide types can be distinguished based on separate deliveries of the respective nucleotide types to the flow cell. In some embodiments, the polymerase can be labeled. Polymerases that are associated with different nucleobase types can have unique labels that distinguish the type of nucleotide to which they are associated. Alternatively, polymerases can have similar labels and the different nucleobase types can be distinguished based on separate deliveries of different nucleotide types to the flow cell.

During the examination phase of an SBB™ process, discrimination between correct and incorrect nucleotides can be facilitated by ternary complex stabilization. A variety of conditions and reagents can be useful. For example, the primer can contain a reversible terminator moiety such as those set forth herein; and/or polymerase cofactors that are required for extension, such as divalent metal ions, can be absent; and/or inhibitory divalent cations that inhibit polymerase-based primer extension can be present; and/or the polymerase that is present in the examination phase can have a chemical modification and/or mutation that inhibits primer extension; and/or the nucleotides can have chemical modifications that inhibit incorporation, such as 5' modifications that remove or alter the native triphosphate moiety. The examination phase can include detection using apparatus and methods set forth herein. Once examination is complete, the SBB™ process can proceed to the next cycle by removing the polymerase and nucleotides used for examination and subjecting the primed template nucleic acid to further cycles of deblocking, extension and examination.

Washes can be carried out between the various delivery steps of an SBB™ process. Wash steps can be performed between any of a variety of steps set forth herein. For example, a wash step can be useful for separating a primed template nucleic acid from other reagents that were contacted with the primed template nucleic acid under ternary complex stabilizing conditions during an SBB™ process. Such a wash can remove one or more reagents from interfering with examination of a mixture or from contaminating a second mixture that is to be formed on a substrate (or in a vessel) that had previously been in contact with the first mixture. For example, a primed template nucleic acid can be contacted with a polymerase and at least one nucleotide type to form a first mixture under ternary complex stabilizing conditions, and the first mixture can be examined. Optionally, a wash can be carried out prior to examination to remove reagents that are not participating in formation of a stabilized ternary complex. Alternatively, or additionally, a wash can be carried out after the examination step to remove one or more component of the first mixture from the primed template nucleic acid. Then the primed template nucleic acid can be contacted with a polymerase and at least one other nucleotide to form a second mixture under ternary complex stabilizing conditions, and the second mixture can be examined for ternary complex formation. As before, an optional wash can be carried out prior to the second examination to remove reagents that are not participating in formation of a stabilized ternary complex.

Another useful CRT sequencing process is sequencing-by-synthesis (SBS). SBS generally involves the enzymatic extension of a nascent primer through the iterative addition of nucleotides against a template strand to which the primer is hybridized. Briefly, SBS can be initiated by contacting target nucleic acids, attached to sites in a flow cell, with one or more labeled nucleotides, DNA polymerase, etc. Those sites where a primer is extended using the target nucleic acid as template will incorporate a labeled nucleotide that can be detected. Optionally, the labeled nucleotides can further include a reversible terminator such as any of those set forth herein. For example, a nucleotide analog having a reversible terminator moiety can be added to a primer such that subsequent extension cannot occur until a deblocking reagent of the present disclosure is delivered to remove the moiety. Thus, for embodiments that use reversible termination, a deblocking reagent can be delivered to the vessel (before or after detection occurs). Washes can be carried out between the various delivery steps. The cycle can be performed n times to extend the primer by n nucleotides, thereby detecting a sequence of length n. Exemplary SBS procedures, reagents and detection components that can be readily modified to employ a reversible terminator and deblocking reagent of the present disclosure are described, for example, in Bentley et al., Nature 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. Also useful are SBS methods that are commercially available from Illumina, Inc. (San Diego, Calif.).

Sequencing-by-ligation reactions are also useful including, for example, those described in Shendure et al. Science 309:1728-1732 (2005); U.S. Pat. No. 5,599,675; or U.S. Pat. No. 5,750,341, each of which is incorporated herein by reference. Some embodiments can include sequencing-by-hybridization procedures as described, for example, in Bains et al., Journal of Theoretical Biology 135 (3), 303-7 (1988); Drmanac et al., Nature Biotechnology 16, 54-58 (1998); Fodor et al., Science 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template. The primers and oligonucleotides used in such processes can include reversible terminators set forth herein and they can be deblocked using reagents set forth herein.

Steps for the above sequencing methods can be carried out cyclically. For example, examination and extension steps of an SBB™ method can be repeated such that in each cycle a single next correct nucleotide is examined (i.e. the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer. Any number of cycles of a sequencing method set forth herein can be carried out including, for example, at least 1, 2, 10, 25, 50, 100, 150, 250, 500 or more cycles. Alternatively or additionally, no more than 500, 250, 150, 100, 50, 25, 10, 2 or 1 cycles are carried out.

Any of a variety of polymerases can be used in a method set forth herein. Reference to a particular polymerase, such as those exemplified throughout this disclosure, will be understood to include functional variants thereof unless indicated otherwise. Particularly useful functions of a polymerase include formation of a ternary complex, extension of a primer to introduce a nucleotide (such as a reversible terminated nucleotide), or catalysis of the polymerization of a nucleic acid strand using an existing nucleic acid as a template.

Polymerases can be classified based on structural homology such as the classification of polymerases into families identified as A, B, C, D, X, Y, and RT. DNA Polymerases in Family A include, for example, T7 DNA polymerase, eukaryotic mitochondrial DNA Polymerase 7, *E. coli* DNA Pol I, *Thermus aquaticus* Pol I, and *Bacillus stearothermophilus* Pol I. DNA Polymerases in Family B include, for example, eukaryotic DNA polymerases α, δ, and ε; DNA polymerase ζ; T4 DNA polymerase; Phi29 DNA polymerase; and RB69 bacteriophage DNA polymerase. Family C includes, for example, the *E. coli* DNA Polymerase III alpha subunit. Family B archaeon DNA polymerases include, for example, Vent, Deep Vent, Pfu and 9° N. (e.g., Therminator™ DNA polymerase from New England BioLabs Inc.; Ipswich, Mass.) polymerases. Family D includes, for example, polymerases derived from the Euryarchaeota subdomain of Archaea. DNA Polymerases in Family X include, for example, eukaryotic polymerases Pol β, pol α, Pol λ, and Pol μ, and *S. cerevisiae* Pol4. DNA Polymerases in Family Y include, for example, Pol f, Pol t, Pol K, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

Further examples of useful DNA polymerases include bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cp7 DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator™ DNA polymerase from New England BioLabs Inc.; Ipswich, Mass.) can be used.

Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some applications of the methods and systems set forth herein. For example, the 3'-5' exonuclease activity can be used to remove a reversibly terminated nucleotide from the 3' end of a primer. Polymerases that substantially lack 3'-5' proofreading exonuclease activity are also useful in some configurations, for example, in most sequencing systems and methods. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

Polymerases that may be used in a method or composition set forth herein include naturally occurring polymerases and modified variations thereof, including, but not limited to, mutants, recombinants, fusions, genetic modifications, chemical modifications, synthetics, and analogs. Useful polymerases for ternary complex formation and detection are not limited to polymerases that have the ability to catalyze a polymerization reaction. Optionally, a useful polymerase will have the ability to catalyze a polymerization reaction in at least one condition that is not used during formation or examination of a stabilized ternary complex. Exemplary polymerases that can be used to form a stabilized ternary complex include, for example, wild type and mutant polymerases set forth in US Pat. App. Pub. Nos. 2017/0314072 A1 or 2018/0155698 A1, or U.S. Pat. App. Ser. No. 62/732,510, each of which is incorporated herein by reference.

Polymerases that contain an exogenous label moiety (e.g., an exogenous luminophore), which can be used to detect the polymerase (e.g. during an SBB™ examination step), can be useful in some embodiments. Optionally, the exogenous label moiety can be chemically linked to the polymerase, for example, using a free sulfhydryl or a free amine moiety of the polymerase. An exogenous label moiety can also be attached to a polymerase via protein fusion. Exemplary label moieties that can be attached via protein fusion include, for example, green fluorescent protein (GFP), phycobiliprotein (e.g. phycocyanin and phycoerythrin) or wavelength-shifted variants of GFP or phycobiliprotein.

Also provided is a nucleic acid detection apparatus that includes a fluid reagent delivery system, a detection system, and a flow cell, wherein the fluid reagent delivery system is configured to deliver a fluid reagent to the flow cell, wherein the detection system is configured to detect a signal in the flow cell, wherein the flow cell is attached to a first molecule having the structure:

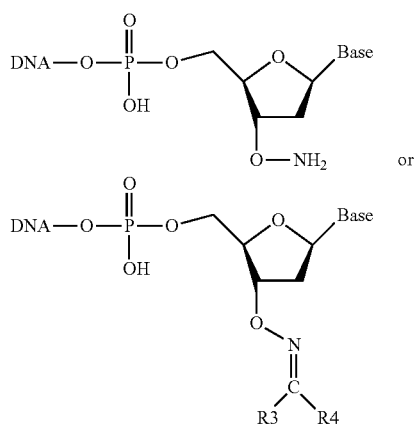

wherein Base is a nucleobase, wherein DNA is independently a single stranded deoxyribonucleic acid or double stranded deoxyribonucleic acid, and wherein the fluid reagent comprises a second molecule comprising the structure: R2-ONH$_2$, wherein R2, R3 and R4 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

An apparatus of the present disclosure can be configured for detection of luminescence or fluorescence. Accordingly, the apparatus can include a detection system having an optical excitation apparatus, such as a laser, LED or lamp, and a luminescence detector such as a camera (e.g. complementary metal oxide semiconductor (CMOS) camera or charge coupled device (CCD) camera). Examples of detection apparatus and components thereof that can be used in a system or method herein are described, for example, in US Pat. App. Pub. No. 2010/0111768 A1 or U.S. Pat. Nos. 7,329,860; 8,951,781 or 9,193,996, each of which is incorporated herein by reference. Other detection apparatus include those commercialized for nucleic acid sequencing such as those provided by Illumina™, Inc. (e.g. HiSeq™, MiSeq™, NextSeq™, or NovaSeq™ systems), Life Technologies™ (e.g. ABI PRISM™, or SOLiD™ systems), Pacific Biosciences (e.g. systems using SMRT™ Technology such as the Sequel™ or RS II™ systems), or Qiagen (e.g. Genereader™ system). Other useful detectors are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference in its entirety.

Although the compositions and methods of the present disclosure are illustrated in the context of optical detection in several exemplary configurations herein, it will be understood that other detection modalities can be used in addition or instead. For example, the detector can be an electronic detector used for detection of protons or pyrophosphate (see, for example, US Pat. App. Pub. Nos. 2009/0026082 A1; 2009/0127589 A1; 2010/0137143 A1; or 2010/0282617 A1, each of which is incorporated herein by reference in its entirety, or the Ion Torrent™ systems commercially available from ThermoFisher, Waltham, Mass.) or as used in detection of nanopores such as those commercialized by Oxford Nanopore™, Oxford UK (e.g. MinION™ or PromethION™ systems) or set forth in U.S. Pat. No. 7,001,792; Soni & Meller, *Clin. Chem.* 53, 1996-2001 (2007); Healy, *Nanomed.* 2, 459-481 (2007); or Cockroft, et al. *J. Am. Chem. Soc.* 130, 818-820 (2008), each of which is incorporated herein by reference. A FET detector can be used such as one or more of those described in U.S. Pat. App. Ser. No. 62/767,712; US Pat. App. Pub. Nos. 2017/0240962 A1, 2018/0051316 A1, 2018/0112265 A1, 2018/0155773 A1 or 2018/0305727 A1; or U.S. Pat. Nos. 9,164,053, 9,829,456, 10,036,064, or 10,125,391, each of which is incorporated herein by reference.

Other detection techniques that can be used in a method set forth herein include, for example, mass spectrometry which can be used to perceive mass; surface plasmon resonance which can be used to perceive binding to a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques.

A useful detection apparatus can include a fluid reagent delivery system. The fluid delivery system can include a reaction vessel (e.g. flow cell) that is configured to carry out chemical reactions set forth herein. The reaction vessel can also be configured to allow detection of the reactions or products of the reactions. The fluid delivery system can include reservoirs for storing reagents. The fluids from the reagents can be delivered to a reaction vessel (e.g. a flow cell) via the fluid delivery system. Spent reagents and products or waste from a reaction can be evacuated from the reaction vessel to a waste reservoir.

In particular configurations, a fluid reagent delivery system is configured to deliver a primer extension reagent to the flow cell, wherein the primer extension reagent comprises a polymerase and a nucleotide having a 3' ONH$_2$ moiety. For example, a nucleotide that is stored or delivered by a fluid reagent delivery system can have the following structure:

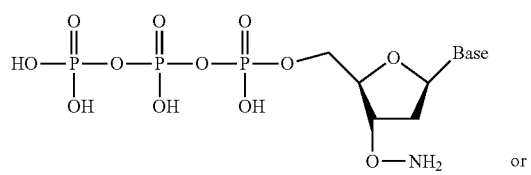 or

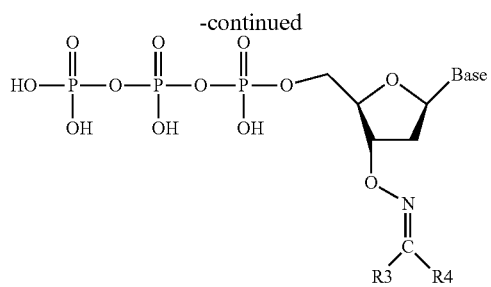

wherein Base is a nucleobase. R3 and R4 can independently be H, $CH_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. Other reagents set forth herein, for example, those that are useful for a CRT sequencing process can be stored or delivered via a fluid reagent delivery system. For example, the fluid reagent delivery system can be configured to deliver a ternary complex formation reagent to a reaction vessel, wherein the ternary complex formation reagent includes a polymerase and a nucleotide that is the next correct nucleotide for a primed template nucleic acid.

A detection apparatus of the present disclosure can include a program module configured to direct the apparatus to perform a nucleic acid sequencing process, wherein the nucleic acid sequencing process comprises repeated deliveries of the fluid reagent to a reaction vessel via a fluid reagent delivery system and repeated detection of the reaction vessel by the detection system. Control of apparatus components can utilize a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The same or different processor that is used to control fluids can interact with the system to acquire, store and process signals (e.g. signals detected in a method set forth herein). In particular embodiments, a processor can be used to determine, from the signals, the identity of the nucleotide that is present at a particular location in a template nucleic acid. In some cases, the processor will identify a sequence of nucleotides for the template from the signals that are detected.

A useful processor can include one or more of a personal computer system, server computer system, thin client, thick client, hand-held or laptop device, multiprocessor system, microprocessor-based system, set top box, programmable consumer electronic, network PC, minicomputer system, mainframe computer system, smart phone, and distributed cloud computing environments that include any of the above systems or devices, and the like. The processor can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The processor may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks set forth herein.

The components of a processor or other programmable device may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A processor can optionally communicate with one or more external devices such as a keyboard, a pointing device (e.g. a mouse), a display, such as a graphical user interface (GUI), or other device that facilitates interaction of a user with a system of the present disclosure. Similarly, the processor can communicate with other devices (e.g., via network card, modem, etc.). Such communication can occur via I/O interfaces. Still yet, a processor of a system herein may communicate with one or more networks such as a local area network (LAN), a general wide area network (WAN), and/or a public network (e.g., the Internet) via a suitable network adapter.

This disclosure further provides kits that can be used, for example, for characterizing nucleic acids. A kit can include reagents for carrying out one or more of the methods set forth herein or using or generating a composition disclosed herein. For example, a kit can include one or more reagents set forth herein for deblocking a reversibly terminated nucleotide or nucleic acid. Alternatively or additionally, a kit of the present disclosure can include one or more reagents for carrying out a primer extension step including, for example, a reversibly terminated nucleotide or reversibly terminated nucleic acid, and/or polymerase. A polymerase that is used for an extension step or for an examination step can also be included in a kit. A kit of the invention can optionally include reagents for carrying out other steps of a sequencing process including, for example, an examination steps used to create and detect a stabilized ternary complex, a wash step, a step for producing nucleic acid clusters or the like.

Accordingly, the present disclosure provides a kit that includes a first vessel containing a nucleotide comprising a 3'-O-oxime moiety and a second vessel containing a reagent comprising the structure $R2-ONH_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, R2 is —C(R6)(R7)(R8), —C(O)(R6), —P(O)(R6)(R7), —C(R6)(=C(R7)(R8)), —Si(R6)(R7)(R8), —SO$_2$(R6), substituted or unsubstituted cycloalkyl (e.g., C$_3$-C$_8$, C$_3$-C$_6$, or C$_5$-C$_6$), substituted or unsubstituted cycloalkenyl (e.g., C$_3$-C$_8$, C$_3$-C$_6$, or C$_5$-C$_6$), substituted or unsubstituted cycloalkynyl (e.g., C$_3$-C$_8$, C$_3$-C$_6$, or C$_5$-C$_6$), substituted or unsubstituted heteroalicyclyl (e.g., 3 to 8 membered, 3 to 6 membered, or 5 to 6 membered), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R2 is —C(R6)(R7)(R8). In embodiments, R2 is —C(O)(R6). In embodiments, R2 is —P(O)(R6)(R7). In embodiments, R2 is —C(R6)(=C(R7)(R8)). In embodiments, R2 is —Si(R6)(R7)(R8). In embodiments, R2 is —SO$_2$(R6). In embodiments, R2 is substituted or unsubstituted cycloalkyl (e.g., C$_3$-C$_8$, C$_3$-C$_6$, or C$_5$-C$_6$). In embodiments, R2 is substituted or unsubstituted cycloalkenyl (e.g., C$_3$-C$_8$, C$_3$-C$_6$, or C$_5$-C$_6$). In embodiments, R2 is substituted or unsubstituted cycloalkynyl (e.g., C$_3$-C$_8$, C$_3$-C$_6$, or C$_5$-C$_6$). In embodiments, R2 is substituted or unsubstituted heteroalicyclyl (e.g., 3 to 8 membered, 3 to 6 membered, or 5 to 6 membered). In embodiments, R2 is substituted or unsubstituted aryl (e.g., C$_6$-C$_{10}$ aryl, C$_{10}$ aryl, or phenyl). In embodiments, R2 is substituted or unsubstituted heteroaryl (e.g., 5 to 10 membered heteroaryl, 5 to 9 membered heteroaryl, or 5 to 6 membered heteroaryl). In embodiments, R2 is unsubstituted cycloalkyl (e.g., C$_3$-C$_8$, C$_3$-C$_6$, or C$_5$-C$_6$). In embodiments, R2 is unsubstituted cycloalkenyl (e.g., C$_3$-C$_8$, C$_3$-C$_6$, or C$_5$-C$_6$). In embodiments, R2 is unsubstituted cycloalkynyl (e.g., C$_3$-C$_8$, C$_3$-C$_6$, or C$_5$-C$_6$). In embodiments, R2 is unsubstituted heteroalicyclyl (e.g., 3 to 8 membered, 3 to 6 membered, or 5 to 6 membered). In embodiments, R2 is unsubstituted aryl (e.g., C$_6$-C$_{10}$ aryl, C$_{10}$ aryl, or phenyl). In embodiments, R2 is unsubstituted heteroaryl (e.g., 5 to 10 membered heteroaryl, 5 to 9 membered heteroaryl, or 5 to 6 membered heteroaryl). In embodiments, R2 is not unsubstituted methyl. In embodiments, R2 is not unsubstituted ethyl. In embodiments, R2 is not unsubstituted propyl.

R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl (e.g., C$_1$-C$_8$ alkyl, C$_1$-C$_6$ alkyl, or C$_1$-C$_4$ alkyl), substituted or unsubstituted alkenyl (e.g., C$_2$-C$_8$ alkenyl, C$_2$-C$_6$ alkenyl, or C$_2$-C$_4$ alkenyl), substituted or unsubstituted alkynyl (e.g., C$_2$-C$_8$ alkynyl, C$_2$-C$_6$ alkynyl, or C$_2$-C$_4$ alkynyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$, C$_3$-C$_6$, or C$_5$-C$_6$), substituted or unsubstituted cycloalkenyl (e.g., C$_3$-C$_8$, C$_3$-C$_6$, or C$_5$-C$_6$), substituted or unsubstituted cycloalkynyl (e.g., C$_3$-C$_8$, C$_3$-C$_6$, or C$_5$-C$_6$), substituted or unsubstituted aryl (e.g., C$_6$-C$_{10}$ aryl, C$_{10}$ aryl, or phenyl), substituted or unsubstituted heteroaryl (e.g., 5 to 10 membered heteroaryl, 5 to 9 membered heteroaryl, or 5 to 6 membered heteroaryl), substituted or unsubstituted heteroalicyclyl (e.g., 3 to 8 membered, 3 to 6 membered, or 5 to 6 membered), substituted or unsubstituted aralkyl, substituted or unsubstituted heteroaralkyl, or substituted or unsubstituted (heteroalicyclyl)alkyl. In embodiments, R6, R7, and R8 are not all hydrogen. In embodiments, R2 is —C(R6)(R7)(R8) and R6, R7, and R8 are not all hydrogen.

In embodiments, R6 is independently hydrogen. In embodiments, R6 is independently halogen. In embodiments, R6 is independently —CCl$_3$. In embodiments, R6 is independently —CBr$_3$. In embodiments, R6 is independently —CF$_3$. In embodiments, R6 is independently —CI$_3$. In embodiments, R6 is independently —CHCl$_2$. In embodiments, R6 is independently —CHBr$_2$. In embodiments, R6 is independently —CHF$_2$. In embodiments, R6 is independently —CHI$_2$. In embodiments, R6 is independently —CH$_2$Cl. In embodiments, R6 is independently —CH$_2$Br. In embodiments, R6 is independently —CH$_2$F. In embodiments, R6 is independently —CH$_2$I. In embodiments, R6 is independently —CN. In embodiments, R6 is independently —OH. In embodiments, R6 is independently —NH$_2$. In embodiments, R6 is independently —COOH. In embodiments, R6 is independently —CONH$_2$. In embodiments, R6 is independently —NO$_2$. In embodiments, R6 is independently —SH. In embodiments, R6 is independently —SO$_3$H. In embodiments, R6 is independently —SO$_4$H. In embodiments, R6 is independently —SO$_2$NH$_2$. In embodiments, R6 is independently —NHNH$_2$. In embodiments, R6 is independently —ONH$_2$. In embodiments, R6 is independently —NHC(O)NHNH$_2$. In embodiments, R6 is independently —NHC(O)NH$_2$. In embodiments, R6 is independently —NHSO$_2$H. In embodiments, R6 is independently —NHC(O)H. In embodiments, R6 is independently —NHC(O)OH. In embodiments, R6 is independently —NHOH. In embodiments, R6 is independently —OCCl$_3$. In embodiments, R6 is independently —OCF$_3$. In embodiments, R6 is independently —OCBr$_3$. In embodiments, R6 is independently —OCI$_3$. In embodiments, R6 is independently —OCHCl$_2$. In embodiments, R6 is independently —OCHBr$_2$. In embodiments, R6 is independently —OCHI$_2$. In embodiments, R6 is independently —OCHF$_2$. In embodiments, R6 is independently —OCH$_2$Cl. In embodiments, R6 is independently —OCH$_2$Br. In embodiments, R6 is independently —OCH$_2$I. In embodiments, R6 is independently —OCH$_2$F. In embodiments, R6 is independently —SF$_5$. In embodiments, R6 is independently —N$_3$. In embodiments, R6 is independently substituted or unsubstituted alkyl (e.g., C$_1$-C$_8$ alkyl, C$_1$-C$_6$ alkyl, or C$_1$-C$_4$ alkyl). In embodiments, R6 is independently substituted or unsubstituted alkenyl (e.g., C$_2$-C$_8$ alkenyl, C$_2$-C$_6$ alkenyl, or C$_2$-C$_4$ alkenyl). In embodiments, R6 is independently substituted or unsubstituted alkynyl (e.g., C$_2$-C$_8$ alkynyl, C$_2$-C$_6$ alkynyl, or C$_2$-C$_4$ alkynyl). In embodiments, R6 is independently substituted or unsubstituted heteroalkyl (e.g., 2 to 8 membered heteroalkyl, 2 to 6 membered heteroalkyl, or 2 to 4 membered heteroalkyl). In embodiments, R6 is independently substituted or unsubstituted cycloalkyl (e.g., C$_3$-C$_8$, C$_3$-C$_6$, or C$_5$-C$_6$). In embodiments, R6 is independently substituted or unsubstituted cycloalkenyl (e.g., C$_3$-C$_8$, C$_3$-C$_6$, or C$_5$-C$_6$). In embodiments, R6 is independently substituted or unsubstituted cycloalkynyl (e.g., C$_3$-C$_8$, C$_3$-C$_6$, or C$_5$-C$_6$). In embodiments, R6 is independently substituted or unsubstituted aryl (e.g., C$_6$-C$_{10}$ aryl, C$_{10}$ aryl, or phenyl). In embodiments, R6 is independently substituted or unsubstituted heteroaryl (e.g., 5 to 10 membered heteroaryl, 5 to 9 membered heteroaryl, or 5 to 6 membered heteroaryl). In embodiments, R6 is independently substituted or unsubstituted heteroalicyclyl (e.g., 3 to 8 membered, 3 to 6 membered, or 5 to 6 membered). In embodiments, R6 is independently substituted or unsubstituted aralkyl. In embodiments, R6 is independently substituted or unsubstituted heteroaralkyl. In embodiments, R6 is independently substituted or unsubstituted (heteroalicyclyl)alkyl.

In embodiments, R6 is independently unsubstituted alkyl (e.g., $C_1$-$C_8$ alkyl, $C_1$-$C_6$ alkyl, or $C_1$-$C_4$ alkyl). In embodiments, R6 is independently unsubstituted alkenyl (e.g., $C_2$-$C_8$ alkenyl, $C_2$-$C_6$ alkenyl, or $C_2$-$C_4$ alkenyl). In embodiments, R6 is independently unsubstituted alkynyl (e.g., $C_2$-$C_8$ alkyl, $C_2$-$C_6$ alkyl, or $C_2$-$C_4$ alkyl). In embodiments, R6 is independently unsubstituted heteroalkyl (e.g., 2 to 8 membered heteroalkyl, 2 to 6 membered heteroalkyl, or 2 to 4 membered heteroalkyl). In embodiments, R6 is independently unsubstituted cycloalkyl (e.g., $C_3$-$C_8$, $C_3$-$C_6$, or $C_5$-$C_6$). In embodiments, R6 is independently unsubstituted cycloalkenyl (e.g., $C_3$-$C_8$, $C_3$-$C_6$, or $C_5$-$C_6$). In embodiments, R6 is independently unsubstituted cycloalkynyl (e.g., $C_3$-$C_8$, $C_3$-$C_6$, or $C_5$-$C_6$). In embodiments, R6 is independently unsubstituted aryl (e.g., $C_6$-$C_{10}$ aryl, $C_{10}$ aryl, or phenyl). In embodiments, R6 is independently unsubstituted heteroaryl (e.g., 5 to 10 membered heteroaryl, 5 to 9 membered heteroaryl, or 5 to 6 membered heteroaryl). In embodiments, R6 is independently unsubstituted heteroalicyclyl (e.g., 3 to 8 membered, 3 to 6 membered, or 5 to 6 membered). In embodiments, R6 is independently unsubstituted aralkyl. In embodiments, R6 is independently unsubstituted heteroaralkyl. In embodiments, R6 is independently unsubstituted (heteroalicyclyl)alkyl.

In embodiments, R7 is independently hydrogen. In embodiments, R7 is independently halogen. In embodiments, R7 is independently —$CCl_3$. In embodiments, R7 is independently —$CBr_3$. In embodiments, R7 is independently —$CF_3$. In embodiments, R7 is independently —$CI_3$. In embodiments, R7 is independently —$CHCl_2$. In embodiments, R7 is independently —$CHBr_2$. In embodiments, R7 is independently —$CHF_2$. In embodiments, R7 is independently —$CHI_2$. In embodiments, R7 is independently —$CH_2Cl$. In embodiments, R7 is independently —$CH_2Br$. In embodiments, R7 is independently —$CH_2F$. In embodiments, R7 is independently —$CH_2I$. In embodiments, R7 is independently —CN. In embodiments, R7 is independently —OH. In embodiments, R7 is independently —$NH_2$. In embodiments, R7 is independently —COOH. In embodiments, R7 is independently —$CONH_2$. In embodiments, R7 is independently —$NO_2$. In embodiments, R7 is independently —SH. In embodiments, R7 is independently —$SO_3H$. In embodiments, R7 is independently —$SO_4H$. In embodiments, R7 is independently —$SO_2NH_2$. In embodiments, R7 is independently —$NHNH_2$. In embodiments, R7 is independently —$ONH_2$. In embodiments, R7 is independently —NHC(O)$NHNH_2$. In embodiments, R7 is independently —NHC(O)$NH_2$. In embodiments, R7 is independently —$NHSO_2H$. In embodiments, R7 is independently —NHC(O)H. In embodiments, R7 is independently —NHC(O)OH. In embodiments, R7 is independently —NHOH. In embodiments, R7 is independently —$OCCl_3$. In embodiments, R7 is independently —$OCF_3$. In embodiments, R7 is independently —$OCBr_3$. In embodiments, R7 is independently —$OCI_3$. In embodiments, R7 is independently —$OCHCl_2$. In embodiments, R7 is independently —$OCHBr_2$. In embodiments, R7 is independently —$OCHI_2$. In embodiments, R7 is independently —$OCHF_2$. In embodiments, R7 is independently —$OCH_2Cl$. In embodiments, R7 is independently —$OCH_2Br$. In embodiments, R7 is independently —$OCH_2I$. In embodiments, R7 is independently —$OCH_2F$. In embodiments, R7 is independently —$SF_5$. In embodiments, R7 is independently —$N_3$. In embodiments, R7 is independently substituted or unsubstituted alkyl (e.g., $C_1$-$C_8$ alkyl, $C_1$-$C_6$ alkyl, or $C_1$-$C_4$ alkyl). In embodiments, R7 is independently substituted or unsubstituted alkenyl (e.g., $C_2$-$C_8$ alkenyl, $C_2$-$C_6$ alkenyl, or $C_2$-$C_4$ alkenyl). In embodiments, R7 is independently substituted or unsubstituted alkynyl (e.g., $C_2$-$C_8$ alkynyl, $C_2$-$C_6$ alkynyl, or $C_2$-$C_4$ alkynyl). In embodiments, R7 is independently substituted or unsubstituted heteroalkyl (e.g., 2 to 8 membered heteroalkyl, 2 to 6 membered heteroalkyl, or 2 to 4 membered heteroalkyl). In embodiments, R7 is independently substituted or unsubstituted cycloalkyl (e.g., $C_3$-$C_8$, $C_3$-$C_6$, or $C_5$-$C_6$). In embodiments, R7 is independently substituted or unsubstituted cycloalkenyl (e.g., $C_3$-$C_8$, $C_3$-$C_6$, or $C_5$-$C_6$). In embodiments, R7 is independently substituted or unsubstituted cycloalkynyl (e.g., $C_3$-$C_8$, $C_3$-$C_6$, or $C_5$-$C_6$). In embodiments, R7 is independently substituted or unsubstituted aryl (e.g., $C_6$-$C_{10}$ aryl, $C_{10}$ aryl, or phenyl). In embodiments, R7 is independently substituted or unsubstituted heteroaryl (e.g., 5 to 10 membered heteroaryl, 5 to 9 membered heteroaryl, or 5 to 6 membered heteroaryl). In embodiments, R7 is independently substituted or unsubstituted heteroalicyclyl (e.g., 3 to 8 membered, 3 to 6 membered, or 5 to 6 membered). In embodiments, R7 is independently substituted or unsubstituted aralkyl. In embodiments, R7 is independently substituted or unsubstituted heteroaralkyl. In embodiments, R7 is independently substituted or unsubstituted (heteroalicyclyl)alkyl.

In embodiments, R7 is independently unsubstituted alkyl (e.g., $C_1$-$C_8$ alkyl, $C_1$-$C_6$ alkyl, or $C_1$-$C_4$ alkyl). In embodiments, R7 is independently unsubstituted alkenyl (e.g., $C_2$-$C_8$ alkenyl, $C_2$-$C_6$ alkenyl, or $C_2$-$C_4$ alkenyl). In embodiments, R7 is independently unsubstituted alkynyl (e.g., $C_2$-$C_8$ alkynyl, $C_2$-$C_6$ alkynyl, or $C_2$-$C_4$ alkynyl). In embodiments, R7 is independently unsubstituted heteroalkyl (e.g., 2 to 8 membered heteroalkyl, 2 to 6 membered heteroalkyl, or 2 to 4 membered heteroalkyl). In embodiments, R7 is independently unsubstituted cycloalkyl (e.g., $C_3$-$C_8$, $C_3$-$C_6$, or $C_5$-$C_6$). In embodiments, R7 is independently unsubstituted cycloalkenyl (e.g., $C_3$-$C_8$, $C_3$-$C_6$, or $C_5$-$C_6$). In embodiments, R7 is independently unsubstituted cycloalkynyl (e.g., $C_3$-$C_8$, $C_3$-$C_6$, or $C_5$-$C_6$). In embodiments, R7 is independently unsubstituted aryl (e.g., $C_6$-$C_{10}$ aryl, $C_{10}$ aryl, or phenyl). In embodiments, R7 is independently unsubstituted heteroaryl (e.g., 5 to 10 membered heteroaryl, 5 to 9 membered heteroaryl, or 5 to 6 membered heteroaryl). In embodiments, R7 is independently unsubstituted heteroalicyclyl (e.g., 3 to 8 membered, 3 to 6 membered, or 5 to 6 membered). In embodiments, R7 is independently unsubstituted aralkyl. In embodiments, R7 is independently unsubstituted heteroaralkyl. In embodiments, R7 is independently unsubstituted (heteroalicyclyl)alkyl.

In embodiments, R8 is independently hydrogen. In embodiments, R8 is independently halogen. In embodiments, R8 is independently —$CCl_3$. In embodiments, R8 is independently —$CBr_3$. In embodiments, R8 is independently —$CF_3$. In embodiments, R8 is independently —$CI_3$. In embodiments, R8 is independently —$CHCl_2$. In embodiments, R8 is independently —$CHBr_2$. In embodiments, R8 is independently —$CHF_2$. In embodiments, R8 is independently —$CHI_2$. In embodiments, R8 is independently —$CH_2Cl$. In embodiments, R8 is independently —$CH_2Br$. In embodiments, R8 is independently —$CH_2F$. In embodiments, R8 is independently —$CH_2I$. In embodiments, R8 is independently —CN. In embodiments, R8 is independently —OH. In embodiments, R8 is independently —$NH_2$. In embodiments, R8 is independently —COOH. In embodiments, R8 is independently —CONH$_2$. In embodiments, R8 is independently —NO$_2$. In embodiments, R8 is independently —SH. In embodiments, R8 is independently —SO$_3$H. In embodiments, R8 is independently —SO$_4$H. In embodiments, R8 is independently —SO$_2$NH$_2$. In embodiments, R8 is independently —NHNH$_2$. In embodiments, R8 is independently —ONH$_2$. In embodiments, R8 is independently —NHC(O)NHNH$_2$. In embodiments, R8 is independently —NHC(O)NH$_2$. In embodiments, R8 is independently —NHSO$_2$H. In embodiments, R8 is independently —NHC(O)H. In embodiments, R8 is independently —NHC(O)OH. In embodiments, R8 is independently —NHOH. In embodiments, R8 is independently —OCCl$_3$. In embodiments, R8 is independently —OCF$_3$. In embodiments, R8 is independently —OCBr$_3$. In embodiments, R8 is independently —OCI$_3$. In embodiments, R8 is independently —OCHCl$_2$. In embodiments, R8 is independently —OCHBr$_2$. In embodiments, R8 is independently —OCHI$_2$. In embodiments, R8 is independently —OCHF$_2$. In embodiments, R8 is independently —OCH$_2$Cl. In embodiments, R8 is independently —OCH$_2$Br. In embodiments, R8 is independently —OCH$_2$I. In embodiments, R8 is independently —OCH$_2$F. In embodiments, R8 is independently —SF$_5$. In embodiments, R8 is independently —N$_3$. In embodiments, R8 is independently substituted or unsubstituted alkyl (e.g., C$_1$-C$_8$ alkyl, C$_1$-C$_6$ alkyl, or C$_1$-C$_4$ alkyl). In embodiments, R8 is independently substituted or unsubstituted alkenyl (e.g., C$_2$-C$_8$ alkenyl, C$_2$-C$_6$ alkenyl, or C$_2$-C$_4$ alkenyl). In embodiments, R8 is independently substituted or unsubstituted alkynyl (e.g., C$_2$-C$_8$ alkynyl, C$_2$-C$_6$ alkynyl, or C$_2$-C$_4$ alkynyl). In embodiments, R8 is independently substituted or unsubstituted heteroalkyl (e.g., 2 to 8 membered heteroalkyl, 2 to 6 membered heteroalkyl, or 2 to 4 membered heteroalkyl). In embodiments, R8 is independently substituted or unsubstituted cycloalkyl (e.g., C$_3$-C$_8$, C$_3$-C$_6$, or C$_5$-C$_6$). In embodiments, R8 is independently substituted or unsubstituted cycloalkenyl (e.g., C$_3$-C$_8$, C$_3$-C$_6$, or C$_5$-C$_6$). In embodiments, R8 is independently substituted or unsubstituted cycloalkynyl (e.g., C$_3$-C$_8$, C$_3$-C$_6$, or C$_5$-C$_6$). In embodiments, R8 is independently substituted or unsubstituted aryl (e.g., C$_6$-C$_{10}$ aryl, C$_{10}$ aryl, or phenyl). In embodiments, R8 is independently substituted or unsubstituted heteroaryl (e.g., 5 to 10 membered heteroaryl, 5 to 9 membered heteroaryl, or 5 to 6 membered heteroaryl). In embodiments, R8 is independently substituted or unsubstituted heteroalicyclyl (e.g., 3 to 8 membered, 3 to 6 membered, or 5 to 6 membered). In embodiments, R8 is independently substituted or unsubstituted aralkyl. In embodiments, R8 is independently substituted or unsubstituted heteroaralkyl. In embodiments, R8 is independently substituted or unsubstituted (heteroalicyclyl)alkyl.

In embodiments, R8 is independently unsubstituted alkyl (e.g., C$_1$-C$_8$ alkyl, C$_1$-C$_6$ alkyl, or C$_1$-C$_4$ alkyl). In embodiments, R8 is independently unsubstituted alkenyl (e.g., C$_2$-C$_8$ alkenyl, C$_2$-C$_6$ alkenyl, or C$_2$-C$_4$ alkenyl). In embodiments, R8 is independently unsubstituted alkynyl (e.g., C$_2$-C$_8$ alkynyl, C$_2$-C$_6$ alkynyl, or C$_2$-C$_4$ alkynyl). In embodiments, R8 is independently unsubstituted heteroalkyl (e.g., 2 to 8 membered heteroalkyl, 2 to 6 membered heteroalkyl, or 2 to 4 membered heteroalkyl). In embodiments, R8 is independently unsubstituted cycloalkyl (e.g., C$_3$-C$_8$, C$_3$-C$_6$, or C$_5$-C$_6$). In embodiments, R8 is independently unsubstituted cycloalkenyl (e.g., C$_3$-C$_8$, C$_3$-C$_6$, or C$_5$-C$_6$). In embodiments, R8 is independently unsubstituted cycloalkynyl (e.g., C$_3$-C$_8$, C$_3$-C$_6$, or C$_5$-C$_6$). In embodiments, R8 is independently unsubstituted aryl (e.g., C$_6$-C$_{10}$ aryl, C$_{10}$ aryl, or phenyl). In embodiments, R8 is independently unsubstituted heteroaryl (e.g., 5 to 10 membered heteroaryl, 5 to 9 membered heteroaryl, or 5 to 6 membered heteroaryl). In embodiments, R8 is independently unsubstituted heteroalicyclyl (e.g., 3 to 8 membered, 3 to 6 membered, or 5 to 6 membered). In embodiments, R8 is independently unsubstituted aralkyl. In embodiments, R8 is independently unsubstituted heteroaralkyl. In embodiments, R8 is independently unsubstituted (heteroalicyclyl)alkyl.

Optionally, the kit can include nitrous acid (HONO). For example, in a third vessel. In particular configurations, the nucleotide can have the structure:

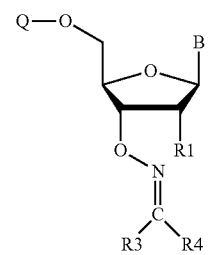

wherein B is a nucleobase; R1 is independently halogen, OCH$_3$, H or OH, Q is independently monophosphate, diphosphate, triphosphate, or nucleic acid, and R3 and R4 can independently be H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, Q is independently a single stranded deoxyribonucleic acid or double stranded deoxyribonucleic acid.

Any of the components or articles used in performing the methods set forth herein can be usefully packaged into a kit. For example, the kits can be packed to include some, many or all of the components or articles used in performing the methods set forth herein. Exemplary components include, for example, labeled nucleotides (e.g. extendible labeled nucleotides); polymerases (labeled or unlabeled); nucleotides having terminator moieties such as a —ONH$_2$ moiety (e.g. unlabeled, reversibly terminated nucleotides); reagents such as N-alkoxyamine reagents set forth herein; and the like as set forth herein and in references cited herein. Any of such reagents can include, for example, some, many or all of the fluids, components and/or articles used for performing one or more of the subsequent steps for analysis of a primed template nucleic acid. A kit need not include a primer or template nucleic acid. Rather, a user of the kit can provide a primed template nucleic acid which is to be combined with components of the kit. Similarly, a kit can exclude one or more of the components set forth herein (such as a flow cell or other vessel) and, optionally, such excluded components can be provided by an end user.

One or more ancillary reagents also can be included in a kit. Such ancillary reagents can include any of the reagents exemplified above and/or other types of reagents useful in performing the methods set forth herein. Instructions can further be included in a kit. The instructions can include, for example, procedures for making any components used in the methods set forth herein, performing one or more steps of any embodiment of the methods set forth herein and/or instructions for performing any of the subsequent analysis steps employing a primed template nucleic acid. For example, a kit can include instructions for extending a primer with a reversibly terminated nucleotide or a reversibly terminated oligonucleotide, or instructions for deblocking a reversibly terminated nucleotide or primer.

Optionally a kit can include identifying information in the form of a label that can be read by a human user. Labels that are machine readable such as bar codes, microchips or radio-frequency identification (RFID) tags can also be useful.

In particular embodiments, a kit includes a cartridge having reservoirs to contain the reagents and further having fluidic components for transferring reagents from the reservoirs to a detection instrument. For example, the fluidic components can be configured to transfer reagents to a flow cell where stabilized ternary complexes are detected. The cartridge can be configured for non-permanent introduction to a nucleic acid analysis system such as a nucleic acid sequencing platform. Accordingly, the cartridge can be configured for installation with, and removal from, a detection apparatus. An exemplary fluidic cartridge that can be included in a kit (or system) of the present disclosure is described in US Pat. App. Pub. Nos. 2018/0280975 A1 or 2019/0055596 A1, each of which is incorporated herein by reference.

In an aspect is provided a method of adding a 3'-O—NH$_2$ moiety to a nucleotide having a 3' protecting group, including contacting a nucleotide having a 3' protecting group to a reagent including the structure R2-O—NH$_2$, wherein R2 has a molecular weight of at least 24. In embodiments, the nucleotide having a 3' protecting group includes ribose or deoxyribose. In embodiments, the nucleotide having a 3' protecting group includes ribose. In embodiments, the nucleotide having a 3' protecting group includes 2' deoxyribose. In embodiments, the nucleotide having a 3' protecting group includes phosphate. In embodiments, the nucleotide having a 3' protecting group includes triphosphate. In embodiments, the nucleotide having a 3' protecting group includes the structure:

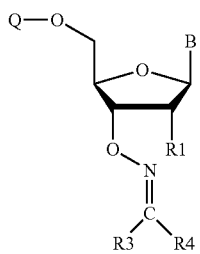

wherein the nucleotide that includes the 3'-O—NH$_2$ moiety includes the structure:

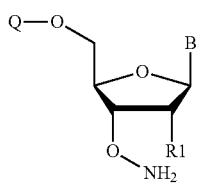

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, the 3' blocking group includes 3'-O-Oxime. In embodiments, the 3' blocking group includes 3'-O-aldoxime. In embodiments, the 3' blocking group includes 3'-O-ketoxime.

In embodiments, the nucleotide having a 3' protecting group includes the structure:

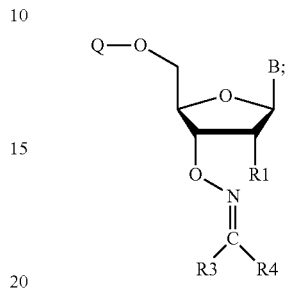

wherein the nucleotide that includes the 3'-O—NH$_2$ moiety includes the structure:

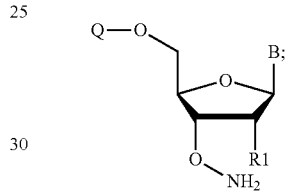

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, the method adds a 3' ONH$_2$ in place of a 3' protecting group to at least 94% of a population of nucleotides having a 3' protecting group in no more than 3 hours. In embodiments, the method adds a 3' ONH$_2$ in place of a 3' protecting group to at least 96% of a population of nucleotides having a 3' protecting group in no more than 3 hours. In embodiments, the method adds a 3' ONH$_2$ in place of a 3' protecting group to at least 98% of a population of nucleotides having a 3' protecting group in no more than 3 hours. In embodiments, the method adds a 3' ONH$_2$ in place of a 3' protecting group to at least 98% of a population of nucleotides having a 3' protecting group in no more than 1 hour.

In embodiments, the nucleotide having a 3' protecting group includes cytosine, and wherein method degrades no more than 6% of cytosine bases from a population including a plurality of the nucleotide having a 3' protecting group including cytosine. In embodiments, the nucleotide having a 3' protecting group includes cytosine, and wherein method degrades no more than 5% of cytosine bases from a population including a plurality of the nucleotide having a 3' protecting group including cytosine. In embodiments, the nucleotide having a 3' protecting group includes cytosine, and wherein method degrades no more than 4% of cytosine bases from a population including a plurality of the nucleotide having a 3' protecting group including cytosine. In embodiments, the nucleotide having a 3' protecting group includes cytosine, and wherein method degrades no more than 3% of cytosine bases from a population including a plurality of the nucleotide having a 3' protecting group including cytosine. In embodiments, the nucleotide having a 3' protecting group includes cytosine, and wherein method degrades no more than 2% of cytosine bases from a population including a plurality of the nucleotide having a 3' protecting group including cytosine. In embodiments, the nucleotide having a 3' protecting group includes cytosine, and wherein method degrades no more than 1% of cytosine bases from a population including a plurality of the nucleotide having a 3' protecting group including cytosine.

In an aspect is provided a method of making a 3'-blocked nucleotide, the method including contacting a 3'-protected nucleotide with a reagent having the structure R2-O—$NH_2$, R2-O—$NHCH_3$, R2-O—$NHCOCH_3$, or R2O—$CH_2N_3$ wherein R2 has a molecular weight of at least 24 g/mol and thereby making a 3'-blocked nucleotide from a 3'-protected nucleotide.

In embodiments, R2 has a molecular weight of at least 36. In embodiments, R2 includes a fluorine nucleus. In embodiments, R2 includes at least two carbon nuclei. In embodiments, R2 includes a carbon-carbon double bond. In embodiments, R2 includes a tertiary carbon. In embodiments, R2 includes a tert-butyl moiety. In embodiments, R2 includes a cyclic moiety. In embodiments, R2 includes a silicon nucleus. In embodiments, R2 includes a phenyl ring. In embodiments, R2 includes a nitrogen nucleus. In embodiments, R2 includes an oxygen nucleus. In embodiments, R2 includes a hydroxylate moiety.

In an aspect is provided a method of making a 3'-blocked nucleotide, the method including contacting a 3'-protected nucleotide with a reagent having the structure R2-O—$NH_2$ or R2O—$CH_2N_3$ wherein R2 has a molecular weight of at least 24 g/mol and thereby making a 3'-blocked nucleotide from a 3'-protected nucleotide.

In embodiments, the 3'-blocked nucleotide includes a blocking moiety bonded directly to the ribose 3' carbon of the nucleotide; and the blocking moiety is —$ONH_2$, —$ONHCOCH_3$, —$ONHCH_3$, —$OCH_2N_3$. In embodiments, the 3'-blocked nucleotide includes a blocking moiety bonded directly to the ribose 3' carbon of the nucleotide; and the blocking moiety is —$ONH_2$ or —$OCH_2N_3$. In embodiments, the 3'-blocked nucleotide includes a blocking moiety bonded directly to the ribose 3' carbon of the nucleotide; and the blocking moiety is —$ONH_2$.

In embodiments, the 3'-protected nucleotide comprises a protecting moiety directly covalently bonded to the ribose 3' carbon of the nucleotide; and the protecting moiety is a 3'-O-oxime moiety.

In embodiments, the —O-oxime moiety has the formula: —O—N═C(R3)(R4); and R3 and R4 are independently hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

In embodiments, the —O-oxime moiety has the formula: —O—N═C(R3)(R4); R3 is hydrogen; and R4 is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

In embodiments, the —O-oxime moiety has the formula: —O—N═C(R3)(R4); and R3 and R4 are independently substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

In embodiments, the 3'-blocked nucleotide and the 3'-protected nucleotide include an adenine moiety or derivative thereof, guanine moiety or derivative thereof, cytosine moiety or derivative thereof, thymine moiety or derivative thereof, or uracil moiety or derivative thereof. In embodiments, the adenine derivative moiety, guanine derivative moiety, cytosine derivative moiety, thymine derivative moiety, and uracil derivative moiety include a detectable moiety.

In embodiments, the 3'-blocked nucleotide and the 3'-protected nucleotide include a monophosphate moiety or derivative thereof, diphosphate moiety or derivative thereof, triphosphate moiety or derivative thereof, or monovalent nucleic acid moiety or derivative thereof. In embodiments, the 3'-blocked nucleotide and the 3'-protected nucleotide include a monophosphate moiety, diphosphate moiety, triphosphate moiety, or monovalent nucleic acid moiety. In embodiments, the 3'-blocked nucleotide and the 3'-protected nucleotide comprise a triphosphate moiety. In embodiments, the 3'-blocked nucleotide and the 3'-protected nucleotide comprise a monovalent nucleic acid moiety. In embodiments, the 3'-blocked nucleotide and the 3'-protected nucleotide comprise a ribose moiety. In embodiments, the 3'-blocked nucleotide and the 3'-protected nucleotide comprise a 2' deoxyribose moiety.

In embodiments, R2 has a molecular weight of 1000 g/mol or less. In embodiments, R2 has a molecular weight of at least 36 g/mol. In embodiments, R2 has a molecular weight of at least 57 g/mol.

In embodiments, R2 includes at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety.

In embodiments, R2 is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R2 is not unsubstituted methyl. In embodiments, R2 is not unsubstituted ethyl. In embodiments, R2 is not unsubstituted propyl.

In embodiments, R2 is —C(R6)(R7)(R8), —C(O)(R6), —P(O)(R6)(R7), —C(R6)(═C(R7)(R8)), —Si(R6)(R7)(R8), —$SO_2$(R6), substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl; and R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R2 is —C(R6)(R7)(R8) and R6, R7, and R8 are not all hydrogen.

In embodiments, R2 is —C(R6)(R7)(R8), —C(O)(R6), —P(O)(R6)(R7), —C(R6)(=C(R7)(R8)), —Si(R6)(R7)(R8), —SO$_2$(R6), unsubstituted 6 membered heteroalicyclyl, unsubstituted phenyl, substituted or unsubstituted heteroaryl; and R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R6, R7, and R8 are not all hydrogen.

In embodiments, the reagent has the formula:

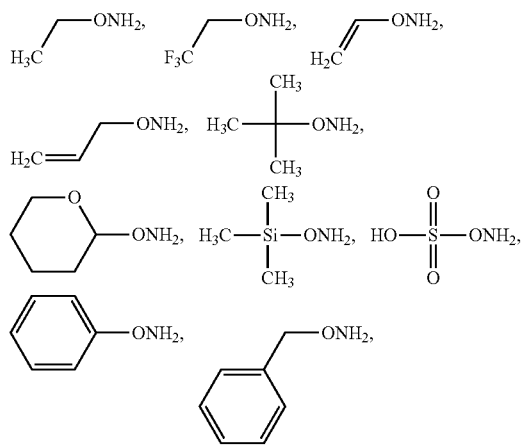

In embodiments, the reagent has the formula:

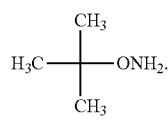

In embodiments, the 3'-protected nucleotide has the structure:

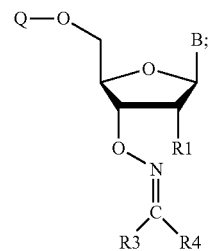

the 3'-blocked nucleotide has the structure:

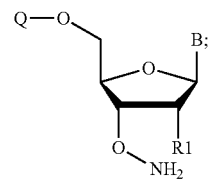

B is a nucleobase; R1 is hydrogen, —OH, halogen, —OCH$_3$; Q is independently a nucleic acid moiety, triphosphate moiety, diphosphate moiety, or monophosphate moiety; R3 and R4 are independently hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

In embodiments, the method adds a 3' $ONH_2$ in place of a 3' protecting group to at least 94% of a population of nucleotides having a 3' protecting group in no more than 3 hours. In embodiments, the method adds a 3' $ONH_2$ in place of a 3' protecting group to at least 98% of a population of nucleotides having a 3' protecting group in no more than 1 hour.

In embodiments, the nucleotide having a 3' protecting group includes cytosine, and wherein method degrades no more than 6% of cytosine bases from a population including a plurality of said nucleotide having a 3' protecting group including cytosine. In embodiments, the nucleotide having a 3' protecting group includes cytosine, and wherein method degrades no more than 1% of cytosine bases from a population including a plurality of said nucleotide having a 3' protecting group including cytosine.

In embodiments, the method further includes making a first plurality of 3'-blocked nucleotides, the method including contacting a second plurality of 3'-protected nucleotides with a third plurality of the reagent and thereby making a first plurality of 3'-blocked nucleotides from a second plurality of 3'-protected nucleotides. In embodiments, the first plurality of 3'-blocked nucleotides are made for 3 hours or less. In embodiments, the first plurality of 3'-blocked nucleotides are made for 2 hours or less. In embodiments, the first plurality of 3'-blocked nucleotides are made for 1 hour or less.

In embodiments, at least 94% of the first plurality of 3'-protected nucleotide is made into the second plurality of 3'-blocked nucleotides. In embodiments, at least 96% of the first plurality of 3'-protected nucleotide is made into the second plurality of 3'-blocked nucleotides. In embodiments, at least 98% of the first plurality of 3'-protected nucleotide is made into the second plurality of 3'-blocked nucleotides.

In embodiments, the first plurality of 3'-blocked nucleotides includes a fourth plurality of 3'-blocked nucleotides including a cytosine; and 6% or less of the cytosines are chemically modified by the third plurality of the reagent. In embodiments, the first plurality of 3'-blocked nucleotides includes a fourth plurality of 3'-blocked nucleotides including a cytosine; and 5% or less of the cytosines are chemically modified by the third plurality of the reagent. In embodiments, the first plurality of 3'-blocked nucleotides includes a fourth plurality of 3'-blocked nucleotides including a cytosine; and 4% or less of the cytosines are chemically modified by the third plurality of the reagent. In embodiments, the first plurality of 3'-blocked nucleotides includes a fourth plurality of 3'-blocked nucleotides including a cytosine; and 3% or less of the cytosines are chemically modified by the third plurality of the reagent. In embodiments, the first plurality of 3'-blocked nucleotides includes a fourth plurality of 3'-blocked nucleotides including a cytosine; and 2% or less of the cytosines are chemically modified by the third plurality of the reagent. In embodiments, the first plurality of 3'-blocked nucleotides includes a fourth plurality of 3'-blocked nucleotides including a cytosine; and 1% or less of the cytosines are chemically modified by the third plurality of the reagent.

In an aspect is provided a composition including a population of cytosine nucleotides wherein at least 94% of the population of cytosine nucleotides include a 3'-O—$NH_2$, wherein no more than 8% of the population of cytosine nucleotides include a 3' moiety other than —O—$NH_2$, and wherein no more than 6% of the population of cytosine nucleotides include a modified cytosine base.

In embodiments, at least 96% of the population of cytosine nucleotides include a 3'-O—$NH_2$. In embodiments, at least 98% of the population of cytosine nucleotides include a 3'-O—$NH_2$. In embodiments, at least 99% of the population of cytosine nucleotides include a 3'-O—$NH_2$.

In embodiments, no more than 6% of the population of cytosine nucleotides include a 3' moiety other than —O—$NH_2$. In embodiments, no more than 4% of the population of cytosine nucleotides include a 3' moiety other than —O—$NH_2$. In embodiments, no more than 2% of the population of cytosine nucleotides include a 3' moiety other than —O—$NH_2$. In embodiments, no more than 1% of the population of cytosine nucleotides include a 3' moiety other than —O—$NH_2$.

In embodiments, no more than 4% of the population of cytosine nucleotides include a modified cytosine base. In embodiments, no more than 2% of the population of cytosine nucleotides include a modified cytosine base. In embodiments, no more than 1% of the population of cytosine nucleotides include a modified cytosine base.

In embodiments, at least 98% of the population of cytosine nucleotides include a 3'-O—$NH_2$, wherein no more than 1% of the population of cytosine nucleotides include a 3' moiety other than —O—$NH_2$, and wherein no more than 1% of the population of cytosine nucleotides include a modified cytosine base.

In embodiments, the composition is an aqueous solution. In embodiments, the pH of the solution is no less than 4 and no greater than 8.

In embodiments, the composition includes a reagent including the structure R2-O—$NH_2$. In embodiments, R2 includes a molecular weight of at least 24, 26, 57, or 100. In embodiments, R2 includes a molecular weight of at least 24. In embodiments, R2 includes a molecular weight of at least 36. In embodiments, R2 includes at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety. In embodiments, R2 includes at least two carbon nuclei. In embodiments, R2 includes a fluorine nucleus. In embodiments, R2 includes a carbon-carbon double bond. In embodiments, R2 includes a tertiary carbon. In embodiments, R2 includes a tert-butyl moiety. In embodiments, R2 includes a cyclic moiety. In embodiments, R2 includes a silicon nucleus. In embodiments, R2 includes a phenyl ring. In embodiments, R2 includes a nitrogen nucleus. In embodiments, R2 includes a phenyl ring. In embodiments, R2 includes an oxygen nucleus. In embodiments, R2 includes a hydroxylated moiety.

In embodiments, the reagent including the structure R2-O—$NH_2$ is selected from the group consisting of:

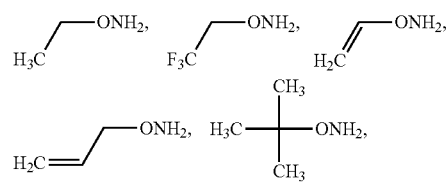

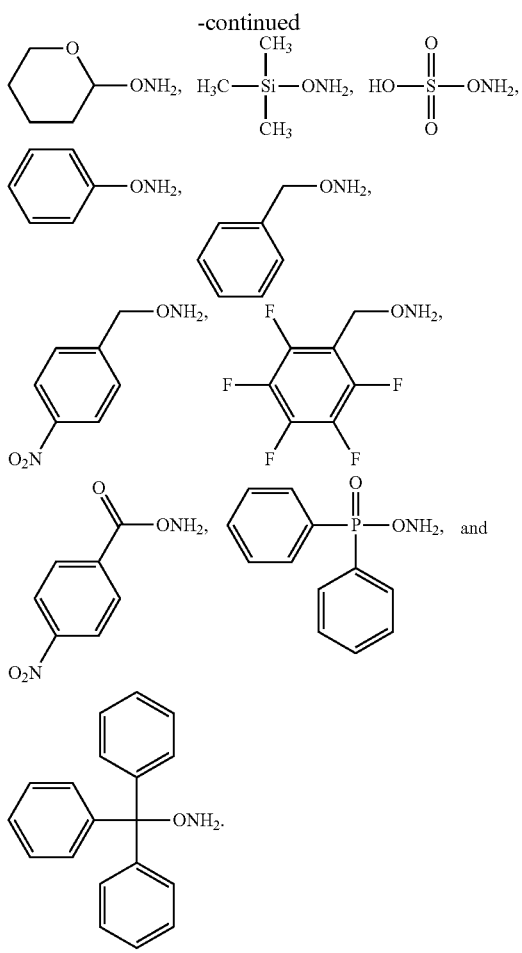

In embodiments, the reagent including the structure R2-O—NH₂ is selected from the group consisting of:

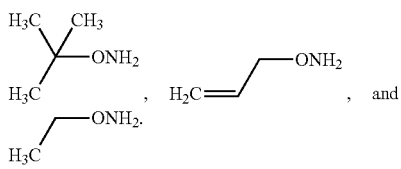

In embodiments, the reagent including the structure R2-O—NH₂ is

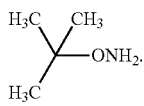

In embodiments, the reagent including the structure R2-O—NH₂ is

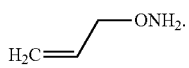

In embodiments, the reagent including the structure R2-O—NH₂ is

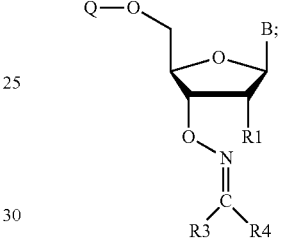

In embodiments, the 3' moiety other than —O—NH₂ includes a 3' O-oxime. In embodiments, the 3' moiety other than —O—NH₂ includes a 3' O-aldoxime. In embodiments, the 3' moiety other than —O—NH₂ includes a 3' O-ketoxime.

In embodiments, the composition includes a reagent including the structure R2-O—NHCH₃ or R2O—CH₂N₃. In embodiments, the composition includes a reagent including the structure R2-O—NHCH₃. In embodiments, the composition includes a reagent including the structure R2O—CH₂N₃.

In embodiments, at least some of the cytosine nucleotides having a 3' moiety other than —O—NH₂ nucleotide include the structure:

wherein B is a cytosine nucleobase; R1 is independently halogen, OCH₃, H or OH, Q is independently monophosphate, diphosphate, triphosphate, or nucleic acid, and R3 and R4 are independently H, CH₃, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In an aspect is provided a method of formulating a sequencing reagent, including contacting a composition including a 3' protected nucleotide to a reagent including a reversible terminator moiety to produce a composition including a nucleotide including a reversible terminator moiety, and formulating the composition including a nucleotide including a reversible terminator moiety as a sequencing reagent, wherein formulating the composition including a reversible terminator moiety does not include further purification of the composition including a reversible terminator moiety.

In embodiments, the method further includes applying the sequencing reagent to a sequencing reagent to yield a sequencing run of at least 100 bases having a quality score of at least Q30. In embodiments, the reagent including a reversible terminator moiety has a structure R2-O—NH₂.

In embodiments, R2 is selected from the group consisting of —C(R6)(R7)(R8), —C(O)(R6), —P(O)(R6)(R7), —C(R6)(=C(R7)(R8)), —Si(R6)(R7)(R8), —SO₂(R6), substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl; and R6, R7, and R8 are independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —SF₅, —N₃, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R2 is —C(CH₃)₃. In embodiments, R2 is —C(R6)(R7)(R8) and R6, R7, and R8 are not all hydrogen.

In embodiments, R2 includes at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety. In embodiments, R2 includes at least two carbon nuclei, carbon-carbon double bond, tertiary carbon, tert-butyl moiety, cyclic moiety, or phenyl ring. In embodiments, R2 includes at least two carbon nuclei. In embodiments, R2 includes a fluorine nucleus, silicon nucleus, nitrogen nucleus, oxygen nucleus, or hydroxylate moiety. In embodiments, R2 is —CH₂CH₃, —CH₂CHCH₂, or —C(CH₃)₃. In embodiments, R2 is-C(CH₃)₃. In embodiments, R2 is not unsubstituted methyl. In embodiments, R2 is not unsubstituted ethyl. In embodiments, R2 is not unsubstituted propyl.

In embodiments, R2 has a molecular weight greater than 24, 36, 57, or 100. In embodiments, R2 has a molecular weight of at least 24, 36, 57, 100, 200, 300, 400, 500, 600, 700, 800, or 900. In embodiments, R2 has a molecular weight of at least 24. In embodiments, R2 has a molecular weight of at least 36. In embodiments, R2 has a molecular weight of at least 57. In embodiments, R2 has a molecular weight of at least 100. In embodiments, R2 has a molecular weight of at least 200. In embodiments, R2 has a molecular weight of at least 300. In embodiments, R2 has a molecular weight of at least 400. In embodiments, R2 has a molecular weight of at least 500. In embodiments, R2 has a molecular weight of at least 600. In embodiments, R2 has a molecular weight of at least 700. In embodiments, R2 has a molecular weight of at least 800. In embodiments, R2 has a molecular weight of at least 900.

In embodiments, the 3' protected nucleotide includes a 3'-O-oxime moiety. In embodiments, the oxime is an aldoxime or ketoxime. In embodiments, the oxime is an aldoxime. In embodiments, the oxime is a ketoxime.

In embodiments, the composition including a nucleotide including a reversible terminator moiety includes no more than 6% of the 3' protected nucleotide relative to 3' protected nucleotide present initially. In embodiments, the composition including a nucleotide including a reversible terminator moiety includes no more than 5%, 4%, 3%, 2%, or 1% of the 3' protected nucleotide relative to 3' protected nucleotide present initially. In embodiments, the composition including a nucleotide including a reversible terminator moiety includes no more than 5% of the 3' protected nucleotide relative to 3' protected nucleotide present initially. In embodiments, the composition including a nucleotide including a reversible terminator moiety includes no more than 4% of the 3' protected nucleotide relative to 3' protected nucleotide present initially. In embodiments, the composition including a nucleotide including a reversible terminator moiety includes no more than 3% of the 3' protected nucleotide relative to 3' protected nucleotide present initially. In embodiments, the composition including a nucleotide including a reversible terminator moiety includes no more than 2% of the 3' protected nucleotide relative to 3' protected nucleotide present initially. In embodiments, the composition including a nucleotide including a reversible terminator moiety includes no more than 1% of the 3' protected nucleotide relative to 3' protected nucleotide present initially.

In embodiments, the composition including a nucleotide including a reversible terminator moiety includes degraded or modified dC nucleobases at a concentration of no more than 6% of total dC nucleobases in the composition including a nucleotide including a reversible terminator moiety. In embodiments, the composition including a nucleotide including a reversible terminator moiety includes degraded or modified dC nucleobases at a concentration of no more than 5%, 4%, 3%, 2%, or 1% of total dC nucleobases in the composition including a nucleotide including a reversible terminator moiety. In embodiments, the composition including a nucleotide including a reversible terminator moiety includes degraded or modified dC nucleobases at a concentration of no more than 5% of total dC nucleobases in the composition including a nucleotide including a reversible terminator moiety. In embodiments, the composition including a nucleotide including a reversible terminator moiety includes degraded or modified dC nucleobases at a concentration of no more than 4% of total dC nucleobases in the composition including a nucleotide including a reversible terminator moiety. In embodiments, the composition including a nucleotide including a reversible terminator moiety includes degraded or modified dC nucleobases at a concentration of no more than 3% of total dC nucleobases in the composition including a nucleotide including a reversible terminator moiety. In embodiments, the composition including a nucleotide including a reversible terminator moiety includes degraded or modified dC nucleobases at a concentration of no more than 2% of total dC nucleobases in the composition including a nucleotide including a reversible terminator moiety. In embodiments, the composition including a nucleotide including a reversible terminator moiety includes degraded or modified dC nucleobases at a concentration of no more than 1% of total dC nucleobases in the composition including a nucleotide including a reversible terminator moiety.

In an aspect is provided a method for modifying a nucleotide, including reacting a nucleotide including a 3'-O-oxime moiety with a reagent including the structure R2-O—NH₂ to produce a nucleotide including a 3'-O—NH₂ moiety, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, the nucleotide that includes the 3'-O-oxime moiety includes the structure:

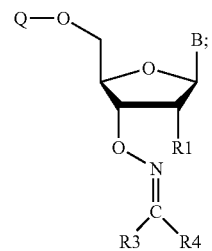

wherein the nucleotide that includes the 3'-O—NH$_2$ moiety includes the structure:

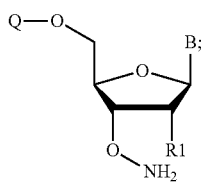

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, the nucleotide that is produced includes a deoxynucleotide. In embodiments, the nucleotide that is produced includes:

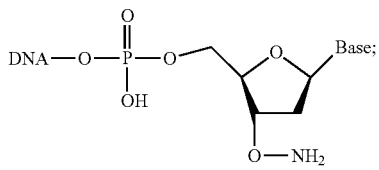

wherein Base is the nucleobase, and wherein DNA is independently a single stranded deoxyribonucleic acid or double stranded deoxyribonucleic acid.

In embodiments, the nucleobase is a purine or pyrimidine. In embodiments, the nucleobase is independently adenine, cytosine, guanine, thymine, or uracil. In embodiments, the nucleobase is independently 5-methylcytosine, hypoxanthine, xanthine, inosine, isoguanine, isocytosine, or 7-deazaguanine.

In embodiments, the reagent is independently one of:

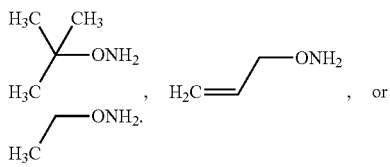

In embodiments, the reaction occurs in an aqueous solution. In embodiments, the nucleotide is attached to a solid support in contact with the aqueous solution. In embodiments, the reagent that includes the structure R2-O—NH$_2$ is attached to a solid support in contact with the aqueous solution. In embodiments, the pH of the solution is no less than 4 and no greater than 8.

In an aspect is provided a solution including a nucleotide including a 3'-O-oxime moiety and a reagent including the structure R2-O—NH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof. In embodiments, R2 is not unsubstituted methyl. In embodiments, R2 is not unsubstituted ethyl. In embodiments, R2 is not unsubstituted propyl.

In embodiments, the nucleotide includes the structure:

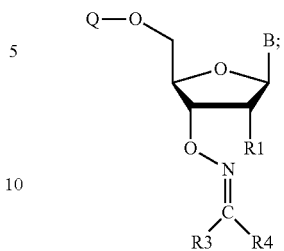

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, the nucleobase is a purine or pyrimidine. In embodiments, the nucleobase is independently adenine, cytosine, guanine, thymine, or uracil. In embodiments, the nucleobase is complementary to adenine, cytosine, guanine, thymine, or uracil. In embodiments, the nucleobase is independently 5-methylcytosine, hypoxanthine, xanthine, inosine, isoguanine, isocytosine, or 7-deazaguanine. In embodiments, the nucleobase includes an exogenous label moiety.

In embodiments, R1 is H. In embodiments, Q is deoxyribonucleic acid. In embodiments, R1 is OH. In embodiments, Q is ribonucleic acid.

In embodiments, the R2-O—NH$_2$ molecule is independently one of:

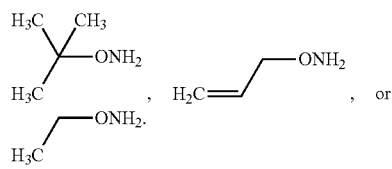

In embodiments, the solution is an aqueous solution. In embodiments, the nucleotide is attached to a solid support and wherein the solid support is in contact with the solution. In embodiments, the reagent that includes the structure R2-O—NH$_2$ is attached to a solid support in contact with the aqueous solution. In embodiments, the pH of the solution is no less than 4 and no greater than 8.

In an aspect is provided a method of sequencing a nucleic acid including the steps:
A. making a 3'-blocked nucleotide using a method described herein, including in embodiments, wherein the method of making does not include isolating the 3'-blocked nucleotide from the composition including the reactants and products of contacting the 3'-protected nucleotide with the reagent;
B. contacting the composition including the 3'-blocked nucleotide of step A with a nucleic acid template, primer, and polymerase in a reaction vessel;
C. identifying the 3'-blocked nucleotide that simultaneously contacts the template nucleic acid, 3' terminus of the primer, and polymerase; and optionally covalently binding the 3'-blocked nucleotide to the 3' terminus of the primer, making an extended primer; and thereby identifying the cognate nucleotide of the template nucleic acid to the 3'-blocking nucleotide;

D. removing the 3'-blocking moiety from the 3'-blocked nucleotide of the extended primer of step C; and E. repeating steps B to D and thereby sequencing the template nucleic acid.

In embodiments, step E is executed at least 99 times. In embodiments, the composition includes reagent $R2\text{-}ONH_2$. In embodiments, the reagent R2 is unsubstituted t-butyl. In embodiments, the reagent R2 is not hydrogen. In embodiments, the reagent R2 is not unsubstituted methyl. In embodiments, the reagent R2 is not unsubstituted ethyl. In embodiments, the reagent R2 is not unsubstituted propyl. In embodiments, the composition does not include $HONH_2$. In embodiments, the composition does not include $CH_3ONH_2$.

In embodiments, the quality score of the sequencing is at least Q20. In embodiments, the quality score of the sequencing is at least Q30. In embodiments, the quality score of the sequencing is at least Q50.

In an aspect is provided a kit including a first vessel containing a 3'-blocked nucleotide and a second vessel containing a reagent having the formula $R2\text{-}O\text{---}NH_2$, $R2\text{-}O\text{---}NHCH_3$, or $R2O\text{---}CH_2N_3$ wherein R2 has a molecular weight of at least 24 g/mol.

In embodiments, the 3'-blocked nucleotide includes a blocking moiety bonded directly to the ribose 3' carbon of the nucleotide; and the blocking moiety is $\text{---}ONH_2$, $\text{---}ONHCH_3$, or $\text{---}OCH_2CH_3$. In embodiments, the 3'-blocked nucleotide includes a blocking moiety bonded directly to the ribose 3' carbon of the nucleotide; and the blocking moiety is $\text{---}ONH_2$.

In embodiments, the 3'-protected nucleotide includes a protecting moiety directly covalently bonded to the ribose 3' carbon of the nucleotide; and the protecting moiety is a 3' oxime moiety.

In embodiments, the ---O-oxime moiety has the formula: $\text{---}O\text{---}N\text{=}C(R3)(R4)$; and R3 and R4 are independently hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

In embodiments, the ---O-oxime moiety has the formula: $\text{---}O\text{---}N\text{=}C(R3)(R4)$; R3 is hydrogen; and R4 is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

In embodiments, the ---O-oxime moiety has the formula: $\text{---}O\text{---}N\text{=}C(R3)(R4)$; and R3 and R4 are independently substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

In embodiments, the 3'-blocked nucleotide and the 3'-protected nucleotide include an adenine moiety or derivative thereof, guanine moiety or derivative thereof, cytosine moiety or derivative thereof, thymine moiety or derivative thereof, or uracil moiety or derivative thereof. In embodiments, the adenine derivative moiety, guanine derivative moiety, cytosine derivative moiety, thymine derivative moiety, and uracil derivative moiety include a detectable moiety. In embodiments, the 3'-blocked nucleotide and the 3'-protected nucleotide include a monophosphate moiety or derivative thereof, diphosphate moiety or derivative thereof, triphosphate moiety or derivative thereof, or monovalent nucleic acid moiety or derivative thereof. In embodiments, the 3'-blocked nucleotide and the 3'-protected nucleotide include a monophosphate moiety, diphosphate moiety, triphosphate moiety, or monovalent nucleic acid moiety. In embodiments, the 3'-blocked nucleotide and the 3'-protected nucleotide include a triphosphate moiety. In embodiments, the 3'-blocked nucleotide and the 3'-protected nucleotide include a monovalent nucleic acid moiety. In embodiments, the 3'-blocked nucleotide and the 3'-protected nucleotide include a ribose moiety. In embodiments, the 3'-blocked nucleotide and the 3'-protected nucleotide include a 2' deoxyribose moiety.

In embodiments, R2 has a molecular weight of 1000 g/mol or less. In embodiments, R2 has a molecular weight of at least 36 g/mol. In embodiments, R2 has a molecular weight of at least 57 g/mol.

In embodiments, R2 is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R2 is not unsubstituted methyl. In embodiments, R2 is not unsubstituted ethyl. In embodiments, R2 is not unsubstituted propyl.

In embodiments, R2 is $\text{---}C(R6)(R7)(R8)$, $\text{---}C(O)(R6)$, $\text{---}P(O)(R6)(R7)$, $\text{---}C(R6)(\text{=}C(R7)(R8))$, $\text{---}Si(R6)(R7)(R8)$, $\text{---}SO_2(R6)$, substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl; and R6, R7, and R8 are independently hydrogen, halogen, $\text{---}CCl_3$, $\text{---}CBr_3$, $\text{---}CF_3$, $\text{---}CI_3$, $\text{---}CHCl_2$, $\text{---}CHBr_2$, $\text{---}CHF_2$, $\text{---}CHI_2$, $\text{---}CH_2Cl$, $\text{---}CH_2Br$, $\text{---}CH_2F$, $\text{---}CH_2I$, $\text{---}CN$, $\text{---}OH$, $\text{---}NH_2$, $\text{---}COOH$, $\text{---}CONH_2$, $\text{---}NO_2$, $\text{---}SH$, $\text{---}SO_3H$, $\text{---}SO_4H$, $\text{---}SO_2NH_2$, $\text{---}NHNH_2$, $\text{---}ONH_2$, $\text{---}NIC(O)NHNH_2$, $\text{---}NHC(O)NH_2$, $\text{---}NHSO_2H$, $\text{---}NHC(O)H$, $\text{---}NHC(O)OH$, $\text{---}NHOH$, $\text{---}OCCl_3$, $\text{---}OCF_3$, $\text{---}OCBr_3$, $\text{---}OC_3$, $\text{---}OCHCl_2$, $\text{---}OCHBr_2$, $\text{---}OCHI_2$, $\text{---}OCHF_2$, $\text{---}OCH_2Cl$, $\text{---}OCH_2Br$, $\text{---}OCH_2I$, $\text{---}OCH_2F$, $\text{---}SF_5$, $\text{---}N_3$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R2 is —C(R6)(R7)(R8) and R6, R7, and R8 are not all hydrogen.

In embodiments, R2 is —C(R6)(R7)(R8), —C(O)(R6), —P(O)(R6)(R7), —C(R6)(=C(R7)(R8)), —Si(R6)(R7)(R8), —SO₂(R6), unsubstituted 6 membered heteroalicyclyl, unsubstituted phenyl, substituted or unsubstituted heteroaryl; and R6, R7, and R8 are independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OC₃, —OCHCl₂, —OCHBr₂, —OCHI₂, —OCHF₂, —OCH₂Cl, —OCH₂Br, —OCH₂I, —OCH₂F, —SF₅, —N₃, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R2 is —C(R6)(R7)(R8) and R6, R7, and R8 are not all hydrogen.

In embodiments, the reagent has the formula:

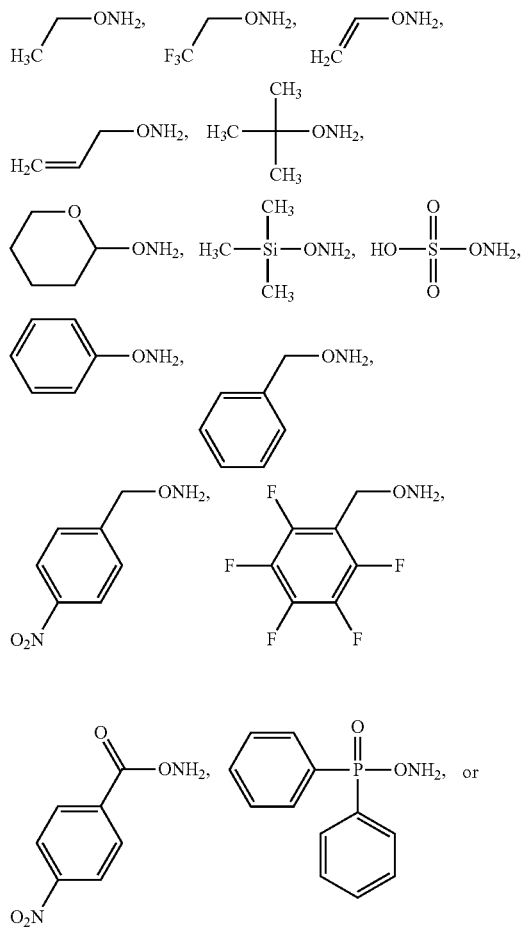

-continued

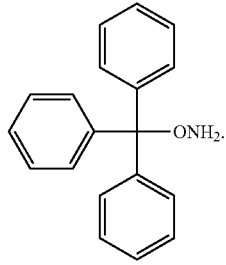

In embodiments, the reagent has the formula:

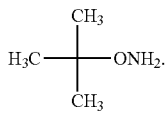

In embodiments, the 3'-protected nucleotide has the structure:

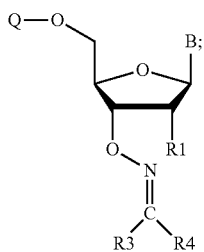

the 3'-blocked nucleotide has the structure:

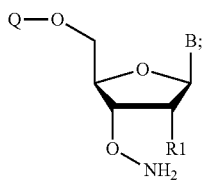

B is a nucleobase; R1 is hydrogen, —OH, halogen, —OCH₃; Q is independently a nucleic acid moiety, triphosphate moiety, diphosphate moiety, or monophosphate moiety; and R3 and R4 are independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

In an aspect is provided a kit including a first vessel containing a nucleotide including a 3'-O-oxime moiety and a second vessel containing a reagent including the structure R2-O—NH₂, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, the nucleotide includes the structure:

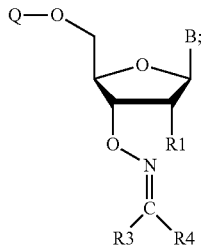

wherein B is a nucleobase; R1 is independently halogen, OCH₃, H or OH, Q is independently monophosphate, diphosphate, triphosphate, or nucleic acid, and R3 and R4 are independently H, CH₃, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, the nucleobase is a purine or pyrimidine. In embodiments, the nucleobase is independently adenine, cytosine, guanine, thymine, or uracil. In embodiments, the nucleobase is complementary to adenine, cytosine, guanine, thymine, or uracil. In embodiments, the nucleobase is independently 5-methylcytosine, hypoxanthine, xanthine, inosine, isoguanine, isocytosine, or 7-deazaguanine. In embodiments, the nucleobase includes an exogenous label moiety.

In embodiments, Q is independently a single stranded deoxyribonucleic acid or double stranded deoxyribonucleic acid.

In embodiments, the R2-O—NH₂ molecule is independently one of:

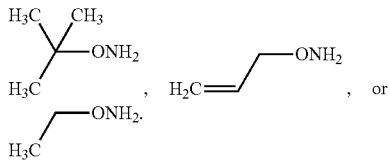

In embodiments, the kit includes an RFID tag or bar code.

In embodiments, the nucleotide is attached to a solid support. In embodiments, the reagent that includes the structure R2-O—NH₂ is attached to a solid support.

In an aspect is provided a method of replacing a protecting group by a blocking group at a 3' position of a nucleotide, including contacting the nucleotide and a reagent including the structure R2-block, wherein R2 has a molecular weight of at least 24, wherein R2-block is water soluble, and wherein block includes a blocking group moiety. In embodiments, block comprises a reversible terminator moiety. In embodiments, the reversible terminator moiety does not preclude assembly of a nucleotide reversibly terminated thereby into a ternary complex.

In embodiments, R2-block is selected from the group consisting of R2-O—NH₂, R2-O—NHCH₃, R2-O—NHCOCH₃, or R2O—CH₂N₃. In embodiments, R2-block is R2-O—NH₂. In embodiments, R2-block is R2-O—NHCH₃. In embodiments, R2-block is R2-O—NHCOCH₃. In embodiments, R2-block is R2O—CH₂N₃.

In embodiments, the nucleotide including a 3' protecting group is:

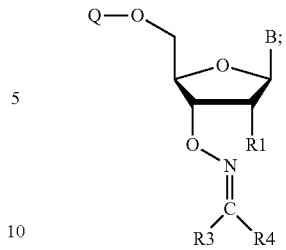

wherein the nucleotide including a 3' blocking group is:

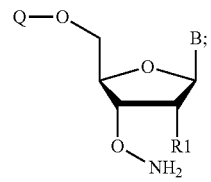

wherein B is a nucleobase; R1 is independently halogen, OCH₃, H or OH, Q is independently monophosphate, diphosphate, triphosphate, or nucleic acid, and R3 and R4 are independently H, CH₃, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

In embodiments, the protecting group includes an O-oxime. In embodiments, the oxime moiety has the formula: —O—N=C(R3)(R4); and R3 and R4 are independently hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R3 is Hydrogen. In embodiments, R4 is Hydrogen. In embodiments, the nucleotide comprises a triphosphate moiety.

In embodiments, R2 is —C(R6)(R7)(R8), —C(O)(R6), —P(O)(R6)(R7), —C(R6)(=C(R7)(R8)), —Si(R6)(R7)(R8), —SO₂(R6), substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl; and R6, R7, and R8 are independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NIC(O)NHNH₂, —NHC(O)NH₂, —NHSO₂H, —NHC(O)H, —NHC(O)OH, —NHOH, —OCCl₃, —OCF₃, —OCBr₃, —OC₃, —OCHCl₂, —OCHBr₂, —OCHI₂, —OCHF₂, —OCH₂Cl, —OCH₂Br, —OCH₂I, —OCH₂F, —SF₅, —N₃, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl. In embodiments, R2 is —C(R6)(R7)(R8) and R6, R7, and R8 are not all hydrogen.

In embodiments, R2-block has a formula selected from the group consisting of the following:

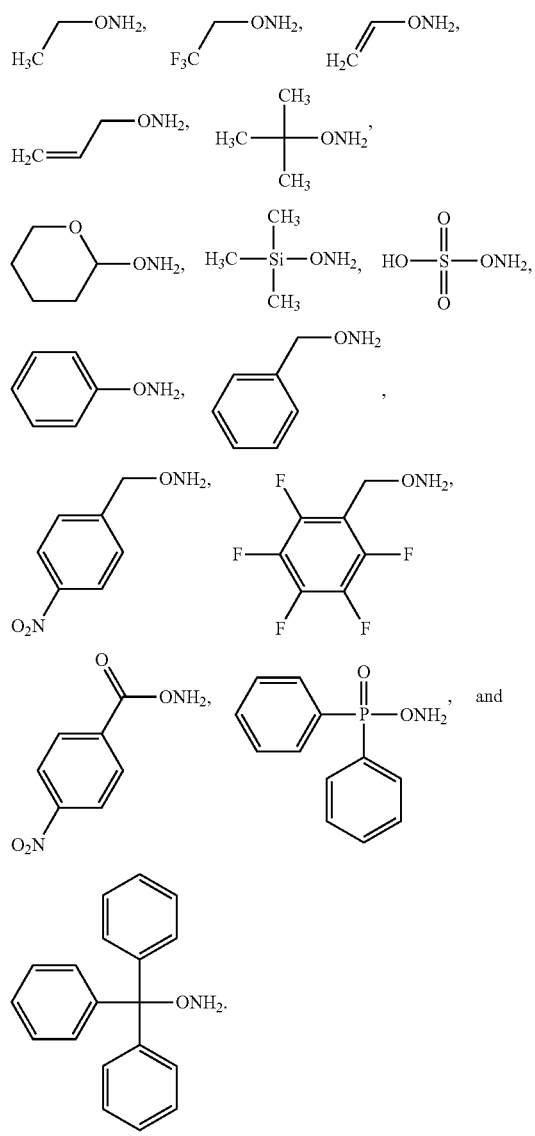

In embodiments, R2-block has a formula selected from the group consisting of:

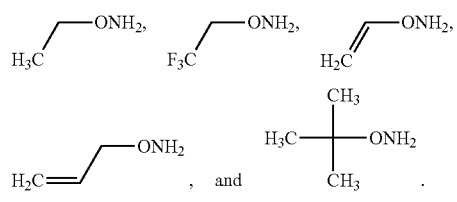

In embodiments R2-block has a formula

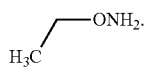

In embodiments, R2-block has a formula

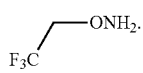

In embodiments, R2-block has a formula

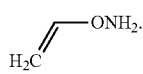

In embodiments, R2-block has a formula

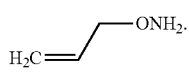

In embodiments, R2-block has a formula

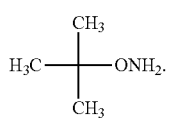

In embodiments, R2-block has a formula

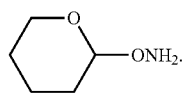

In embodiments, R2-block has a formula

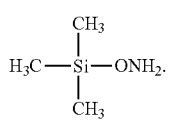

In embodiments, R2-block has a formula

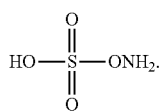

In embodiments, R2-block has a formula

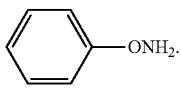

In embodiments, R2-block has a formula

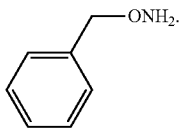

In embodiments, R2-block has a formula

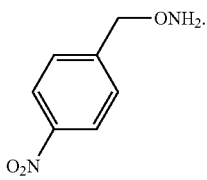

In embodiments, R2-block has a formula

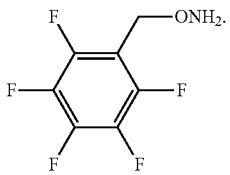

In embodiments, R2-block has a formula

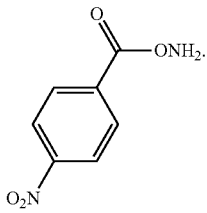

In embodiments, R2-block has a formula

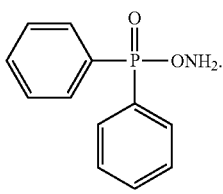

In embodiments, R2-block has a formula

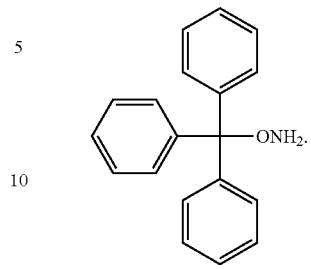

In embodiments, R2 comprises a hydroxylated moiety. In embodiments, R2 comprises at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety.

In embodiments, R2 has a molecular weight of no more than 280 g/mol. In embodiments, R2 has a molecular weight of no more than 100 g/mol.

In embodiments, the method adds a blocking group in place of a 3' protecting group to at least 94% of a population of nucleotides having a 3' protecting group in no more than 3 hours at 25° C. In embodiments, the method adds a blocking group in place of a 3' protecting group to at least 98% of a population of nucleotides having a 3' protecting group in no more than 3 hours at 25° C.

In embodiments, the method degrades no more than 6% of cytosine nucleobases in a population of nucleotides each comprising a cytosine nucleobase. In embodiments, the method degrades no more than 1% of cytosine bases from the population of nucleotides having a cytosine nucleobase.

In embodiments, the composition includes $(CH_3)_3C-ONH_2$. In embodiments, the solution includes $(CH_3)_3C-ONH_2$. In embodiments, the aqueous solution includes $(CH_3)_3C-ONH_2$. In embodiments, the vessel includes $(CH_3)_3C-ONH_2$. In embodiments, the kit includes $(CH_3)_3C-ONH_2$. In embodiments, the composition does not include $CH_3-ONH_2$. In embodiments, the solution does not include $CH_3-ONH_2$. In embodiments, the aqueous solution does not include $CH_3-ONH_2$. In embodiments, the vessel does not include $CH_3-ONH_2$. In embodiments, the kit does not include $CH_3-ONH_2$. In embodiments, the composition does not include $H-ONH_2$. In embodiments, the solution does not include $H-ONH_2$. In embodiments, the aqueous solution does not include $H-ONH_2$. In embodiments, the vessel does not include $H-ONH_2$. In embodiments, the kit does not include $H-ONH_2$.

EMBODIMENTS

Embodiment P1. A method for modifying a nucleotide, comprising reacting a nucleotide comprising a 3'-O-oxime moiety with a reagent comprising the structure R2-ONH$_2$ to produce a nucleotide comprising a 3'-O—NH$_2$ moiety, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment P2. The method of embodiment P1, wherein the nucleotide that comprises the 3'-O-oxime moiety comprises the structure:

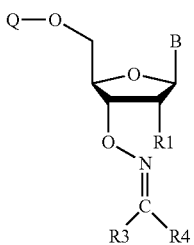

wherein the nucleotide that comprises the 3'-O—NH$_2$ moiety comprises the structure:

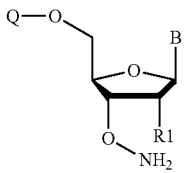

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment P3. The method of embodiment P1, wherein the reaction occurs in an aqueous solution.

Embodiment P4. The method of embodiment P3, wherein the nucleotide is attached to a solid support in contact with the aqueous solution.

Embodiment P5. The method of embodiment P3, wherein the reagent that comprises the structure R2-ONH$_2$ is attached to a solid support in contact with the aqueous solution.

Embodiment P6. The method of any one of embodiments P1 through P5, wherein the nucleobase is a purine or pyrimidine.

Embodiment P7. The method of embodiment P6, wherein the nucleobase is independently adenine, cytosine, guanine, thymine, or uracil.

Embodiment P8. The method of embodiment P6, wherein the nucleobase is complementary to adenine, cytosine, guanine, thymine, or uracil.

Embodiment P9. The method of embodiment P6, wherein the nucleobase is independently 5-methylcytosine, hypoxanthine, xanthine, inosine, isoguanine, isocytosine, or 7-deazaguanine.

Embodiment P10. The method of any one of embodiments P1 through P9, wherein the pH of the solution is between 4 and 8.

Embodiment P11. The method of any one of embodiments P1 through P10, wherein the nucleotide that is produced comprises a deoxynucleotide.

Embodiment P12. The method of embodiment P11, wherein the nucleotide that is produced comprises:

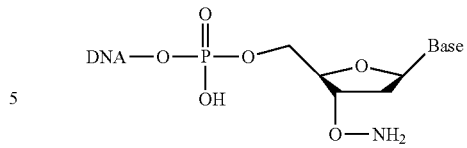

wherein Base is the nucleobase, and wherein DNA is independently a single stranded deoxyribonucleic acid or double stranded deoxyribonucleic acid.

Embodiment P13. The method of any one of embodiments P1 through P12, wherein the reagent is independently one of:

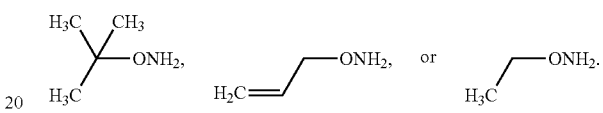

Embodiment P14. A solution comprising a nucleotide comprising a 3'-O-oxime moiety and a reagent comprising the structure R2-ONH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment P15. The solution of embodiment P14, wherein the nucleotide comprises the structure:

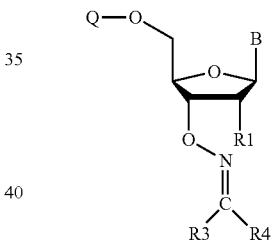

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment P16. The solution of embodiment P15, wherein R1 is H.

Embodiment P17. The solution of embodiment P16, wherein Q is deoxyribonucleic acid.

Embodiment P18. The solution of embodiment P15, wherein R1 is OH.

Embodiment P19. The solution of embodiment P18, wherein Q is ribonucleic acid.

Embodiment P20. The solution of embodiment P14, wherein the solution is an aqueous solution.

Embodiment P21. The solution of embodiment P20, wherein the nucleotide is attached to a solid support and wherein the solid support is in contact with the solution.

Embodiment P22. The solution of embodiment P20, wherein the reagent that comprises the structure R2-ONH$_2$ is attached to a solid support in contact with the aqueous solution.

Embodiment P23. The solution of any one of embodiments P14 through P2A3, wherein the nucleobase is a purine or pyrimidine.

Embodiment P24. The solution of embodiment P23, wherein the nucleobase is independently adenine, cytosine, guanine, thymine, or uracil.

Embodiment P25. The solution of embodiment P23, wherein the nucleobase is complementary to adenine, cytosine, guanine, thymine, or uracil.

Embodiment P26. The solution of embodiment P23, wherein the nucleobase is independently 5-methylcytosine, hypoxanthine, xanthine, inosine, isoguanine, isocytosine, or 7-deazaguanine.

Embodiment P27. The solution of any one of embodiments P14 through P26, wherein the nucleobase comprises an exogenous label moiety.

Embodiment P28. The solution of any one of embodiments P14 through P27, wherein the pH of the solution is between 4 and 8.

Embodiment P29. The solution of any one of embodiments P14 through P28, wherein the R2-ONH$_2$ molecule is independently one of:

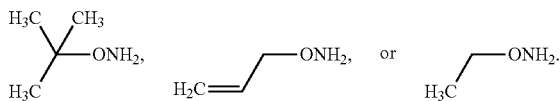

Embodiment P30. A kit comprising a first vessel containing a nucleotide comprising a 3'-O-oxime moiety and a second vessel containing a reagent comprising the structure R2-ONH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment P31. The kit of embodiment P30, wherein the nucleotide comprises the structure:

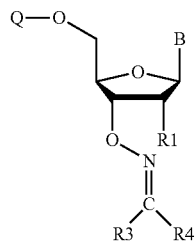

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment P32. The kit of embodiment P30, wherein the kit comprises an RFID tag or bar code.

Embodiment P33. The kit of embodiment P31 or P32, wherein Q is independently a single stranded deoxyribonucleic acid or double stranded deoxyribonucleic acid.

Embodiment P34. The kit of embodiment P33, wherein the nucleotide is attached to a solid support.

Embodiment P35. The kit of embodiment P30, wherein the reagent that comprises the structure R2-ONH$_2$ is attached to a solid support.

Embodiment P36. The kit of any one of embodiments P30 through P35, wherein the nucleobase is a purine or pyrimidine.

Embodiment P38. The kit of embodiment P36, wherein the nucleobase is independently adenine, cytosine, guanine, thymine, or uracil.

Embodiment P39. The kit of embodiment P36, wherein the nucleobase is complementary to adenine, cytosine, guanine, thymine, or uracil.

Embodiment P40. The kit of embodiment P36, wherein the nucleobase is independently 5-methylcytosine, hypoxanthine, xanthine, inosine, isoguanine, isocytosine, or 7-deazaguanine.

Embodiment P41. The kit of any one of embodiments P30 through P40, wherein the nucleobase comprises an exogenous label moiety.

Embodiment P42. The kit of any one of embodiments P30 through P41, wherein the R2-ONH$_2$ molecule is independently one of:

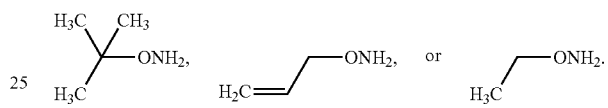

Embodiment PP1. A method for modifying a nucleotide, comprising reacting a nucleotide comprising a 3'-O-oxime moiety with a reagent comprising the structure R2-ONH$_2$ to produce a nucleotide comprising a 3'-O—NH$_2$ moiety, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment PP2. The method of embodiment PP1, wherein the nucleotide that comprises the 3'-O-oxime moiety comprises the structure:

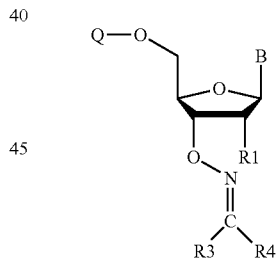

wherein the nucleotide that comprises the 3'-O—NH$_2$ moiety comprises the structure:

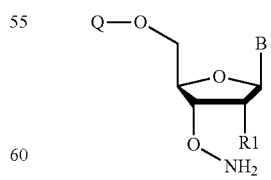

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment PP3. The method of embodiment PP1, wherein the reaction occurs in an aqueous solution.

Embodiment PP4. The method of embodiment PP3, wherein the nucleotide is attached to a solid support in contact with the aqueous solution.

Embodiment PP5. The method of embodiment PP3, wherein the reagent that comprises the structure R2-ONH$_2$ is attached to a solid support in contact with the aqueous solution.

Embodiment PP6. The method of any one of embodiments PP1 through PP5, wherein the nucleobase is a purine or pyrimidine.

Embodiment PP7. The method of embodiment PP6, wherein the nucleobase is independently adenine, cytosine, guanine, thymine, or uracil.

Embodiment PP8. The method of embodiment PP6, wherein the nucleobase is complementary to adenine, cytosine, guanine, thymine, or uracil.

Embodiment PP9. The method of embodiment PP6, wherein the nucleobase is independently 5-methylcytosine, hypoxanthine, xanthine, inosine, isoguanine, isocytosine, or 7-deazaguanine.

Embodiment PP10. The method of any one of embodiments PP1 through PP9, wherein the pH of the solution is between 4 and 8.

Embodiment PP11. The method of any one of embodiments PP1 through PP10, wherein the nucleotide that is produced comprises a deoxynucleotide.

Embodiment PP12. The method of embodiment PP 11, wherein the nucleotide that is produced comprises:

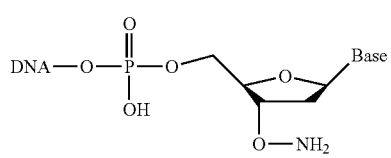

wherein Base is the nucleobase, and wherein DNA is independently a single stranded deoxyribonucleic acid or double stranded deoxyribonucleic acid.

Embodiment PP13. The method of any one of embodiments PP1 through PP12, wherein the reagent is independently one of:

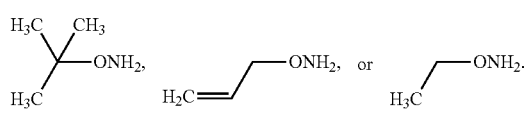

Embodiment PP14. A solution comprising a nucleotide comprising a 3'-O-oxime moiety and a reagent comprising the structure R2-ONH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment PP15. The solution of embodiment PP14, wherein the nucleotide comprises the structure:

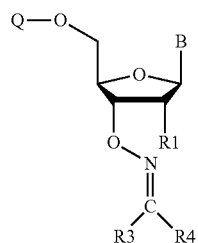

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment PP16. The solution of embodiment PP15, wherein R1 is H.

Embodiment PP17. The solution of embodiment PP16, wherein Q is deoxyribonucleic acid.

Embodiment PP18. The solution of embodiment PP15, wherein R1 is OH.

Embodiment PP19. The solution of embodiment PP18, wherein Q is ribonucleic acid.

Embodiment PP20. The solution of embodiment PP14, wherein the solution is an aqueous solution.

Embodiment PP21. The solution of embodiment PP20, wherein the nucleotide is attached to a solid support and wherein the solid support is in contact with the solution.

Embodiment PP22. The solution of embodiment PP20, wherein the reagent that comprises the structure R2-ONH$_2$ is attached to a solid support in contact with the aqueous solution.

Embodiment PP23. The solution of any one of embodiments PP14 through PP22, wherein the nucleobase is a purine or pyrimidine.

Embodiment PP24. The solution of embodiment PP23, wherein the nucleobase is independently adenine, cytosine, guanine, thymine, or uracil.

Embodiment PP25. The solution of embodiment PP23, wherein the nucleobase is complementary to adenine, cytosine, guanine, thymine, or uracil.

Embodiment PP26. The solution of embodiment PP23, wherein the nucleobase is independently 5-methylcytosine, hypoxanthine, xanthine, inosine, isoguanine, isocytosine, or 7-deazaguanine.

Embodiment PP27. The solution of any one of embodiments PP14 through PP26, wherein the nucleobase comprises an exogenous label moiety.

Embodiment PP28. The solution of any one of embodiments PP14 through PP27, wherein the pH of the solution is between 4 and 8.

Embodiment PP29. The solution of any one of embodiments PP14 through PP28, wherein the R2-ONH$_2$ molecule is independently one of:

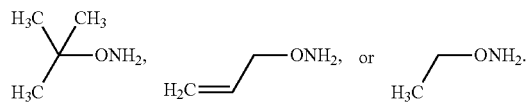

Embodiment PP30. A kit comprising a first vessel containing a nucleotide comprising a 3'-O-oxime moiety and a second vessel containing a reagent comprising the structure R2-ONH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment PP31. The kit of embodiment PP30, wherein the nucleotide comprises the structure:

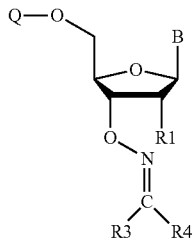

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment PP32. The kit of embodiment PP30, wherein the kit comprises an RFID tag or bar code.

Embodiment PP33. The kit of embodiment PP31 or PP32, wherein Q is independently a single stranded deoxyribonucleic acid or double stranded deoxyribonucleic acid.

Embodiment PP34. The kit of embodiment PP33, wherein the nucleotide is attached to a solid support.

Embodiment PP35. The kit of embodiment PP30, wherein the reagent that comprises the structure R2-ONH$_2$ is attached to a solid support.

Embodiment PP36. The kit of any one of embodiments PP30 through PP35, wherein the nucleobase is a purine or pyrimidine.

Embodiment PP38. The kit of embodiment PP36, wherein the nucleobase is independently adenine, cytosine, guanine, thymine, or uracil.

Embodiment PP39. The kit of embodiment PP36, wherein the nucleobase is complementary to adenine, cytosine, guanine, thymine, or uracil.

Embodiment PP40. The kit of embodiment PP36, wherein the nucleobase is independently 5-methylcytosine, hypoxanthine, xanthine, inosine, isoguanine, isocytosine, or 7-deazaguanine.

Embodiment PP41. The kit of any one of embodiments PP30 through PP40, wherein the nucleobase comprises an exogenous label moiety.

Embodiment PP42. The kit of any one of embodiments PP30 through PP41, wherein the R2-ONH$_2$ molecule is independently one of:

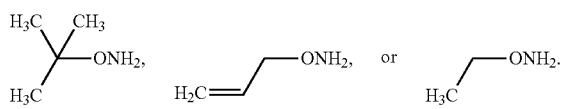

Further Embodiments

Embodiment S1. A method of adding a 3'-O—NH$_2$ moiety to a nucleotide having a 3' protecting group, comprising contacting a nucleotide having a 3' protecting group to a reagent comprising the structure R2-O—NH$_2$, wherein R2 has a molecular weight of at least 24.

Embodiment S2. The method of embodiment S1, wherein the nucleotide having a 3' protecting group comprises ribose or deoxyribose.

Embodiment S3. The method of embodiment S2, wherein the nucleotide having a 3' protecting group comprises triphosphate.

Embodiment S4. The method of embodiment S1, wherein the nucleotide having a 3' protecting group comprises the structure:

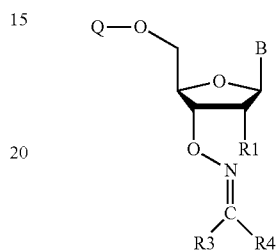

wherein the nucleotide that comprises the 3'-O—NH$_2$ moiety comprises the structure:

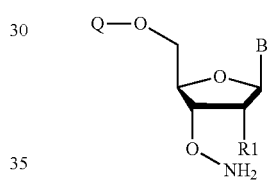

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment S5. A method of making a 3'-blocked nucleotide, the method comprising contacting a 3'-protected nucleotide with a reagent having the structure R2-O—NH$_2$, R2-O—NHCH$_3$, R2-O—NHCOCH$_3$, or R2O—CH$_2$N$_3$ wherein R2 has a molecular weight of at least 24 g/mol and thereby making a 3'-blocked nucleotide from a 3'-protected nucleotide.

Embodiment S6. A method of making a 3'-blocked nucleotide, the method comprising contacting a 3'-protected nucleotide with a reagent having the structure R2-O—NH$_2$ or R2O—CH$_2$N$_3$ wherein R2 has a molecular weight of at least 24 g/mol and thereby making a 3'-blocked nucleotide from a 3'-protected nucleotide.

Embodiment S7. The method of embodiment S5, wherein the 3'-blocked nucleotide comprises a blocking moiety bonded directly to the ribose 3' carbon of the nucleotide; and the blocking moiety is —ONH$_2$, —ONHCOCH$_3$, —ONHCH$_3$, —OCH$_2$N$_3$.

Embodiment S8. The method of one of embodiments S5 to S6, wherein the 3'-blocked nucleotide comprises a blocking moiety bonded directly to the ribose 3' carbon of the nucleotide; and the blocking moiety is —ONH$_2$ or —OCH$_2$N$_3$.

Embodiment S9. The method of one of embodiments S5 to S6, wherein the 3'-blocked nucleotide comprises a blocking moiety bonded directly to the ribose 3' carbon of the nucleotide; and the blocking moiety is —ONH$_2$.

Embodiment S10. The method of one of embodiments S5 to S9, wherein the 3'-protected nucleotide comprises a protecting moiety directly covalently bonded to the ribose 3' carbon of the nucleotide; and the protecting moiety is a 3'-O-oxime moiety.

Embodiment S11. The method of embodiment S10, wherein the —O-oxime moiety has the formula:

—O—N=C(R3)(R4); and

R3 and R4 are independently hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S12. The method of embodiment S10, wherein the —O-oxime moiety has the formula:

—O—N=C(R3)(R4);

R3 is hydrogen; and
R4 is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S13. The method of embodiment S10, wherein the —O-oxime moiety has the formula:

—O—N=C(R3)(R4); and

R3 and R4 are independently substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S14. The method of one of embodiments S5 to S13, wherein the 3'-blocked nucleotide and the 3'-protected nucleotide comprise an adenine moiety or derivative thereof, guanine moiety or derivative thereof, cytosine moiety or derivative thereof, thymine moiety or derivative thereof, or uracil moiety or derivative thereof.

Embodiment S15. The method of embodiment S14, wherein the adenine derivative moiety, guanine derivative moiety, cytosine derivative moiety, thymine derivative moiety, and uracil derivative moiety comprise a detectable moiety.

Embodiment S16. The method of one of embodiments S5 to S15, wherein the 3'-blocked nucleotide and the 3'-protected nucleotide comprise a monophosphate moiety or derivative thereof, diphosphate moiety or derivative thereof, triphosphate moiety or derivative thereof, or monovalent nucleic acid moiety or derivative thereof.

Embodiment S17. The method of embodiment S16, wherein the 3'-blocked nucleotide and the 3'-protected nucleotide comprise a monophosphate moiety, diphosphate moiety, triphosphate moiety, or monovalent nucleic acid moiety.

Embodiment S18. The method of embodiment S16, wherein the 3'-blocked nucleotide and the 3'-protected nucleotide comprise a triphosphate moiety.

Embodiment S19. The method of embodiment S16, wherein the 3'-blocked nucleotide and the 3'-protected nucleotide comprise a monovalent nucleic acid moiety.

Embodiment S20. The method of one of embodiments S5 to S19, wherein the 3'-blocked nucleotide and the 3'-protected nucleotide comprise a ribose moiety.

Embodiment S21. The method of one of embodiments S5 to S19, wherein the 3'-blocked nucleotide and the 3'-protected nucleotide comprise a 2' deoxyribose moiety.

Embodiment S22. The method of one of embodiments Si to S21, wherein R2 has a molecular weight of 1000 g/mol or less.

Embodiment S23. The method of one of embodiments Si to S22, wherein R2 has a molecular weight of at least 36 g/mol.

Embodiment S24. The method of one of embodiments Si to S22, wherein R2 has a molecular weight of at least 57 g/mol.

Embodiment S25. The method of one of embodiments Si to S22, wherein R2 comprises at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety.

Embodiment S26. The method of one of embodiments S1 to S22, wherein R2 is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S27. The method of one of embodiments Si to S22, wherein
R2 is —C(R6)(R7)(R8), —C(O)(R6), —P(O)(R6)(R7), —C(R6)(=C(R7)(R8)), —Si(R6)(R7)(R8), —SO$_2$(R6), substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl; and
R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S28. The method of embodiment S27, wherein R2 is —C(R6)(R7)(R8) and R6, R7, and R8 are not all hydrogen.

Embodiment S29. The method of embodiment S27, wherein R2 is not unsubstituted methyl.

Embodiment S30. The method of embodiment S27, wherein R2 is not unsubstituted ethyl.

Embodiment S31. The method of embodiment S27, wherein R2 is not unsubstituted propyl.

Embodiment S32. The method of one of embodiments Si to S22, wherein
R2 is —C(R6)(R7)(R8), —C(O)(R6), —P(O)(R6)(R7), —C(R6)(=C(R7)(R8)), —Si(R6)(R7)(R8), —SO$_2$(R6), unsubstituted 6 membered heteroalicyclyl, unsubstituted phenyl, substituted or unsubstituted heteroaryl; and
R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S33. The method of embodiment S32, wherein R2 is —C(R6)(R7)(R8) and R6, R7, and R8 are not all hydrogen.

Embodiment S34. The method of embodiment S32, wherein R2 is not unsubstituted methyl.

Embodiment S35. The method of embodiment S32, wherein R2 is not unsubstituted ethyl.

Embodiment S36. The method of embodiment S32, wherein R2 is not unsubstituted propyl.

Embodiment S37. The method of one of embodiments S1 to S22, wherein the reagent has the formula:

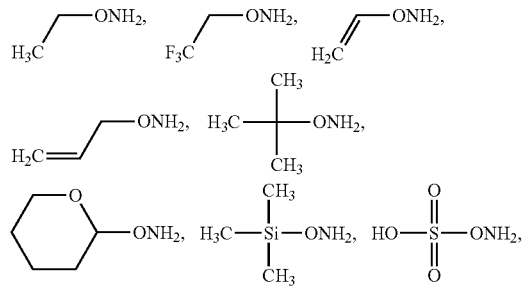

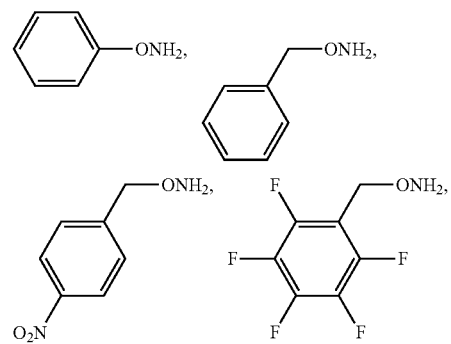

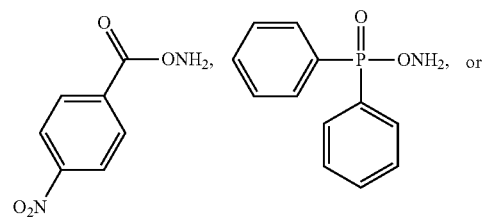

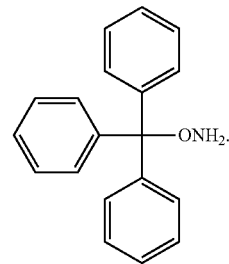

Embodiment S38. The method of one of embodiments S1 to S22, wherein the reagent has the formula:

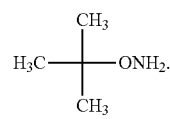

Embodiment S39. The method of one of embodiments S5 to S11, wherein the 3'-protected nucleotide has the structure:

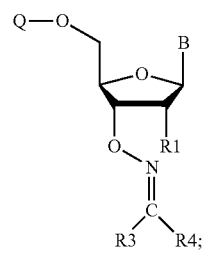

the 3'-blocked nucleotide has the structure:

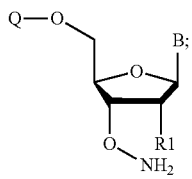

B is a nucleobase;
R1 is hydrogen, —OH, halogen, —OCH$_3$;
Q is independently a nucleic acid moiety, triphosphate moiety, diphosphate moiety, or monophosphate moiety;
R3 and R4 are independently hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S40. The method of one of embodiments Si to S4, wherein the method adds a 3' ONH$_2$ in place of a 3' protecting group to at least 94% of a population of nucleotides having a 3' protecting group in no more than 3 hours.

Embodiment S41. The method of one of embodiments Si to S4, wherein the method adds a 3' ONH$_2$ in place of a 3' protecting group to at least 98% of a population of nucleotides having a 3' protecting group in no more than 1 hour.

Embodiment S42. The method of one of embodiments Si to S4, wherein the nucleotide having a 3' protecting group comprises cytosine, and wherein method degrades no more than 6% of cytosine bases from a population comprising a plurality of said nucleotide having a 3' protecting group comprising cytosine.

Embodiment S43. The method of one of embodiments Si to S4, wherein the nucleotide having a 3' protecting group comprises cytosine, and wherein method degrades no more than 1% of cytosine bases from a population comprising a plurality of said nucleotide having a 3' protecting group comprising cytosine.

Embodiment S44. The method of one of embodiments S5 to S39, further comprising making a first plurality of 3'-blocked nucleotides, the method comprising contacting a second plurality of 3'-protected nucleotides with a third plurality of the reagent and thereby making a first plurality of 3'-blocked nucleotides from a second plurality of 3'-protected nucleotides.

Embodiment S45. The method of embodiment S44, wherein the first plurality of 3'-blocked nucleotides are made for 3 hours or less.

Embodiment S46. The method of embodiment S44, wherein the first plurality of 3'-blocked nucleotides are made for 2 hours or less.

Embodiment S47. The method of embodiment S44, wherein the first plurality of 3'-blocked nucleotides are made for 1 hour or less.

Embodiment S48. The method of one of embodiments S44 to S47, wherein at least 94% of the first plurality of 3'-protected nucleotide is made into the second plurality of 3'-blocked nucleotides.

Embodiment S49. The method of one of embodiments S44 to S47, wherein at least 96% of the first plurality of 3'-protected nucleotide is made into the second plurality of 3'-blocked nucleotides.

Embodiment S50. The method of one of embodiments S44 to S47, wherein at least 98% of the first plurality of 3'-protected nucleotide is made into the second plurality of 3'-blocked nucleotides.

Embodiment S51. The method of one of embodiments S44 to S50, wherein the first plurality of 3'-blocked nucleotides comprises a fourth plurality of 3'-blocked nucleotides comprising a cytosine; and 6% or less of the cytosines are chemically modified by the third plurality of the reagent.

Embodiment S52. The method of one of embodiments S44 to S50, wherein the first plurality of 3'-blocked nucleotides comprises a fourth plurality of 3'-blocked nucleotides comprising a cytosine; and 5% or less of the cytosines are chemically modified by the third plurality of the reagent.

Embodiment S53. The method of one of embodiments S44 to S50, wherein the first plurality of 3'-blocked nucleotides comprises a fourth plurality of 3'-blocked nucleotides comprising a cytosine; and 4% or less of the cytosines are chemically modified by the third plurality of the reagent.

Embodiment S54. The method of one of embodiments S44 to S50, wherein the first plurality of 3'-blocked nucleotides comprises a fourth plurality of 3'-blocked nucleotides comprising a cytosine; and 3% or less of the cytosines are chemically modified by the third plurality of the reagent.

Embodiment S55. The method of one of embodiments S44 to S50, wherein the first plurality of 3'-blocked nucleotides comprises a fourth plurality of 3'-blocked nucleotides comprising a cytosine; and 2% or less of the cytosines are chemically modified by the third plurality of the reagent.

Embodiment S56. The method of one of embodiments S44 to S50, wherein the first plurality of 3'-blocked nucleotides comprises a fourth plurality of 3'-blocked nucleotides comprising a cytosine; and 1% or less of the cytosines are chemically modified by the third plurality of the reagent.

Embodiment S57. A composition comprising a population of cytosine nucleotides wherein at least 94% of the population of cytosine nucleotides comprise a 3'-O—NH$_2$, wherein no more than 8% of the population of cytosine nucleotides comprise a 3' moiety other than —O—NH$_2$, and wherein no more than 6% of the population of cytosine nucleotides comprise a modified cytosine base.

Embodiment S58. The composition of embodiment S57, wherein at least 98% of the population of cytosine nucleotides comprise a 3'-O—NH$_2$, wherein no more than 1% of the population of cytosine nucleotides comprise a 3' moiety other than —O—NH$_2$, and wherein no more than 1% of the population of cytosine nucleotides comprise a modified cytosine base.

Embodiment S59. The composition of embodiment S57, wherein the composition is an aqueous solution.

Embodiment S60. The composition of embodiment S57, wherein the pH of the solution is no less than 4 and no greater than 8.

Embodiment S61. The composition of embodiment S57, wherein the composition comprises a reagent comprising the structure R2-O—NH$_2$.

Embodiment S62. The composition of embodiment S61, wherein R2 comprises a molecular weight of at least 24, 26, 57, or 100.

Embodiment S63. The composition of embodiment S61, wherein R2 comprises at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety.

Embodiment S64. The composition of embodiment S61, wherein the reagent comprising the structure R2-O—NH₂ is selected from the group consisting of:

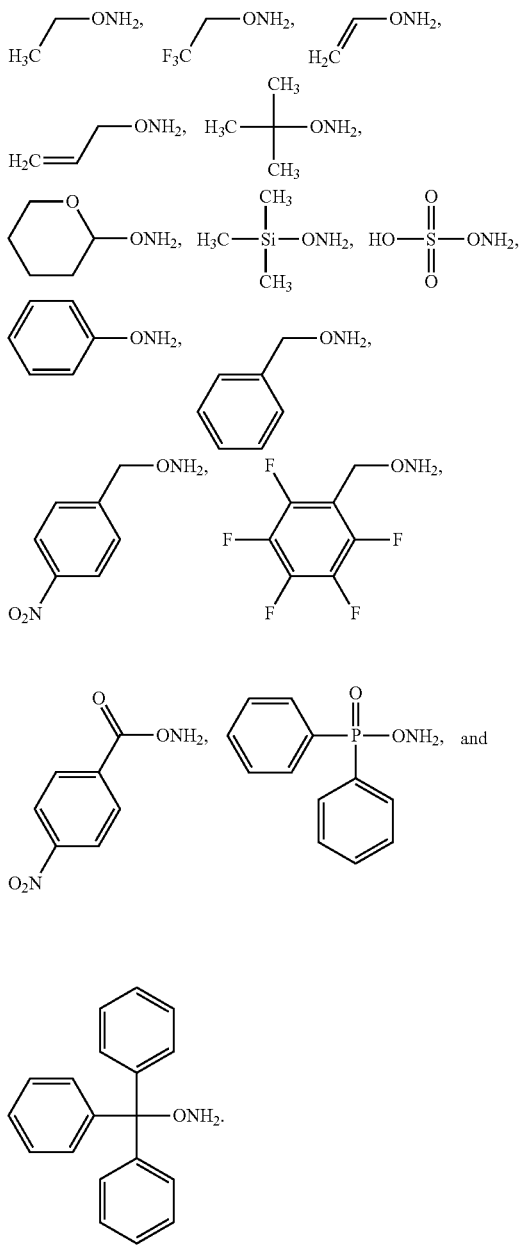

Embodiment S65. The composition of one of embodiments S57 to S64, wherein the 3' moiety other than —O—NH₂ comprises a 3' O-oxime.

Embodiment S66. The composition of embodiment S57, wherein the composition comprises a reagent comprising the structure R2-O—NHCH₃ or R2-O—CH₂N₃.

Embodiment S67. The composition of one of embodiments S57 to S66, wherein at least some of the cytosine nucleotides having a 3' moiety other than —O—NH₂ nucleotide comprise the structure:

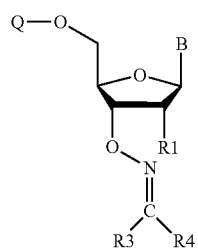

wherein B is a cytosine nucleobase; R1 is independently halogen, OCH₃, H or OH, Q is independently monophosphate, diphosphate, triphosphate, or nucleic acid, and R3 and R4 are independently H, CH₃, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment S68. A method of formulating a sequencing reagent, comprising contacting a composition comprising a 3' protected nucleotide to a reagent comprising a reversible terminator moiety to produce a composition comprising a nucleotide comprising a reversible terminator moiety, and formulating the composition comprising a nucleotide comprising a reversible terminator moiety as a sequencing reagent, wherein formulating the composition comprising a reversible terminator moiety does not comprise further purification of the composition comprising a reversible terminator moiety.

Embodiment S69. The method of embodiment S68, further comprising applying the sequencing reagent to a sequencing reagent to yield a sequencing run of at least 100 bases having a quality score of at least Q30.

Embodiment S70. The method of embodiment S68, wherein the reagent comprising a reversible terminator moiety has a structure R2-O—NH₂.

Embodiment S71. The method of embodiment S70, wherein R2 is selected from the group consisting of —C(R6)(R7)(R8), —C(O)(R6), —P(O)(R6)(R7), —C(R6)(=C(R7)(R8)), —Si(R6)(R7)(R8), —SO₂(R6), substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl; and R6, R7, and R8 are independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OC₃, —OCHCl₂, —OCHBr₂, —OCHI₂, —OCHF₂, —OCH₂Cl, —OCH₂Br, —OCH₂I, —OCH₂F, —SF₅, —N₃, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S72. The method of embodiment S71, wherein R2 is —C(R6)(R7)(R8) and R6, R7, and R8 are not all hydrogen.

Embodiment S73. The method of embodiment S71, wherein R2 is not unsubstituted methyl.

Embodiment S74. The method of embodiment S71, wherein R2 is not unsubstituted ethyl.

Embodiment S75. The method of embodiment S71, wherein R2 is not unsubstituted propyl.

Embodiment S76. The method of embodiment S70, wherein R2 is —C(CH$_3$)$_3$.

Embodiment S77. The method of embodiment S70, wherein R2 has a molecular weight greater than 24, 36, 57, or 100.

Embodiment S78. The method of embodiment S70, wherein R2 comprises at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety.

Embodiment S79. The method of embodiment S68, wherein the 3' protected nucleotide comprises a 3'-O-oxime moiety.

Embodiment S80. The method of embodiment S68, wherein the composition comprising a nucleotide comprising a reversible terminator moiety comprises no more than 6% of the 3' protected nucleotide relative to 3' protected nucleotide present initially.

Embodiment S81. The method of embodiment S68, wherein the composition comprising a nucleotide comprising a reversible terminator moiety comprises degraded or modified dC nucleobases at a concentration of no more than 6% of total dC nucleobases in the composition comprising a nucleotide comprising a reversible terminator moiety.

Embodiment S82. A method for modifying a nucleotide, comprising reacting a nucleotide comprising a 3'-O-oxime moiety with a reagent comprising the structure R2-O—NH$_2$ to produce a nucleotide comprising a 3'-O—NH$_2$ moiety, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment S83. The method of embodiment S82, wherein the nucleotide that comprises the 3'-O-oxime moiety comprises the structure:

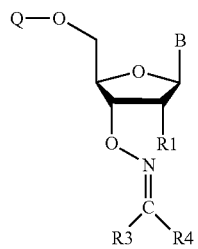

wherein the nucleotide that comprises the 3'-O—NH$_2$ moiety comprises the structure:

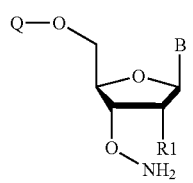

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment S84. The method of one of embodiments S82 to S83, wherein the nucleotide that is produced comprises a deoxynucleotide.

Embodiment S85. The method of embodiment S82, wherein the nucleotide that is produced comprises:

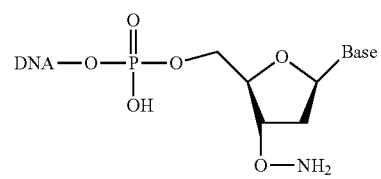

wherein Base is the nucleobase, and wherein DNA is independently a single stranded deoxyribonucleic acid or double stranded deoxyribonucleic acid.

Embodiment S86. The method of any one of embodiments S82 to S85, wherein the reagent is independently one of:

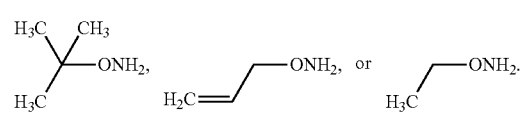

Embodiment S87. A solution comprising a nucleotide comprising a 3'-O-oxime moiety and a reagent comprising the structure R2-O—NH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment S88. The solution of embodiment S87, wherein the nucleotide comprises the structure:

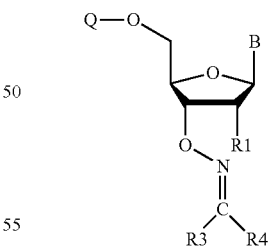

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment S89. The solution of one of embodiments S87 to S88, wherein the nucleobase comprises an exogenous label moiety.

Embodiment S90. The solution of one of embodiments S87 to S89, wherein the R2-O—NH$_2$ molecule is independently one of:

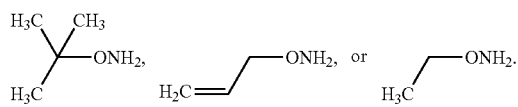

Embodiment S91. A method of sequencing a nucleic acid comprising the steps:
  A. making a 3'-blocked nucleotide using the method of one of embodiments S5 to S56, wherein the method of making does not comprise isolating the 3'-blocked nucleotide from the composition comprising the reactants and products of contacting the 3'-protected nucleotide with the reagent;
  B. contacting the composition comprising the 3'-blocked nucleotide of step A with a nucleic acid template, primer, and polymerase in a reaction vessel;
  C. identifying the 3'-blocked nucleotide that simultaneously contacts the template nucleic acid, 3' terminus of the primer, and polymerase; and optionally covalently binding the 3'-blocked nucleotide to the 3' terminus of the primer, making an extended primer; and thereby identifying the cognate nucleotide of the template nucleic acid to the 3'-blocking nucleotide;
  D. removing the 3'-blocking moiety from the 3'-blocked nucleotide of the extended primer of step C; and
  E. repeating steps B to D and thereby sequencing the template nucleic acid.

Embodiment S92. The method of embodiment S91, wherein step E is executed at least 99 times.

Embodiment S93. The method of one of embodiments S91 to S92, wherein the quality score of the sequencing is at least Q20.

Embodiment S94. The method of one of embodiments S91 to S92, wherein the quality score of the sequencing is at least Q30.

Embodiment S95 The method of one of embodiments S91 to S92, wherein the quality score of the sequencing is at least Q50.

Embodiment S96. A kit comprising a first vessel containing a 3'-blocked nucleotide and a second vessel containing a reagent having the formula R2-O—NH$_2$, R2-O—NHCH$_3$, or R2O—CH$_2$N$_3$ wherein R2 has a molecular weight of at least 24 g/mol.

Embodiment S97. The kit of embodiment S96, wherein the 3'-blocked nucleotide comprises a blocking moiety bonded directly to the ribose 3' carbon of the nucleotide; and the blocking moiety is —ONH$_2$, —ONHCH$_3$, or —OCH$_2$CH$_3$.

Embodiment S98. The kit of embodiment S96, wherein the 3'-blocked nucleotide comprises a blocking moiety bonded directly to the ribose 3' carbon of the nucleotide; and the blocking moiety is —ONH$_2$.

Embodiment S99. The kit of one of embodiments S96 to S98, wherein the 3'-protected nucleotide comprises a protecting moiety directly covalently bonded to the ribose 3' carbon of the nucleotide; and the protecting moiety is a 3' oxime moiety.

Embodiment S100. The kit of embodiment S99, wherein the —O-oxime moiety has the formula:

—O—N=C(R3)(R4); and

R3 and R4 are independently hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S101. The kit of embodiment S99, wherein the —O-oxime moiety has the formula:

—O—N=C(R3)(R4);

R3 is hydrogen; and
R4 is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S102. The kit of embodiment S99, wherein the —O-oxime moiety has the formula:

—O—N=C(R3)(R4); and

R3 and R4 are independently substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S103. The kit of one of embodiments S96 to S102, wherein the 3'-blocked nucleotide and the 3'-protected nucleotide comprise an adenine moiety or derivative thereof, guanine moiety or derivative thereof, cytosine moiety or derivative thereof, thymine moiety or derivative thereof, or uracil moiety or derivative thereof.

Embodiment S104. The kit of embodiment S103, wherein the adenine derivative moiety, guanine derivative moiety, cytosine derivative moiety, thymine derivative moiety, and uracil derivative moiety comprise a detectable moiety.

Embodiment S105. The kit of one of embodiments S96 to S104, wherein the 3'-blocked nucleotide and the 3'-protected nucleotide comprise a monophosphate moiety or derivative thereof, diphosphate moiety or derivative thereof, triphosphate moiety or derivative thereof, or monovalent nucleic acid moiety or derivative thereof.

Embodiment S106. The kit of embodiment S105, wherein the 3'-blocked nucleotide and the 3'-protected nucleotide comprise a monophosphate moiety, diphosphate moiety, triphosphate moiety, or monovalent nucleic acid moiety.

Embodiment S107. The kit of embodiment S105, wherein the 3'-blocked nucleotide and the 3'-protected nucleotide comprise a triphosphate moiety.

Embodiment S108. The kit of embodiment S105, wherein the 3'-blocked nucleotide and the 3'-protected nucleotide comprise a monovalent nucleic acid moiety.

Embodiment S109. The kit of one of embodiments S96 to S108, wherein the 3'-blocked nucleotide and the 3'-protected nucleotide comprise a ribose moiety.

Embodiment S110. The kit of one of embodiments S96 to S108, wherein the 3'-blocked nucleotide and the 3'-protected nucleotide comprise a 2' deoxyribose moiety.

Embodiment S111. The kit of one of embodiments S96 to S110, wherein R2 has a molecular weight of 1000 g/mol or less.

Embodiment S112. The kit of one of embodiments S96 to S111, wherein R2 has a molecular weight of at least 36 g/mol.

Embodiment S113. The kit of one of embodiments S96 to S111, wherein R2 has a molecular weight of at least 57 g/mol.

Embodiment S114. The kit of one of embodiments S96 to S111, wherein R2 is substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S115. The kit of one of embodiments S96 to S111, wherein R2 is —C(R6)(R7)(R8), —C(O)(R6), —P(O)(R6)(R7), —C(R6)(=C(R7)(R8)), —Si(R6)(R7)(R8), —SO$_2$(R6), substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl; and R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S116. The kit of embodiment S115, wherein R2 is —C(R6)(R7)(R8) and R6, R7, and R8 are not all hydrogen.

Embodiment S117. The kit of embodiment S115, wherein R2 is not unsubstituted methyl.

Embodiment S118. The kit of embodiment S115, wherein R2 is not unsubstituted ethyl.

Embodiment S119. The kit of embodiment S115, wherein R2 is not unsubstituted propyl.

Embodiment S120. The kit of one of embodiments S96 to S111, wherein R2 is —C(R6)(R7)(R8), —C(O)(R6), —P(O)(R6)(R7), —C(R6)(=C(R7)(R8)), —Si(R6)(R7)(R8), —SO$_2$(R6), unsubstituted 6 membered heteroalicyclyl, unsubstituted phenyl, substituted or unsubstituted heteroaryl; and R6, R7, and R8 are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —SF$_5$, —N$_3$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S121. The kit of embodiment S120, wherein R2 is —C(R6)(R7)(R8) and R6, R7, and R8 are not all hydrogen.

Embodiment S122. The kit of embodiment S120, wherein R2 is not unsubstituted methyl.

Embodiment S123. The kit of embodiment S120, wherein R2 is not unsubstituted ethyl.

Embodiment S124. The kit of embodiment S120, wherein R2 is not unsubstituted propyl.

Embodiment S125. The kit of one of embodiments S96 to S111, wherein the reagent has the formula:

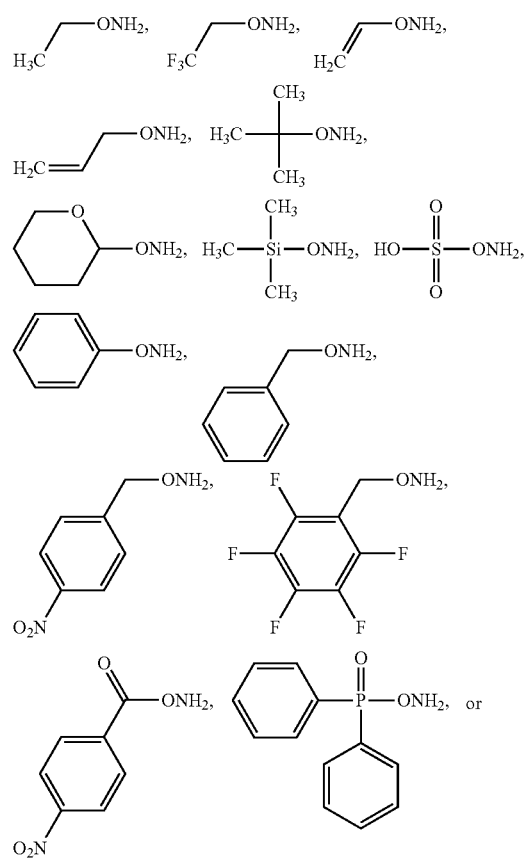

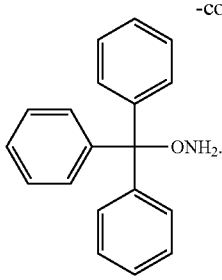

Embodiment S126. The kit of one of embodiments S96 to S111, wherein the reagent has the formula:

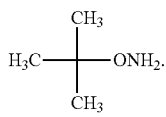

Embodiment S127. The kit of one of embodiments S96 to S100, wherein the 3'-protected nucleotide has the structure:

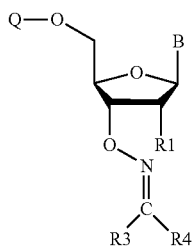

the 3'-blocked nucleotide has the structure:

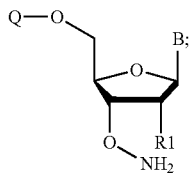

B is a nucleobase;
R1 is hydrogen, —OH, halogen, —OCH₃;
Q is independently a nucleic acid moiety, triphosphate moiety, diphosphate moiety, or monophosphate moiety; and R3 and R4 are independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment S128. A kit comprising a first vessel containing a nucleotide comprising a 3'-O-oxime moiety and a second vessel containing a reagent comprising the structure R2-O—NH₂, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment S129. The kit of embodiment S128, wherein the nucleotide comprises the structure:

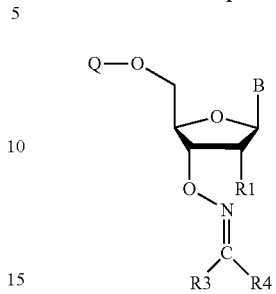

wherein B is a nucleobase; R1 is independently halogen, OCH₃, H or OH, Q is independently monophosphate, diphosphate, triphosphate, or nucleic acid, and R3 and R4 are independently H, CH₃, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment S130. The kit of one of embodiments S128 to S129, wherein the nucleobase comprises an exogenous label moiety.

Embodiment S131. The kit of one of embodiments S128 to S130, wherein the R2-O—NH₂ molecule is independently one of:

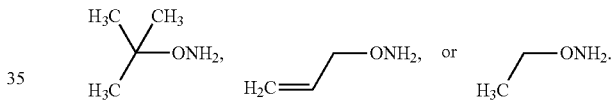

Embodiment T1. A method of adding a 3'-O—NH₂ moiety to a nucleotide having a 3' protecting group, comprising contacting a nucleotide having a 3' protecting group to a reagent comprising the structure R2-O—NH₂, wherein R2 has a molecular weight of at least 24.

Embodiment T2. The method of embodiment T1, wherein the nucleotide having a 3' protecting group comprises ribose.

Embodiment T3. The method of embodiment T1, wherein the nucleotide having a 3' protecting group comprises 2' deoxyribose.

Embodiment T4. The method of embodiment T2, wherein the nucleotide having a 3' protecting group comprises phosphate.

Embodiment T5. The method of embodiment T4, wherein the nucleotide having a 3' protecting group comprises triphosphate.

Embodiment T6. The method of embodiment T3, wherein the nucleotide having a 3' protecting group comprises phosphate.

Embodiment T7. The method of embodiment T6, wherein the nucleotide having a 3' protecting group comprises triphosphate.

Embodiment T8. The method of embodiment T1, wherein R2 has a molecular weight of at least 36.

Embodiment T9. The method of embodiment T1, wherein R2 comprises a fluorine nucleus.

Embodiment T10. The method of embodiment T1, wherein R2 comprises at least two carbon nuclei.

Embodiment T11. The method of embodiment T1, wherein R2 comprises a carbon-carbon double bond.

Embodiment T12. The method of embodiment T1, wherein R2 comprises a tertiary carbon.

Embodiment T13. The method of embodiment T12, wherein R2 comprises a tert-butyl moiety.

Embodiment T14. The method of embodiment T1, wherein R2 comprises a cyclic moiety.

Embodiment T15. The method of embodiment T1, wherein R2 comprises a silicon nucleus.

Embodiment T16. The method of embodiment T1, wherein R2 comprises a phenyl ring.

Embodiment T17. The method of embodiment T1, wherein R2 comprises a nitrogen nucleus.

Embodiment T18. The method of embodiment T1, wherein R2 comprises an oxygen nucleus.

Embodiment T19. The method of embodiment T1, wherein R2 comprises a hydroxylate moiety.

Embodiment T20. The method of embodiment T1, wherein the reagent comprising the structure R2-O—NH$_2$ is selected from the group consisting of:

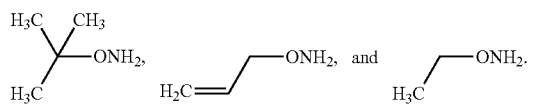

Embodiment T21. The method of embodiment T20, wherein the reagent comprising the structure R2-O—NH$_2$ is

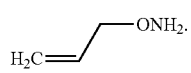

Embodiment T22. The method of embodiment T20, wherein the reagent comprising the structure R2-O—NH$_2$ is

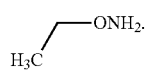

Embodiment T23. The method of embodiment T1, wherein the reagent comprising the structure R2-O—NH$_2$ is selected from the group consisting of:

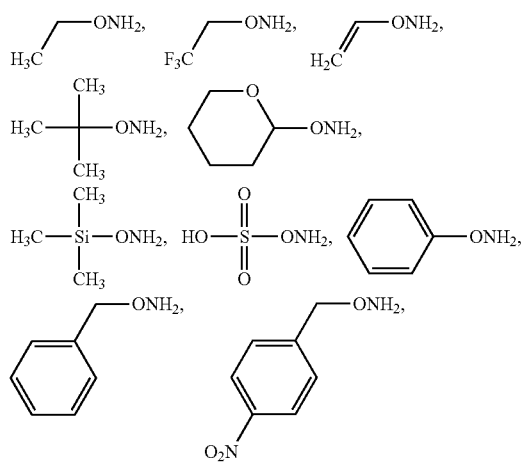

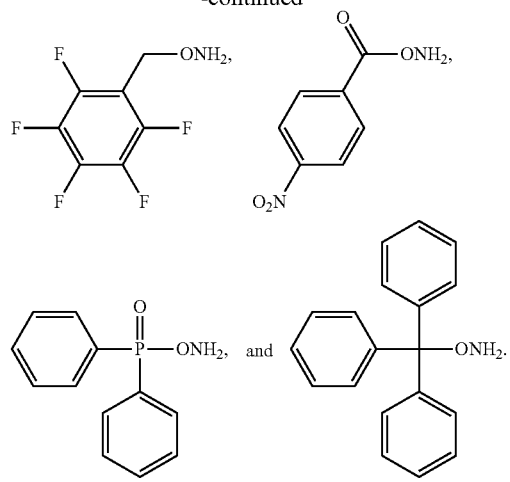

Embodiment T24. The method of any one of embodiments T8 to T23, wherein the 3' blocking group comprises 3'-O-Oxime.

Embodiment T25. The method of any one of embodiments T8 to T23, wherein the 3' blocking group comprises 3'-O-aldoxime.

Embodiment T26. The method of any one of embodiments T8 to T23, wherein the 3' blocking group comprises 3'-O-ketoxime.

Embodiment T27. The method of any one of embodiments T8 to T23, wherein the nucleotide having a 3' protecting group comprises the structure:

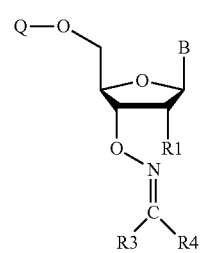

wherein the nucleotide that comprises the 3'-O—NH$_2$ moiety comprises the structure:

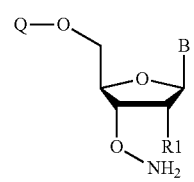

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment T28. The method of any one of embodiments T1 to T27, wherein the method adds a 3' ONH$_2$ in place of a 3' protecting group to at least 94% of a population of nucleotides having a 3' protecting group in no more than 3 hours.

Embodiment T29. The method of any one of embodiments T1 to T27, wherein the method adds a 3' $ONH_2$ in place of a 3' protecting group to at least 96% of a population of nucleotides having a 3' protecting group in no more than 3 hours.

Embodiment T30. The method of any one of embodiments T1 to T27, wherein the method adds a 3' $ONH_2$ in place of a 3' protecting group to at least 98% of a population of nucleotides having a 3' protecting group in no more than 3 hours.

Embodiment T31. The method of any one of embodiments T1 to T27, wherein the method adds a 3' $ONH_2$ in place of a 3' protecting group to at least 98% of a population of nucleotides having a 3' protecting group in no more than 2 hours.

Embodiment T32. The method of any one of embodiments T1 to T27, wherein the method adds a 3' $ONH_2$ in place of a 3' protecting group to at least 98% of a population of nucleotides having a 3' protecting group in no more than 1 hour.

Embodiment T33. The method of any one of embodiments T1 to T32, wherein the nucleotide having a 3' protecting group comprises cytosine, and wherein method degrades no more than 6% of cytosine bases from a population comprising a plurality of said nucleotide having a 3' protecting group comprising cytosine.

Embodiment T34. The method of any one of embodiments T1 to T32, wherein the nucleotide having a 3' protecting group comprises cytosine, and wherein method degrades no more than 5% of cytosine bases from a population comprising a plurality of said nucleotide having a 3' protecting group comprising cytosine.

Embodiment T35. The method of any one of embodiments T1 to T32, wherein the nucleotide having a 3' protecting group comprises cytosine, and wherein method degrades no more than 4% of cytosine bases from a population comprising a plurality of said nucleotide having a 3' protecting group comprising cytosine.

Embodiment T36. The method of any one of embodiments T1 to T32, wherein the nucleotide having a 3' protecting group comprises cytosine, and wherein method degrades no more than 3% of cytosine bases from a population comprising a plurality of said nucleotide having a 3' protecting group comprising cytosine.

Embodiment T37. The method of any one of embodiments T1 to T32, wherein the nucleotide having a 3' protecting group comprises cytosine, and wherein method degrades no more than 2% of cytosine bases from a population comprising a plurality of said nucleotide having a 3' protecting group comprising cytosine.

Embodiment T38. The method of any one of embodiments T1 to T32, wherein the nucleotide having a 3' protecting group comprises cytosine, and wherein method degrades no more than 1% of cytosine bases from a population comprising a plurality of said nucleotide having a 3' protecting group comprising cytosine.

Embodiment T39. A composition comprising a population of cytosine nucleotides wherein at least 94% of the population of cytosine nucleotides comprise a 3'-O—$NH_2$, wherein no more than 8% of the population of cytosine nucleotides comprise a 3' moiety other than —O—$NH_2$, and wherein no more than 6% of the population of cytosine nucleotides comprise a modified cytosine base.

Embodiment T40. The composition of embodiment T39, wherein at least 96% of the population of cytosine nucleotides comprise a 3'-O—$NH_2$.

Embodiment T41. The composition of embodiment T39, wherein at least 98% of the population of cytosine nucleotides comprise a 3'-O—$NH_2$.

Embodiment T42. The composition of embodiment T39, wherein at least 99% of the population of cytosine nucleotides comprise a 3'-O—$NH_2$.

Embodiment T43. The composition of embodiment T39, wherein no more than 6% of the population of cytosine nucleotides comprise a 3' moiety other than —O—$NH_2$.

Embodiment T44. The composition of embodiment T39, wherein no more than 4% of the population of cytosine nucleotides comprise a 3' moiety other than —O—$NH_2$.

Embodiment T45. The composition of embodiment T39, wherein no more than 2% of the population of cytosine nucleotides comprise a 3' moiety other than —O—$NH_2$.

Embodiment T46. The composition of embodiment T39, wherein no more than 1% of the population of cytosine nucleotides comprise a 3' moiety other than —O—$NH_2$.

Embodiment T47. The composition of embodiment T39, wherein no more than 4% of the population of cytosine nucleotides comprise a modified cytosine base.

Embodiment T48. The composition of embodiment T39, wherein no more than 2% of the population of cytosine nucleotides comprise a modified cytosine base.

Embodiment T49. The composition of embodiment T39, wherein no more than 1% of the population of cytosine nucleotides comprise a modified cytosine base.

Embodiment T50. The composition of embodiment T39, wherein at least 98% of the population of cytosine nucleotides comprise a 3'-O—$NH_2$, wherein no more than 1% of the population of cytosine nucleotides comprise a 3' moiety other than —O—$NH_2$, and wherein no more than 1% of the population of cytosine nucleotides comprise a modified cytosine base.

Embodiment T51. The composition of embodiment T39, wherein the composition is an aqueous solution.

Embodiment T52. The composition of embodiment T51, wherein the pH of the solution is no less than 4 and no greater than 8.

Embodiment T53. The composition of embodiment T39, wherein the composition comprises a reagent comprising the structure R2-O—$NH_2$.

Embodiment T54. The composition of embodiment T53, wherein R2 comprises a molecular weight of at least 24.

Embodiment T55. The composition of embodiment T53, wherein R2 comprises a molecular weight of at least 36.

Embodiment T56. The composition of embodiment T53, wherein R2 comprises a fluorine nucleus.

Embodiment T57. The composition of embodiment T53, wherein R2 comprises at least two carbon nuclei.

Embodiment T58. The composition of embodiment T53, wherein R2 comprises a carbon-carbon double bond.

Embodiment T59. The composition of embodiment T53, wherein R2 comprises a tertiary carbon.

Embodiment T60. The composition of embodiment T59, wherein R2 comprises a tert-butyl moiety.

Embodiment T61. The composition of embodiment T53, wherein R2 comprises a cyclic moiety.

Embodiment T62. The composition of embodiment T53, wherein R2 comprises a silicon nucleus.

Embodiment T63. The composition of embodiment T53, wherein R2 comprises a phenyl ring.

Embodiment T64. The composition of embodiment T53, wherein R2 comprises a nitrogen nucleus.

Embodiment T65. The composition of embodiment T53, wherein R2 comprises an oxygen nucleus.

Embodiment T66. The composition of embodiment T53, wherein R2 comprises a hydroxylated moiety.

Embodiment T67. The composition of embodiment T53, wherein the reagent comprising the structure R2-O—NH$_2$ is selected from the group consisting of:

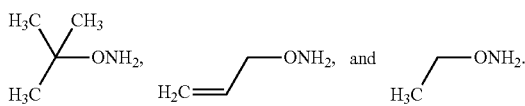

Embodiment T68. The composition of embodiment T53, wherein the reagent comprising the structure R2-O—NH$_2$ is

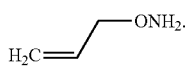

Embodiment T69. The composition of embodiment T53, wherein the reagent comprising the structure R2-O—NH$_2$ is

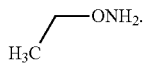

Embodiment T70. The composition of embodiment T53, wherein the reagent comprising the structure R2-O—NH$_2$ is selected from the group consisting of:

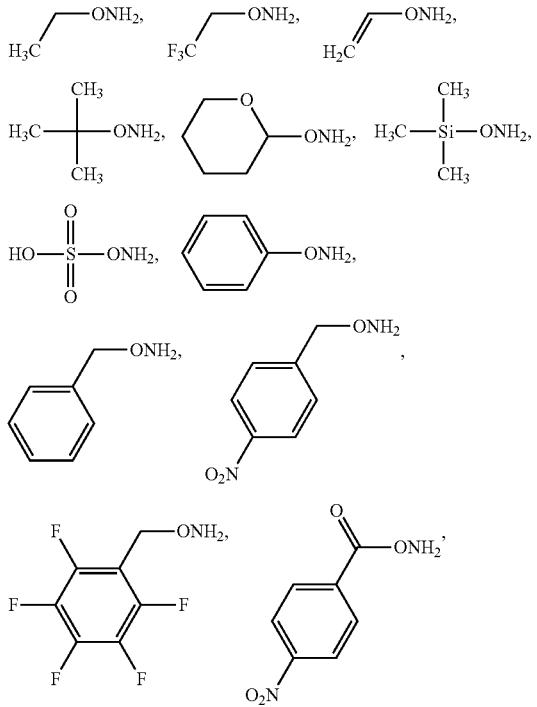

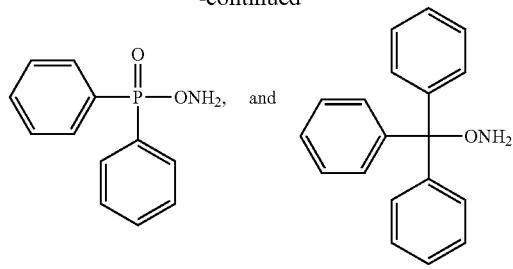

Embodiment T71. The composition of any one of embodiments T39 to T70, wherein the 3' moiety other than —O—NH$_2$ comprises a 3' O-oxime.

Embodiment T72. The composition of any one of embodiments T39 to T70, wherein the 3' moiety other than —O—NH$_2$ comprises a 3' O-aldoxime.

Embodiment T73. The composition of any one of embodiments T39 to T70, wherein the 3' moiety other than —O—NH$_2$ comprises a 3' O-ketoxime.

Embodiment T74. The composition of embodiment T39, wherein the composition comprises a reagent comprising the structure R2-O—NHCH$_3$.

Embodiment T75. The composition of embodiment T39, wherein the composition comprises a reagent comprising the structure R2O—CH$_2$N$_3$.

Embodiment T76. The composition of any one of embodiments T39 to T70, wherein at least some of the cytosine nucleotides having a 3' moiety other than —O—NH$_2$ nucleotide comprise the structure:

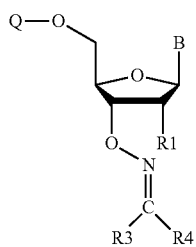

wherein B is a cytosine nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment T77. A method of formulating a sequencing reagent, comprising contacting a composition comprising a 3' protected nucleotide to a reagent comprising a reversible terminator moiety to produce a composition comprising a nucleotide comprising a reversible terminator moiety, and formulating the composition comprising a nucleotide comprising a reversible terminator moiety as a sequencing reagent, wherein formulating the composition comprising a reversible terminator moiety does not comprise further purification of the composition comprising a reversible terminator moiety.

Embodiment T78. The method of embodiment T77, further comprising applying the sequencing reagent to a sequencing reagent to yield a sequencing run of at least 100 bases having a quality score of at least Q30.

Embodiment T79. The method of embodiment T77, wherein the reagent comprising a reversible terminator moiety has a structure R2-O—NH$_2$.

Embodiment T80. The method of embodiment T79, wherein R2 comprises at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety.

Embodiment T81. The method of embodiment T80, wherein R2 comprises at least two carbon nuclei, carbon-carbon double bond, tertiary carbon, tert-butyl moiety, cyclic moiety, or phenyl ring.

Embodiment T82. The method of embodiment T81, wherein R2 is —CH$_2$CH$_3$, —CH$_2$CHCH$_2$, or —C(CH$_3$)$_3$.

Embodiment T83. The method of embodiment T82, wherein R2 is —C(CH$_3$)$_3$.

Embodiment T84. The method of embodiment T79, wherein R2 has a molecular weight of at least 24.

Embodiment T85. The method of embodiment T84, wherein R2 has a molecular weight of at least 36.

Embodiment T86. The method of embodiment T84, wherein R2 has a molecular weight of at least 57.

Embodiment T87. The method of embodiment T84, wherein R2 has a molecular weight of at least 100.

Embodiment T88. The method of embodiment T84, wherein R2 has a molecular weight of at least 200.

Embodiment T89. The method of embodiment T84, wherein R2 has a molecular weight of at least 300.

Embodiment T90. The method of embodiment T84, wherein R2 has a molecular weight of at least 400.

Embodiment T91. The method of embodiment T84, wherein R2 has a molecular weight of at least 500.

Embodiment T92. The method of embodiment T84, wherein R2 has a molecular weight of at least 600.

Embodiment T93. The method of embodiment T84, wherein R2 has a molecular weight of at least 700.

Embodiment T94. The method of embodiment T84, wherein R2 has a molecular weight of at least 800.

Embodiment T95. The method of embodiment T84, wherein R2 has a molecular weight of at least 900.

Embodiment T96. The method of embodiment T79, wherein R2 comprises at least two carbon nuclei.

Embodiment T97. The method of embodiment T79, wherein R2 comprises a fluorine nucleus, silicon nucleus, nitrogen nucleus, oxygen nucleus, or hydroxylate moiety.

Embodiment T98. The method of embodiment T79, wherein the 3' protected nucleotide comprises a 3'-O-oxime moiety.

Embodiment T99. The method of embodiment T98, wherein the oxime is an aldoxime.

Embodiment T100. The method of embodiment T98, wherein the oxime is a ketoxime.

Embodiment T101. The method of embodiment T79, wherein the composition comprising a nucleotide comprising a reversible terminator moiety comprises no more than 6% of the 3' protected nucleotide relative to 3' protected nucleotide present initially.

Embodiment T102. The method of embodiment T101, wherein the composition comprising a nucleotide comprising a reversible terminator moiety comprises no more than 5% of the 3' protected nucleotide relative to 3' protected nucleotide present initially.

Embodiment T103. The method of embodiment T101, wherein the composition comprising a nucleotide comprising a reversible terminator moiety comprises no more than 4% of the 3' protected nucleotide relative to 3' protected nucleotide present initially.

Embodiment T104. The method of embodiment T101, wherein the composition comprising a nucleotide comprising a reversible terminator moiety comprises no more than 3% of the 3' protected nucleotide relative to 3' protected nucleotide present initially.

Embodiment T105. The method of embodiment T101, wherein the composition comprising a nucleotide comprising a reversible terminator moiety comprises no more than 2% of the 3' protected nucleotide relative to 3' protected nucleotide present initially.

Embodiment T106. The method of embodiment T101, wherein the composition comprising a nucleotide comprising a reversible terminator moiety comprises no more than 1% of the 3' protected nucleotide relative to 3' protected nucleotide present initially.

Embodiment T107. The method of embodiment T79, wherein the composition comprising a nucleotide comprising a reversible terminator moiety comprises degraded or modified dC nucleobases at a concentration of no more than 6% of total dC nucleobases in the composition comprising a nucleotide comprising a reversible terminator moiety.

Embodiment T108. The method of embodiment T79, wherein the composition comprising a nucleotide comprising a reversible terminator moiety comprises degraded or modified dC nucleobases at a concentration of no more than 5% of total dC nucleobases in the composition comprising a nucleotide comprising a reversible terminator moiety.

Embodiment T109. The method of embodiment T79, wherein the composition comprising a nucleotide comprising a reversible terminator moiety comprises degraded or modified dC nucleobases at a concentration of no more than 4% of total dC nucleobases in the composition comprising a nucleotide comprising a reversible terminator moiety.

Embodiment T110. The method of embodiment T79, wherein the composition comprising a nucleotide comprising a reversible terminator moiety comprises degraded or modified dC nucleobases at a concentration of no more than 3% of total dC nucleobases in the composition comprising a nucleotide comprising a reversible terminator moiety.

Embodiment T111. The method of embodiment T79, wherein the composition comprising a nucleotide comprising a reversible terminator moiety comprises degraded or modified dC nucleobases at a concentration of no more than 2% of total dC nucleobases in the composition comprising a nucleotide comprising a reversible terminator moiety.

Embodiment T112. The method of embodiment T79, wherein the composition comprising a nucleotide comprising a reversible terminator moiety comprises degraded or modified dC nucleobases at a concentration of no more than 1% of total dC nucleobases in the composition comprising a nucleotide comprising a reversible terminator moiety.

Embodiment T113. A method for modifying a nucleotide, comprising reacting a nucleotide comprising a 3'-O-oxime moiety with a reagent comprising the structure R2-O—NH$_2$ to produce a nucleotide comprising a 3'-O—NH$_2$ moiety, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment T114. The method of embodiment T113, wherein the nucleotide that comprises the 3'-O-oxime moiety comprises the structure:

wherein the nucleotide that comprises the 3'-O—NH$_2$ moiety comprises the structure:

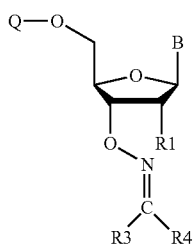

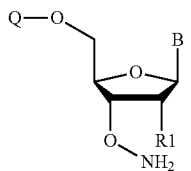

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment T115. The method of embodiment T113, wherein the reaction occurs in an aqueous solution.

Embodiment T116. The method of embodiment T115, wherein the nucleotide is attached to a solid support in contact with the aqueous solution.

Embodiment T117. The method of embodiment T115, wherein the reagent that comprises the structure R2-O—NH$_2$ is attached to a solid support in contact with the aqueous solution.

Embodiment T118. The method of any one of embodiments T113 to T117, wherein the nucleobase is a purine or pyrimidine.

Embodiment T119. The method of embodiment T118, wherein the nucleobase is independently adenine, cytosine, guanine, thymine, or uracil.

Embodiment T120. The method of embodiment T118, wherein the nucleobase is complementary to adenine, cytosine, guanine, thymine, or uracil.

Embodiment T121. The method of embodiment T118, wherein the nucleobase is independently 5-methylcytosine, hypoxanthine, xanthine, inosine, isoguanine, isocytosine, or 7-deazaguanine.

Embodiment T122. The method of any one of embodiments T113 to T121, wherein the pH of the solution is no less than 4 and no greater than 8.

Embodiment T123. The method of any one of embodiments T113 to T122, wherein the nucleotide that is produced comprises a deoxynucleotide.

Embodiment T124. The method of embodiment T123, wherein the nucleotide that is produced comprises:

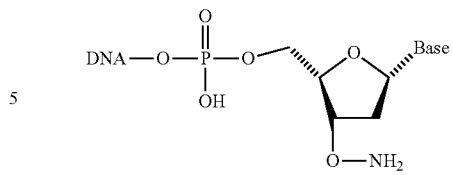

wherein Base is the nucleobase, and wherein DNA is independently a single stranded deoxyribonucleic acid or double stranded deoxyribonucleic acid.

Embodiment T125. The method of any one of embodiments T113 to T124, wherein the reagent is independently one of:

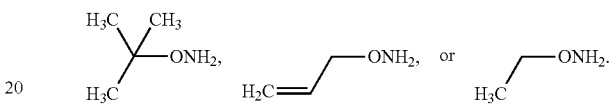

Embodiment T126. A solution comprising a nucleotide comprising a 3'-O-oxime moiety and a reagent comprising the structure R2-O—NH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment T127. The solution of embodiment T126, wherein the nucleotide comprises the structure:

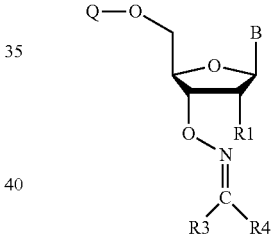

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment T128. The solution of embodiment T127, wherein R1 is H.

Embodiment T129. The solution of embodiment T128, wherein Q is deoxyribonucleic acid.

Embodiment T130. The solution of embodiment T127, wherein R1 is OH.

Embodiment T131. The solution of embodiment T130, wherein Q is ribonucleic acid.

Embodiment T132. The solution of embodiment T126, wherein the solution is an aqueous solution.

Embodiment T133. The solution of embodiment T132, wherein the nucleotide is attached to a solid support and wherein the solid support is in contact with the solution.

Embodiment T134 The solution of embodiment T132, wherein the reagent that comprises the structure R2-O—NH$_2$ is attached to a solid support in contact with the aqueous solution.

Embodiment T135. The solution of any one of embodiments T126 to T134, wherein the nucleobase is a purine or pyrimidine.

Embodiment T136. The solution of embodiment T135, wherein the nucleobase is independently adenine, cytosine, guanine, thymine, or uracil.

Embodiment T137. The solution of embodiment T135, wherein the nucleobase is complementary to adenine, cytosine, guanine, thymine, or uracil.

Embodiment T138. The solution of embodiment T135, wherein the nucleobase is independently 5-methylcytosine, hypoxanthine, xanthine, inosine, isoguanine, isocytosine, or 7-deazaguanine.

Embodiment T139. The solution of any one of embodiments T126 to T138, wherein the nucleobase comprises an exogenous label moiety.

Embodiment T140. The solution of any one of embodiments T126 to T139, wherein the pH of the solution is no less than 4 and no greater than 8.

Embodiment T141. The solution of any one of embodiments T126 to T140, wherein the R2-O—NH$_2$ molecule is independently one of:

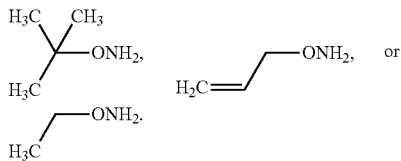

Embodiment T142. A kit comprising a first vessel containing a nucleotide comprising a 3'-O-oxime moiety and a second vessel containing a reagent comprising the structure R2-O—NH$_2$, wherein R2 is independently alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment T143. The kit of embodiment T142, wherein the nucleotide comprises the structure:

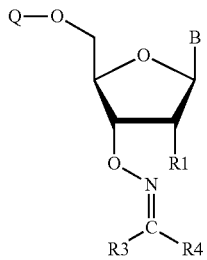

wherein B is a nucleobase; R1 is independently halogen, OCH$_3$, H or OH, Q is independently monophosphate, diphosphate, triphosphate, or nucleic acid, and R3 and R4 are independently H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment T144. The kit of embodiment T142, wherein the kit comprises an RFID tag or bar code.

Embodiment T145. The kit of embodiment T143 or T144, wherein Q is independently a single stranded deoxyribonucleic acid or double stranded deoxyribonucleic acid.

Embodiment T146. The kit of embodiment T145, wherein the nucleotide is attached to a solid support.

Embodiment T147. The kit of embodiment T142, wherein the reagent that comprises the structure R2-O—NH$_2$ is attached to a solid support.

Embodiment T148. The kit of any one of embodiments T142 to T147, wherein the nucleobase is a purine or pyrimidine.

Embodiment T149. The kit of embodiment T148, wherein the nucleobase is independently adenine, cytosine, guanine, thymine, or uracil.

Embodiment T150. The kit of embodiment T148, wherein the nucleobase is complementary to adenine, cytosine, guanine, thymine, or uracil.

Embodiment T151. The kit of embodiment T148, wherein the nucleobase is independently 5-methylcytosine, hypoxanthine, xanthine, inosine, isoguanine, isocytosine, or 7-deazaguanine.

Embodiment T152. The kit of any one of embodiments T142 to T151, wherein the nucleobase comprises an exogenous label moiety.

Embodiment T153. The kit of any one of embodiments T142 to T152, wherein the R2-O—NH$_2$ molecule is independently one of:

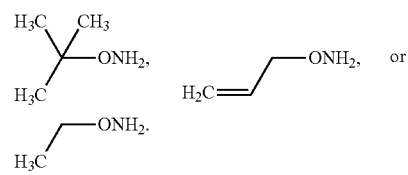

Additional Embodiments

Embodiment 1. A method of replacing a protecting group by a blocking group at a 3' position of a nucleotide, comprising contacting the nucleotide and a reagent comprising the structure R2-block, wherein R2 has a molecular weight of at least 24, wherein R2-block is water soluble, and wherein block comprises a blocking group moiety.

Embodiment 2. The method of embodiment 1, wherein block comprises a reversible terminator moiety.

Embodiment 3. The method of embodiment 2, wherein the reversible terminator moiety does not preclude assembly of a nucleotide reversibly terminated thereby into a ternary complex.

Embodiment 4. The method of any one of embodiments 1 to 3, wherein R2-block is selected from the group consisting of R2-O—NH$_2$, R2-O—NHCH$_3$, R2-O—NHCOCH$_3$, or R2O—CH$_2$N$_3$.

Embodiment 5. The method of any one of embodiments 1 to 4, wherein R2-block is R2O—CH$_2$N$_3$.

Embodiment 6. The method of any one of embodiments 1 to 4, wherein R2-block is R2-O—NH$_2$.

Embodiment 7. The method of any one of embodiments 1 to 4, wherein the nucleotide comprising a 3' protecting group is:

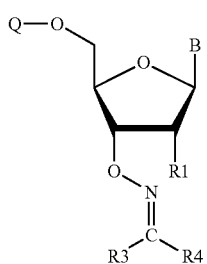

wherein the nucleotide comprising a 3' blocking group is:

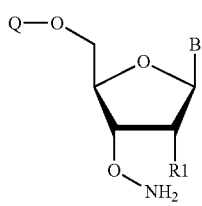

wherein B is a nucleobase; R1 is independently halogen, OCH₃, H or OH, Q is independently monophosphate, diphosphate, triphosphate, or nucleic acid, and R3 and R4 are independently H, CH₃, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, or an optionally substituted variant thereof.

Embodiment 8. The method of any one of embodiments 1 to 7, wherein the protecting group comprises an —O-oxime.

Embodiment 9. The method of embodiment 8, wherein the —O-oxime moiety has the formula: —O—N═C(R3)(R4); and R3 and R4 are independently hydrogen, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment 10. The method of embodiment 9, wherein R3 is Hydrogen.

Embodiment 11. The method of any one of embodiments 9 to 10, wherein R4 is Hydrogen.

Embodiment 12. The method of any one of embodiments 1 to 11, wherein the nucleotide comprises a triphosphate moiety.

Embodiment 13. The method of any one of embodiments 1 to 4, wherein
R2 is —C(R6)(R7)(R8), —C(O)(R6), —P(O)(R6)(R7), —C(R6)(═C(R7)(R8)), —Si(R6)(R7)(R8), —SO₂(R6), substituted or unsubstituted cycloalkyl, substituted or unsubstituted cycloalkenyl, substituted or unsubstituted cycloalkynyl, substituted or unsubstituted heteroalicyclyl, substituted or unsubstituted aryl, substituted or unsubstituted heteroaryl; and
R6, R7, and R8 are independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —SF₅, —N₃, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heteroalicyclyl, substituted or unsubstituted aralkyl, substituted or unsubstituted heteroaralkyl, or substituted or unsubstituted (heteroalicyclyl)alkyl.

Embodiment 14. The method of embodiment 13, wherein R2 is —C(R6)(R7)(R8) and R6, R7, and R8 are not all hydrogen.

Embodiment 15. The method of embodiment 13, wherein R2 is not unsubstituted methyl.

Embodiment 16. The method of embodiment 13, wherein R2 is not unsubstituted ethyl.

Embodiment 17. The method of embodiment 13, wherein R2 is not unsubstituted propyl.

Embodiment 18. The method of embodiment 13, wherein R2-block has a formula selected from the group consisting of the following:

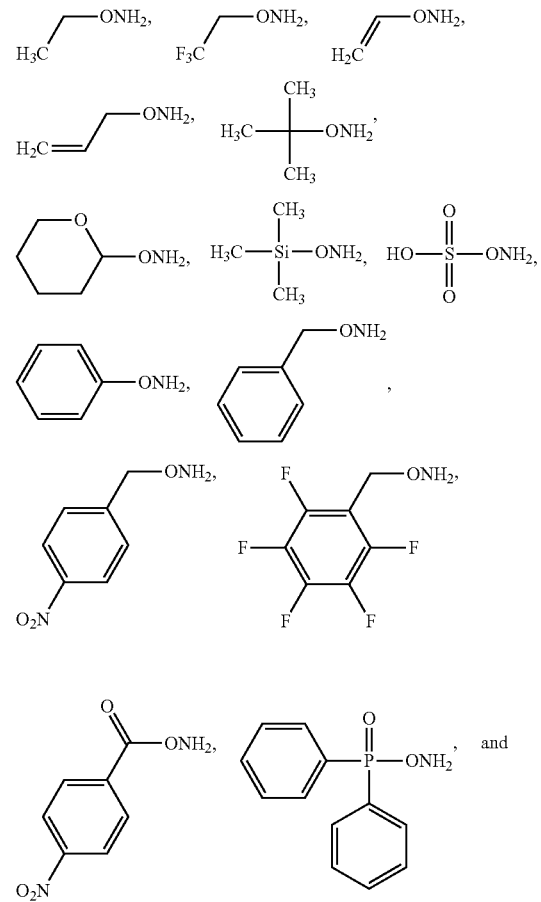

-continued

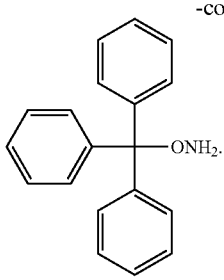

Embodiment 19. The method of embodiment 18, wherein R2-block has a formula selected from the group consisting of:

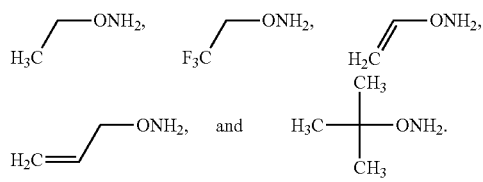

Embodiment 20. The method of embodiment 19, wherein R2-block has a formula

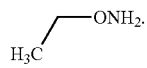

Embodiment 21. The method of embodiment 19, wherein R2-block has a formula

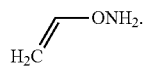

Embodiment 22. The method of embodiment 19, wherein R2-block has a formula

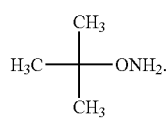

Embodiment 23. The method of embodiment 13, wherein R2 comprises a hydroxylated moiety.

Embodiment 24. The method of embodiment 13, wherein R2 comprises at least two carbon nuclei, a fluorine nucleus, carbon-carbon double bond, tertiary carbon, tert-butyl moiety, cyclic moiety, silicon nucleus, phenyl ring, nitrogen nucleus, oxygen nucleus, or hydroxylate moiety.

Embodiment 25. The method of embodiment 13, wherein R2 has a molecular weight of no more than 280 g/mol.

Embodiment 26. The method of embodiment 13, wherein R2 has a molecular weight of no more than 100 g/mol.

Embodiment 27 The method of any one of embodiments 1 to 4, wherein the method adds a blocking group in place of a 3' protecting group to at least 94% of a population of nucleotides having a 3' protecting group in no more than 3 hours at 25° C.

Embodiment 28. The method of embodiment 27, wherein the method adds a blocking group in place of a 3' protecting group to at least 98% of a population of nucleotides having a 3' protecting group in no more than 3 hours at 25° C.

Embodiment 29. The method of embodiment 28, wherein the method degrades no more than 6% of cytosine nucleobases in a population of nucleotides each comprising a cytosine nucleobase.

Embodiment 30. The method of embodiment 29, wherein the method degrades no more than 1% of cytosine bases from the population of nucleotides having a cytosine nucleobase.

Embodiment 31. The method of any one of embodiments 1 to 19, wherein the method adds a blocking group in place of a 3' protecting group to at least 94% of a population of nucleotides having a 3' protecting group in no more than 3 hours at 25° C.

Embodiment 32. The method of embodiment 31, wherein the method adds a blocking group in place of a 3' protecting group to at least 98% of a population of nucleotides having a 3' protecting group in no more than 3 hours at 25° C.

Embodiment 33. The method of embodiment 32, wherein the method degrades no more than 6% of cytosine nucleobases in a population of nucleotides each comprising a cytosine nucleobase.

Embodiment 34. The method of embodiment 33, wherein the method degrades no more than 1% of cytosine nucleobases from the population of nucleotides having a cytosine nucleobase.

EXAMPLES

Example 1. This example demonstrates the efficiency of nucleotide deblocking using various alkoxyamine reagents and inertness of the deblocking reagents to unwanted modification and degradation of nucleotide structure. Each aminooxy deblocking reagent was formulated as a 3.2M solution in water, and the pH was adjusted to 5.25 with 10M sodium hydroxide. Each of these aminooxy solutions was then mixed 1:1 with a 100 mM solution of dCTP oxime triphosphate and incubated at 25 C for 1 hr. At this time, the reaction was diluted 50-fold with 10% isopropyl methyl ketone in 50% isopropanol/water. Percent consumption and degradation was analyzed by HPLC using a Phenomenex Gemini C18 column (5 pm NX-X18 110 Å, LC Column 250×4.6 mm).

FIG. 1A shows a plot of percent nucleotide degradation vs. percent consumption of 3' oxime for dCTP when treated with various candidate reagents. The results indicate that when reacting dCTP-3'-oxime with reagents having structure R2-ONH$_2$, the species having the R2 moiety of —CH$_3$, —CH$_2$CH$_3$, —CH$_2$CHCH$_2$, or —C(CH$_3$)$_3$ produce a higher yield of 3'-ONH$_2$ nucleotide compared to reaction with hydroxylamine. The candidate reagent having R2 moiety of —C(CH$_3$)$_3$ produced the highest yield of 3'-ONH$_2$ nucleotide.

The results of FIG. 1A showed that the species having the R2 moiety of —CH$_3$, —CH$_2$CHCH$_2$, or —C(CH$_3$)$_3$ yielded substantially less unwanted degradation of the nucleotide compared to treatment with hydroxylamine. Species having the R2 moiety of —CH$_2$CH$_3$ demonstrated a degradation level that was roughly comparable to treatment with hydroxylamine. The reagent having R2 moiety of —C(CH$_3$)$_3$ demonstrated the lowest level of unwanted nucleotide degradation among the reagents tested in FIG. 1A.

Example 2. The composition of FIG. 1 produced through the use of tert-butyl-O—NH$_2$ was used to formulate a sequencing reagent without further purification. The sequencing reagent, which further comprised a polymerase was used in a sequencing run, and a read quality of at least Q30 was observed for at least 100 bases of the read.

This example demonstrates that practice of the method herein produced nucleotide compositions that are suitable to be formulated into sequencing reagents without further purification, such as sequencing reagents comprising a polymerase, surfactant, or other reagent suitable for a sequencing reaction.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. A method for modifying a nucleotide, comprising reacting a nucleotide comprising a 3'-O-oxime moiety with a reagent to produce a nucleotide comprising a 3'-O—NH$_2$ moiety, wherein the nucleotide that comprises the 3'-O-oxime moiety is:

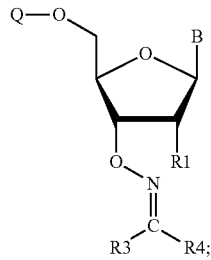

wherein the nucleotide that comprises the 3'-O—NH$_2$ moiety is:

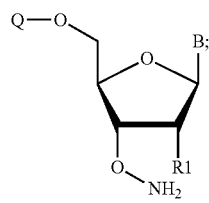

wherein B is a nucleobase; R1 is halogen, OCH$_3$, H or OH, Q is monophosphate, diphosphate, or triphosphate, and R3 and R4 are H, CH$_3$, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, wherein either R3 or R4, or both R3 and R4 are not H; and, wherein the reagent is independently:

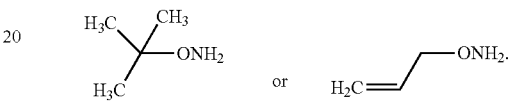

2. The method of claim 1, wherein R3 is —CH$_3$.
3. The method of claim 1, wherein R4 is —CH$_3$.
4. The method of claim 1, wherein Q is triphosphate.
5. The method of claim 1, wherein the reagent is

6. The method of claim 1, wherein the reagent is

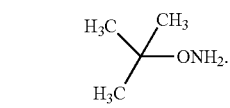

* * * * *